United States Patent [19]

Schaefer et al.

[11] Patent Number: 5,783,522

[45] Date of Patent: Jul. 21, 1998

[54] SUBSTITUTED 2-PHENYLPYRIDINES

[75] Inventors: Peter Schaefer, Ottersheim; Gerhard Hamprecht, Weinheim; Elisabeth Heistracher, Ludwigshafen; Hartmann Koenig, Limburgerhof; Ralf Klintz, Gruenstadt; Peter Muenster, Neulussheim; Harald Rang, Altrip; Karl-Otto Westphalen, Speyer; Matthias Gerber, Limburgerhof; Helmut Walter, Obrigheim, all of Germany

[73] Assignee: BASF Aktiengesellschaft, Ludwigshafen, Germany

[21] Appl. No.: 592,355

[22] PCT Filed: Jul. 11, 1994

[86] PCT No.: PCT/EP94/02263

§ 371 Date: Jan. 11, 1996

§ 102(e) Date: Jan. 11, 1996

[87] PCT Pub. No.: WO95/02580

PCT Pub. Date: Jan. 26, 1995

[30] Foreign Application Priority Data

Jul. 16, 1993 [DE] Germany .......... 43 23 916.1

[51] Int. Cl.$^6$ .......... A01N 43/40; C07D 213/61
[52] U.S. Cl. .......... 504/294; 504/247; 504/254; 504/255; 504/260; 546/280.4; 546/283.7; 546/302; 546/303; 546/329; 546/330; 546/335; 546/337; 546/339; 546/342; 546/344; 546/345; 546/144; 546/173; 546/279.1; 546/281.4
[58] Field of Search .......... 546/334, 342, 546/344, 345; 504/244, 254

[56] References Cited

U.S. PATENT DOCUMENTS 5,081,287  1/1992  Peake et al. .......... 560/219

FOREIGN PATENT DOCUMENTS

| 2039770 | 10/1991 | Canada . |
|---|---|---|
| 2078469 | 3/1993 | Canada . |
| 067 511 | 12/1982 | European Pat. Off. . |
| 167 491 | 1/1986 | European Pat. Off. . |
| 263 958 | 4/1988 | European Pat. Off. . |
| 303415 | 2/1989 | European Pat. Off. . |
| 412 681 | 2/1991 | European Pat. Off. . |
| 451 585 | 10/1991 | European Pat. Off. . |
| 537 463 | 4/1993 | European Pat. Off. . |
| 40 20 257 | 1/1992 | Germany . |
| 1211586-A | 2/1988 | Japan . |
| 5301870-A | 4/1992 | Japan . |
| 92/22203 | 12/1992 | WIPO . |
| 93/07137 | 4/1993 | WIPO . |
| 94/05153 | 3/1994 | WIPO . |
| 94/10118 | 5/1994 | WIPO . |

OTHER PUBLICATIONS

T. Haga, *Structure, Activity, and Ecotoxicology of Agrochemicals*, ch. 4, 1992, pp. 103–119.
Katagiri et al., *Chem.Pharm.Bull*, 36, 1988, pp. 3354–3372.
Boy et al., *Synlett*, Dec. 1991, vol. 12, pp. 923–924.
Frigerio, *Pest. Science*, vol. 21, No. 3, 1987, pp. 175–179.
*Chem. Abst.*, vol. 114, No. 11, 96724k:Izv. Timiryazevsk.S-Kh. Akad. 3, pp. 155–150.
*Chem. Abst.*, vol. 113, No. 19, 171837j: Nippon Kagaku Kaishi 5, pp. 466–471.

*Primary Examiner*—Bernard Dentz
*Attorney, Agent, or Firm*—Keil & Weinkauf

[57] ABSTRACT

Substituted 2-phenylpyridines I

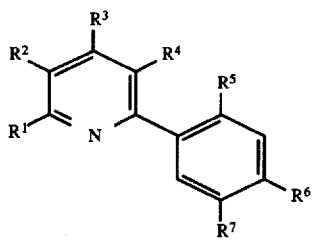

$R^1, R^3$=H, halogen, alkyl, haloalkyl, alkoxyalkyl, alkoxy, alkoxyalkoxy, OH, haloalkoxy, alkylcarbonyloxy, haloalkylcarbonyloxy, SH, alkylthio, alkylsulfinyl, alkylsulfonyl, haloalkylthio, haloalkylsulfinyl, haloalkylsulfonyl, CHO, CN, $CO_2H$, alkoxycarbonyl, alkoxyalkoxycarbonyl, haloalkoxycarbonyl, alkylcarbonyl, haloalkylcarbonyl, alkoxyalkylcarbonyl, $CONH_2$, alkyl-aminocarbonyl, dialkylaminocarbonyl, pyrrolidinyl-carbonyl piperidylcarbonyl, morpholinylcarbonyl, $NO_2$, $NH_2$, alkylamino, dialkylamino, pyrrolidinyl, piperidinyl, morpholinyl, alkylcarbonylamino, haloalkylcarbonylamino, alkylsulfonylamino;

$R^2$=halogen, CN, $NO_2$, alkyl, haloalkyl, alkoxy, haloalkoxy, alkylthio, haloalkylthio; or $R^1+R^2$ or $R^2+R^3$=trimethylene or tetramethylene chain;

$R^4$=halogen, alkyl, haloalkyl, alkoxyalkyl, alkoxy, alkoxyalkoxy, OH, haloalkoxy, alkylcarbonyloxy, haloalkylcarbonyloxy, SH, alkylthio, alkylsulfinyl, alkylsulfonyl, haloalkylthio, haloalkylsulfinyl, haloalkylsulfonyl, CHO, CN, $CO_2H$, alkoxycarbonyl, alkoxyalkoxycarbonyl, haloalkoxycarbonyl, alkylcarbonyl, haloalkylcarbonyl, alkoxyalkylcarbonyl, $NO_2$, $NH_2$, alkylamino, dialkylamino, pyrrolidinyl, piperidinyl, morpholinyl, alkylcarbonylamino, haloalkylcarbonylamino, alkylsulfonylamino;

$R^5$=hydrogen or halogen;

$R^6$=halogen, CN, $NO_2$, OH, $CF_3$, $C_1$–$C_6$-alkyl, $C_1$–$C_4$-alkoxy;

$R^7$=various radicals; and the N-oxides of I and the agriculturally utilizable salts of I where these exist, excepting those compounds I where $R^2$ is $C_1$–$C_4$-alkoxy and $R^1$ and/or $R^3$ is carboxyl or the salt, ester or amide thereof.

15 Claims, No Drawings

SUBSTITUTED 2-PHENYLPYRIDINES

This application is a 371 of PCT/EP94/02263 filed Jul. 11, 1994.

The present invention relates to novel substituted 2-phenylpyridines of the formula I

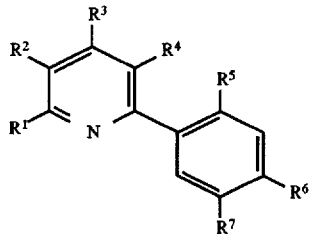

in which the variables have the following meanings:

$R^1$, $R^3$, independently of one another, hydrogen, halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy, $C_1$-$C_4$-alkoxy, hydroxyl, $C_1$-$C_4$-haloalkoxy, ($C_1$-$C_5$-alkyl)carbonyloxy, ($C_1$-$C_5$-Haloalkyl)carbonyloxy, SH, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, formyl, cyano, hydroxycarbonyl, ($C_1$-$C_4$-alkoxy)carbonyl, $C_1$-$C_4$-alkoxy-($C_1$-$C_4$-alkoxy)carbonyl, ($C_1$-$C_4$-haloalkoxy)carbonyl, ($C_1$-$C_4$-alkyl)carbonyl, ($C_1$-$C_4$-haloalkyl)carbonyl, $C_1$-$C_4$-alkoxy-($C_1$-$C_4$-alkyl)carbonyl, $CONH_2$, ($C_1$-$C_4$-alkyl)amino- carbonyl, di-($C_1$-$C_4$-alkyl) aminocarbonyl, pyrrolidinylcarbonyl, piperidinylcarbonyl, morpholinylcarbonyl, nitro, amino, $C_1$-$C_4$-alkylamino, di-($C_1$-$C_4$-alkyl)amino, pyrrolidinyl, piperidinyl, morpholinyl, ($C_1$-$C_4$-alkyl) carbonylamino, ($C_1$-$C_4$-haloalkyl)carbonylamino or $C_1$-$C_4$-alkylsulfonylamino;

$R^2$ halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, or $C_1$-$C_4$-haloalkylthio or together with $R^1$ or with $R^3$ a trimethylene or tetramethylene chain;

$R^4$ halogen, $C_1$-$C_4$-alkyl, $C_1$-$C_4$-haloalkyl, $C_1$-$C_4$-alkoxy-$C_1$-$C_4$- alkyl, $C_1$-$C_4$-haloalkoxy, ($C_1$-$C_5$-alkyl)carbonyloxy, ($C_1$-$C_5$-haloalkyl)carbonyloxy, SH, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, formyl, cyano, hydroxycarbonyl, ($C_1$-$C_4$-alkoxy)carbonyl, $C_1$-$C_4$-alkoxy-($C_1$-$C_4$-alkoxy)carbonyl, ($C_1$-$C_4$-haloalkoxy)carbonyl, ($C_1$-$C_4$-alkyl)carbonyl, ($C_1$-$C_4$-haloalkyl)carbonyl, $C_1$-$C_4$-alkoxy-($C_1$-$C_4$-alkyl) carbonyl, nitro, amino, $C_1$-$C_4$-alkylamino, di-($C_1$-$C_4$-alkyl)amino, pyrrolidinyl, piperidinyl, morpholinyl, ($C_1$-$C_4$-alkyl)carbonylamino, ($C_1$-$C_4$-haloalkyl)carbonylamino or $C_1$-$C_4$-alkylsulfonylamino;

$R^5$ hydrogen or halogen;

$R^6$ halogen, cyano, nitro, hydroxyl, trifluoromethyl, $C_1$-$C_6$-alkyl or $C_1$-$C_4$-alkoxy;

$R^7$ chlorine, bromine, iodine, cyano, nitro, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, —($C_1$-$C_8$-alkylene)-O—$R^8$, —($C_2$-$C_8$-alkenylene)-O—$R^8$, —($C_2$-$C_8$-alkynylene)-O—$R^8$, —($C_1$-$C_8$-alkylene)-S—$R^8$, —($C_2$-$C_8$-alkenylene)-S—$R^8$; —($C_2$-$C_8$-alkynylene)-S—$R^8$, —($C_1$-$C_8$-alkylene)-SO—$R^8$, —($C_2$-$C_8$-alkenylene)-SO—$R^8$, —($C_2$-$C_8$-alkynylene)-SO—$R^8$, —($C_1$-$C_8$-alkylene)-$SO_2$—$R^8$, —($C_2$-$C_8$-alkenylene)-$SO_2$—$R^8$; —($C_2$-$C_8$-alkynylene)-$SO_2$—$R^8$, —O—$R^8$, —S—$R^8$, —SO—$R^8$, —$SO_2$—$R^8$, chlorosulfonyl, —$SO_2$—O—$R^8$, —$SO_2$—N($R^9$,$R^{10}$), —$SO_2$—$NR^9$(CO—$R^{12}$), —N($R^9R^{10}$), —$NR^{11}$(CO—$R^{12}$), —$NR^{11}$($SO_2$—$R^{13}$), —N($SO_2$—$R^{13}$) $SO_2$—$R^{14}$), —N($SO_2$—$R^{13}$) (CO—$R^{12}$), —NH—CO—O—$R^8$, —O—CO—NH—$R^9$, —O—CO—$R^{12}$, —NH—CO—$NHR^9$, —O—CS—N ($C_1$-$C_4$-alkyl)$_2$, —O—CS—$NH_2$, cyano-$C_1$-$C_4$-alkyl, —CO—O—$R^8$, —CO—O—N=C($R^{26}$,$R^{27}$), —CO—O—$CH_2$—O—N=C($R^{30}$,$R^{31}$), —CO—O—C($R^{28}$,$R^{29}$)—$CH_2$—O—N=C($R^{30}$,$R^{31}$), —CO—N($R^9$,$R^{10}$), —CS—N($R^9$,$R^{10}$), —CO—NH—$SO_2$—($C_1$-$C_4$-alkyl), isoxazolidinylcarbonyl, formyl, —CO—$R^{15}$, hydroxycarbonyl-$C_1$-$C_6$-alkyl, ($C_1$-$C_6$-alkoxy) carbonyl-$C_1$-$C_6$-alkyl, —C$R^{15}$=C($R^{16}$)—CHO, —C($R^{15}$)=C($R^{16}$)—CO—O—$R^8$, —C($R^{15}$)=C($R^{16}$)—CO—N($R^9$,$R^{10}$), —C($R^{15}$)=C ($R^{16}$)—CO—$R^{17}$, —CH=N—O—$R^8$, —CH(X$R^{18}$,Y$R^{19}$), —$CH_2$—CH(halogen)—CO—O—$R^8$, —$CH_2$—CH(halogen)-CO—N($R^9$,$R^{10}$), —$CH_2$—CH(halogen)-CO—($C_1$-$C_4$-alkyl), —$CH_2$—CH(halogen)-CN, —C(($C_1$-$C_4$-alkoxy)=N—O—$R^8$, —C($R^{15}$)=C($R^{16}$)-C($C_1$-$C_4$-alkoxy)=N—O—$R^8$, —CH=CH—CH=CH—CO—O—$R^8$

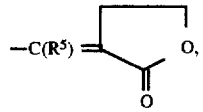

—C($R^{15}$)=N—O—$R^8$, —CO—OCH=N—OH, —CO—OCH=N—O—($C_1$-$C_4$-alkyl), —CO—OC ($C_1$-$C_4$-alkyl)=N—OH, —CO—OC ($C_1$-$C_4$-alkyl)=N—O—($C_1$-$C_4$-alkyl), —CO—O—($C_1$-$C_4$-alkylene)-CH=N—OH, —CO—O—($C_1$-$C_4$-alkylene)-CH=N—O—($C_1$-$C_4$-alkyl), —CO—O—($C_1$-$C_4$-alkylene)-C($C_1$-$C_4$-alkyl)=N—OH, —CO—O—($C_1$-$C_4$-alkylene)-C($C_1$-$C_4$-alkyl)=N—O—($C_1$-$C_4$-alkyl), —($C_1$-$C_8$-alkylene)-O—CO—($C_1$-$C_4$-alkyl), —CH=C=$CH_2$, —CH=C=CH—($C_1$-$C_4$-alkyl),

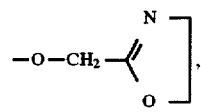

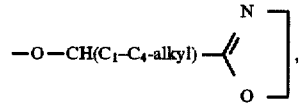

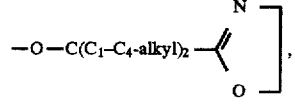

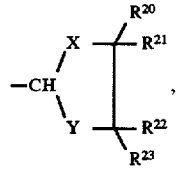

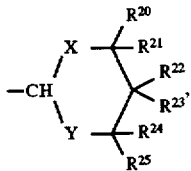

5- or 6-membered heteroaryl with one to three hetero atoms selected from a group comprising one or two nitrogen atoms and one oxygen or sulfur atom, it being possible for each heteroaromatic ring atom which can be substituted to carry, if desired, a radical selected from the group comprising nitro, halogen, $C_1$–$C_4$-alkyl, $C_1$–$C_4$-alkoxy, $C_1$–$C_4$-alkylthio und ($C_1$–$C_4$-alkoxy) carbonyl;

$R^8$ hydrogen, $C_1$–$C_8$-alkyl, $C_1$–$C_8$-haloalkyl, $C_4$–$C_7$-cycloalkyl, which in turn can carry one to three $C_1$–$C_3$-alkyl radicals, $C_3$–$C_6$-alkenyl, $C_5$–$C_7$-cycloalkenyl, or which in turn can carry one to three $C_1$–$C_3$-alkyl radicals, $C_3$–$C_6$-haloalkenyl, cyano-$C_1$–$C_8$-alkyl, $C_3$–$C_6$-alkynyl, $C_2$–$C_8$-alkoxyalkyl, 2-tetrahydrofuranyl-$C_1$–$C_8$-alkyl; 3-oxetanyl, 3-thietanyl, carboxyl-$C_1$–$C_6$-alkyl, ($C_1$–$C_8$-alkoxy) carbonyl-$C_1$–$C_6$-alkyl, ($C_1$–$C_6$-alkoxy)carbonyl-($C_3$–$C_7$-Cycloalkyl), $C_1$–$C_4$-alkoxy-($C_1$–$C_4$-alkoxy) carbonyl-$C_1$–$C_6$-alkyl,cyclopropylmethyl, (1-methylthiocyclopropyl)methyl, —CH(SH)—CO—OH, —CH(SH)—CO—($C_1$–$C_8$-alkoxy), —CH ($C_1$–$C_8$-alkylthio)-COOH, —CH($C_1$–$C_4$-alkylthio)-CO—($C_1$–$C_8$-alkoxy), —CH$_2$—CO—N($R^9$)—$R^{10}$, —CH($C_1$–$C_4$-alkyl)-CO—N($R^9$)—$R^{10}$, C($C_1$–$C_4$-alkyl)$_2$—CO—N($R^9$)—$R^{10}$, —CH$_2$—CO—N($R^9$)—SO$_2$—($C_1$–$C_4$-alkyl), —CH($C_1$–$C_4$-alkyl)-CO—N($R^9$)—SO$_2$—($C_1$–$C_4$-alkyl), —C($C_1$–$C_4$-alkyl)$_2$—CO—N($R^9$)—SO$_2$—($C_1$–$C_4$-alkyl), —S—CO—NH$_2$, —S—CO—N($C_1$–$C_4$-alkyl)-($C_1$–$C_4$-alkyl), —CH$_2$—CO—O—($C_1$–$C_6$-alkylene)-COOH, —CH$_2$—CO—O—($C_1$–$C_6$-alkylene)-CO—($C_1$–$C_6$-alkoxy), —C($C_1$–$C_4$-alkyl)$_2$—CO—O—($C_1$–$C_6$-alkylene)-COOH, —C($C_1$–$C_4$-alkyl)$_2$—CO—O—($C_1$–$C_4$-alkylene)-CO—($C_1$–$C_6$-alkoxy), —CH($C_1$–$C_4$-alkyl)-CO—O—($C_1$–$C_6$-alkylene)-COOH, —CH($C_1$–$C_4$-alkyl)-CO—O—($C_1$–$C_6$-alkylene)-CO—($C_1$–$C_6$-alkoxy), $C_3$–$C_9$-(α-alkylalkylidene)iminooxy-$C_1$–$C_6$-alkyl, phenyl, phenyl-$C_1$–$C_6$-alkyl, phenyl-$C_3$–$C_6$-alkenyl, phenyl-$C_3$–$C_6$-alkynyl or phenoxy-$C_1$–$C_6$-alkyl, where the phenyl ring can in each case be unsubstituted or carry one to three radicals selected from the group comprising halogen, nitro, cyano, $C_1$–$C_4$-alkyl, $C_1$–$C_4$-alkoxy, $C_1$–$C_4$-alkylthio, $C_1$–$C_4$-haloalkyl and $C_2$–$C_6$-alkenyl, 5- or 6-membered heteroaryl, heteroaryl-$C_1$–$C_6$-alkyl, heteroaryl-$C_3$–$C_6$-alkenyl, heteroaryl-$C_3$–$C_6$-alkynyl or heteroaryloxy-$C_1$–$C_6$-alkyl, where the heteroaryl radical in each case contains one to three hetero atoms selected from a group comprising one or two nitrogen atoms and one oxygen or sulfur atom, and it being possible for each heteroaromatic ring atom which can be substituted also to carry, if desired, a radical selected from the group comprising hydroxyl, halogen, $C_1$–$C_4$-alkyl, $C_1$–$C_4$-alkoxy, $C_1$–$C_4$-alkylthio and $C_1$–$C_4$-haloalkyl;

$R^9$ and $R^{10}$ independently of one another, hydrogen, $C_1$–$C_8$-alkyl, $C_2$–$C_8$-alkenyl, $C_3$–$C_8$-alkynyl, $C_1$–$C_8$-haloalkyl, $C_1$–$C_4$-alkoxy-$C_1$–$C_4$-alkyl, $C_1$–$C_4$-alkylthio-$C_1$–$C_4$-alkyl, cyano-$C_1$–$C_8$-alkyl, carboxyl-$C_1$–$C_4$-alkyl, ($C_1$–$C_4$-alkoxy)carbonyl-$C_1$–$C_4$-alkyl, ($C_1$–$C_6$-alkoxy)carbonyl-($C_3$–$C_7$-cycloalkyl), $C_1$–$C_4$-alkylsulfonyl-$C_1$–$C_4$-alkyl, $C_3$–$C_8$-cycloalkyl, $C_1$–$C_6$-alkoxy, ($C_3$–$C_6$-cycloalkoxy)carbonyl-$C_1$–$C_4$-alkyl, $C_1$–$C_4$-alkoxy-($C_1$–$C_4$-alkoxy)carbonyl-$C_1$–$C_4$-alkyl, phenyl, phenyl-$C_1$–$C_4$-alkyl, where the phenyl ring can in each case be unsubstituted or carry one to three radicals selected from the group comprising halogen, nitro, cyano, $C_1$–$C_4$-alkyl, $C_1$–$C_4$-alkoxy, $C_1$–$C_4$-alkylthio, $C_1$–$C_4$-haloalkyl and $C_2$–$C_6$-alkenyl, 5- or 6-membered heteroaryl or heteroaryl-$C_1$–$C_4$-alkyl, where the heteroaryl radical contains one to three hetero atoms selected from a group comprising one or two nitrogen atoms and one oxygen or sulfur atom, and it being possible for each heteroaromatic ring atom which can be substituted also, if desired, to carry a radical selected from the group comprising hydroxyl, halogen, $C_1$–$C_4$-alkyl, $C_1$–$C_4$-alkoxy, $C_1$–$C_4$-alkylthio and $C_1$–$C_4$-haloalkyl;

or $R^9$ and $R^{10}$ together a tetramethylene, pentamethylene or ethyleneoxyethylene chain, it being possible for each chain to carry, if desired, a ($C_1$–$C_6$-alkoxy)carbonyl radical;

$R^{11}$ hydrogen, $C_1$–$C_4$-alkyl, $C_3$–$C_6$-alkenyl, $C_3$–$C_6$-alkynyl, $C_1$–$C_4$-alkoxy-$C_1$–$C_4$-alkyl, sodium, potassium, calcium, magnesium, ammonium or ammonium which is substituted by one to four $C_1$–$C_4$-alkyl- or benzyl radicals and can, if desired, carry one to three further $C_1$–$C_4$-alkyl radicals;

$R^{12}$ hydrogen, $C_1$–$C_6$-alkyl, $C_1$–$C_6$-haloalkyl, $C_1$–$C_4$-alkoxy-$C_1$–$C_4$-alkyl, $C_3$–$C_7$-cycloalkyl, which can in turn carry one to three radicals selected from the group comprising halogen, $C_1$–$C_4$-alkyl, $C_1$–$C_4$-alkoxy and $C_1$–$C_4$-alkylthio, phenyl or phenyl-$C_1$–$C_6$-alkyl, where the phenyl ring can in each case be unsubstituted or carry one to three radicals selected from the group comprising halogen, nitro, $C_1$–$C_4$-alkyl, $C_1$–$C_4$-alkoxy, $C_1$–$C_4$-alkylthio and $C_1$–$C_4$-haloalkyl;

$R^{13}$ and $R^{14}$, independently of one another, $C_1$–$C_4$-alkyl, phenyl or thienyl, where the phenyl or thienyl radical can be unsubstituted or carry one to three radicals selected from the group comprising halogen, nitro, $C_1$–$C_4$-alkyl, $C_1$–$C_4$-alkoxy, $C_1$–$C_4$-alkylthio and $C_1$–$C_4$-haloalkyl;

$R^{15}$, $R^{16}$ and $R^{17}$, independently of one another, hydrogen, halogen, $C_1$–$C_4$-alkyl, $C_2$–$C_4$-alkenyl, $C_1$–$C_4$-haloalkyl, $C_1$–$C_4$-alkoxy-$C_1$–$C_4$-alkyl or $C_1$–$C_4$-alkylthio-$C_1$–$C_4$-alkyl;

$R^{18}$ and $R^{19}$, independently of one another, $C_1$–$C_8$-alkyl, $C_1$–$C_4$-alkoxy-$C_1$–$C_4$-alkyl or $C_1$–$C_8$-haloalkyl;

$R^{20}$, $R^{21}$, $R^{22}$, $R^{23}$, $R^{24}$ and $R^{25}$, independently of one another, hydrogen, cyano, $C_1$–$C_8$-alkyl, $C_1$–$C_4$-alkoxy-$C_1$–$C_4$-alkyl, halo-$C_1$–$C_8$-alkyl, $C_1$–$C_8$-alkoxy, $C_1$–$C_4$-alkoxy-$C_1$–$C_4$-alkoxy, —CO—O—$R^8$, —CO—N($R^9$, $R^{10}$), —CO—$R^{15}$, —S—$R^8$, —SO$_2$—$R^8$, —O—CO—$R^{12}$ or $C_3$–$C_7$-cycloalkyl, which can in turn carry from one to three radicals selected from the group comprising halogen, $C_1$–$C_4$-alkyl, $C_1$–$C_4$-alkoxy and $C_1$–$C_4$-alkylthio;

$R^{26}$ $C_1$–$C_6$-alkyl, $C_1$–$C_6$-alkylthio, $C_1$–$C_6$-alkoxycarbonyl or $C_1$–$C_6$-alkoxycarbonyl-$C_1$–$C_4$-alkyl;

$R^{27}$ $C_1$–$C_6$-alkyl, trifluoromethyl, $C_1$–$C_6$-alkoxy-$C_1$–$C_4$-alkyl, $C_2$–$C_7$-alkoxycarbonyl-$C_1$–$C_4$-alkyl, di-($C_1$–$C_6$-alkoxycarbonyl)-$C_1$–$C_4$-alkyl, $C_3$–$C_6$-cycloalkyl, $C_1$–$C_6$-alkoxy, $C_1$–$C_6$-alkylthio, $C_1$–$C_6$-alkanoyl, $C_1$–$C_6$-alkoxycarbonyl, 2-furyl or phenyl which can be unsubstituted or in turn carry one to three radicals selected from the group comprising halogen, $C_1$–$C_4$-alkyl and $C_1$–$C_4$-alkoxy;

or $R^{26}$ and $R^{27}$ together with the carbon to which they are bonded a cyclopentane or cyclohexane ring which can in turn, if desired, carry one to three $C_1$–$C_4$-alkyl radicals;

$R^{28}$ hydrogen or $C_1$–$C_4$-alkyl;

$R^{29}$ hydrogen, $C_1$–$C_4$-alkyl, phenyl or benzyl;

$R^{30}$ hydrogen or $C_1$–$C_6$-alkyl;

$R^{31}$ $C_1$–$C_6$-alkyl, $C_3$–$C_6$-cycloalkyl or phenyl;

X and Y, independently of one another, oxygen or sulfur;

and the N-oxides of I and the agriculturally utilizable salts of I where these exist, excepting those compounds I where $R^2$ is $C_1$–$C_4$-alkoxy and $R^1$ and/or $R^3$ is carboxyl, its salt, ester or amide.

The invention furthermore relates to
- the use of the compounds I, their N-oxides and/or agriculturally utilizable salts, as herbicides and for the desiccation and/or defoliation of plants,
- herbicidal compositions and compositions for the desiccation and/or defoliation of plants, which contain the compounds I, their N-oxides and/or agriculturally utilizable salts, as active substances,
- processes for the production of these herbicidal compositions and compositions for the desiccation and/or defoliation of plants, methods for controlling unwanted plant growth and for the desiccation and/or defoliation of plants using the compounds I or compounds I' where I' corresponds to the formula I without the disclaimer and $R^4$ may additionally be aminocarbonyl, ($C_1$–$C_4$-alkyl)aminocarbonyl, di-($C_1$–$C_4$-alkyl)aminocarbonyl, pyrrolidinylcarbonyl, piperidinylcarbonyl or morpholinylcarbonyl, as well as the N-oxides and the agriculturally utilizable salts of I and I', and
- processes for the preparation of the compounds I.

The invention additionally relates to the use of phenylpyridines of the formula IV

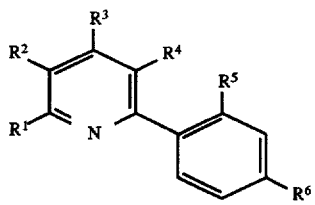

and of aromatic boronic acids or esters thereof of the formula IIIa

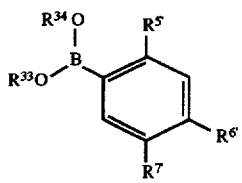

where $R^{5'}$ is hydrogen, fluorine or chlorine;

$R^{6'}$ is halogen, hydroxyl or $C_1$–$C_4$-alkoxy;

$R^{7'}$ is hydrogen, $C_1$–$C_4$-alkyl or $C_1$–$C_4$-alkoxy;

$R^{33}$ and $R^{34}$ are, independently of one another, hydrogen or $C_1$–$C_4$-alkyl or together are ethylene or propylene, as intermediates for the preparation of the substituted 2-phenylpyridines I and to novel aromatic boronic acids and esters thereof of the formula IIIa'

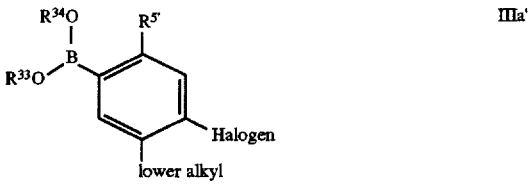

where $R^{5'}$ is hydrogen, fluorine or chlorine;

halogen is a halogen atom;

lower alkyl is $C_1$–$C_4$-alkyl and $R^{33}$ and $R^{34}$ are, independently of one another, hydrogen or $C_1$–$C_4$-alkyl or together are ethylene or propylene.

Some 2-phenylpyridines have previously been disclosed in the following publications: EP-A 412 681; WO 94/05153; WO 94/10118; WO 92/22203; CA 114(11), 96724k; Izv. Timiryazevsk. S-Kh. Akad. 3, 155–160; Pestic. Sci. 21(3), 175–179.

Highly fluorinated 2-phenylpyridines are provided as intermediates for drugs and agrochemicals in T. Konakahara et al., Nippon Kagaku Kaishi, (5), 466–71 {CA 113 (19): 171 837 j} and der JP 12 11 586:

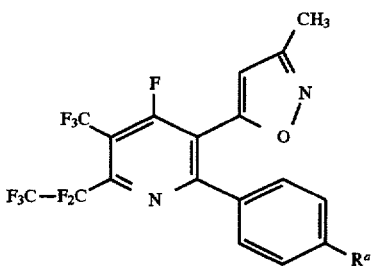

where $R^a$ is hydrogen, dimethylamino, chlorine, methoxy or methyl.

EP-A 167 491 discloses substituted thiobarbituric acids, eg.

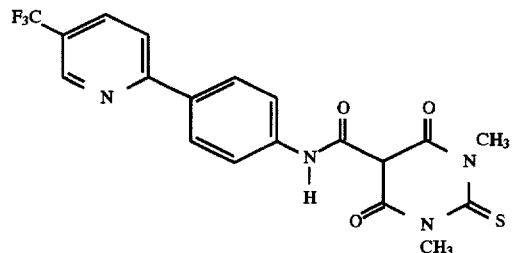

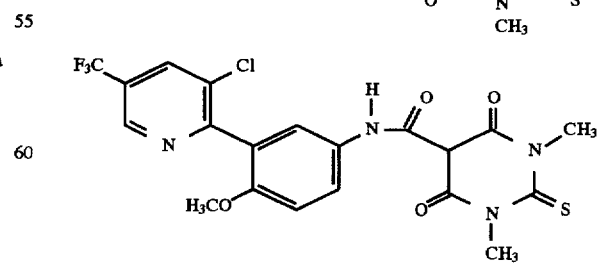

P. Boy et al. (Synlett 12, 923) disclose the preparation of 4-[(trifluoromethyl)pyridyl]phenols:

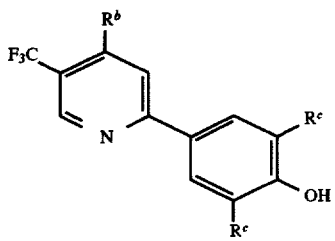

$R^b$=hydrogen or trifluoromethyl; $R^c$=hydrogen or tert-butyl.

N. Katagiri et al. (Chem. Pharm. Bull. 36 (9), 3354–72) describe the preparation of substituted 2-phenylpyridines:

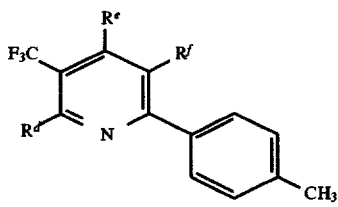

where $R^d$ is hydrogen, chlorine or methoxy, $R^e$ is hydrogen, methyl, ethyl or ethoxy and $R^f$ is hydrogen or methyl or $R^e$ and $R^f$ together are $(CH_2)_3$ or $(CH_2)_4$.

Finally, DE-A 40 20 257 discloses 2,6-diarylpyridine derivatives with herbicidal and defoliating properties:

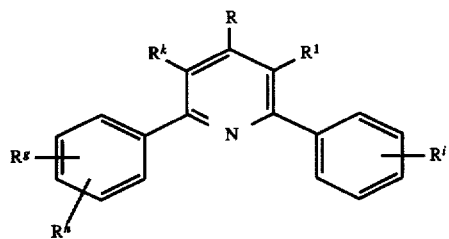

where $R^g$ and $R^h$ are hydrogen, halogen, alkyl, alkoxy or haloalkyl, $R^i$ is hydrogen, halogen, cyano, alkyl, alkoxy or haloalkyl and $R^k$ and $R^l$ are hydrogen or alkyl.

Those known compounds which in fact have a herbicidal, defoliating, pesticidal or fungicidal action are not always completely satisfactory.

It was an object of the present invention to provide novel compounds which have, in particular, herbicidal activity and which can be used for the targeted control of unwanted plants better than hitherto.

Accordingly, we have found that this object is achieved by the present substituted 2-phenylpyridines of the formula I and the compounds I'. We have also found herbicidal compositions which contain the compounds I and have a good herbicidal action. They are tolerated or selective, preferably in graminaceous crops such as wheat, corn and rice.

We have also found processes for the production of these herbicidal compositions. We have additionally found novel intermediates of the formula IIIa' for preparing the substituted 2-phenylpyridines I.

The compounds I and I' according to the invention are furthermore suitable for the defoliation and desiccation of parts of plants for, for example, cotton, potato, rape, sunflower, soybean or broad beans.

The organic moieties specified above for the substituents $R^1$ to $R^{34}$ or as substituents on (hetero)aromatic radicals represent, like the meaning of halogen, collective terms for individual lists of the individual group members. All the carbon chains, ie. all alkyl, alkenyl, alkynyl, haloalkyl, haloalkenyl, haloalkynyl and haloalkoxy moieties and the α-alkylalkylidene moiety, can be straight-chain or branched. Halogenated substituents preferably have one to five identical or different halogen atoms.

Examples of specific meanings are:

Halogen: fluorine, chlorine, bromine and iodine, preferably fluorine and chlorine;

$C_1$–$C_4$-Alkyl: methyl, ethyl, n-propyl, 1-methylethyl, n-butyl, 1-methylpropyl, 2-methylpropyl and 1,1-dimethylethyl;

$C_1$–$C_6$-Alkyl: $C_1$–$C_4$-alkyl as mentioned above, and n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$–$C_8$-Alkyl: $C_1$–$C_6$-alkyl as mentioned above, and, inter alia, n-heptyl, n-octyl;

$C_2$–$C_4$-Alkenyl: ethenyl, prop-1-en-1-yl, prop-2-en-1-yl, 1-methylethenyl, n-buten-1-yl, n-buten-2-yl, n-buten-3-yl, 1-methyl-prop-1-en-1-yl, 2-methyl-prop-1-en-1-yl, 1-methyl-prop-2-en-1-yl and 2-methyl-prop-2-en-1-yl;

$C_3$–$C_6$-Alkenyl: prop-1-en-1-yl, prop-2-en-1-yl, 1-methylethenyl, n-buten-1-yl, n-buten-2-yl, n-buten-3-yl, 1-methyl-prop-1-en-1-yl, 2-methyl-prop-1-en-1-yl, 1-methyl-prop-2-en-1-yl, 2-methyl-prop-2-en-1-yl, n-penten-1-yl, n-penten-2-yl, n-penten-3-yl, n-penten-4-yl, 1-methyl-but-1-en-1-yl, 2-methyl-but-1-en-1-yl, 3-methyl-but-1-en-1-yl, 1-methyl-but-2-en-1-yl, 2-methyl-but-2-en-1-yl, 3-methyl-but-2-en-1-yl, 1-methyl-but-3-en-1-yl, 2-methyl-but-3-en-1-yl, 3-methyl-but-3-en-1-yl, 1,1-dimethyl-prop-2-en-1-yl, 1,2-dimethyl-prop-1-en-1-yl, 1,2-dimethyl-prop-2-en-1-yl, 1-ethyl-prop-1-en-2-yl, 1-ethyl-prop-2-en-1-yl, n-hex-1-en-1-yl, n-hex-2-en-1-yl, n-hex-3-en-1-yl, n-hex-4-en-1-yl, n-hex-5-en-1-yl, 1-methyl-pent-1-en-1-yl, 2-methyl-pent-1-en-1-yl, 3-methyl-pent-1-en-1-yl, 4-methyl-pent-1-en-1-yl, 1-methyl-pent-2-en-1-yl, 2-methyl-pent-2-en-1-yl, 3-methyl-pent-2-en-1-yl, 4-methyl-pent-2-en-1-yl, 1-methyl-pent-3-en-1-yl, 2-methyl-pent-3-en-1-yl, 3-methyl-pent-3-en-1-yl, 4-methyl-pent-3-en-1-yl, 1-methyl-pent-4-en-1-yl, 2-methyl-pent-4-en-1-yl, 3-methyl-pent-4-en-1-yl, 4-methyl-pent-4-en-1-yl, 1,1-dimethyl-but-2-en-1-yl, 1,1-dimethyl-but-3-en-1-yl, 1,2-dimethyl-but-1-en-1-yl, 1,2-dimethyl-but-2-en-1-yl, 1,2-dimethyl-but-3-en-1-yl, 1,3-dimethyl-but-1-en-1-yl, 1,3-dimethyl-but-2-en-1-yl, 1,3-dimethyl-but-3-en-1-yl, 2,2-dimethyl-but-3-en-1-yl, 2,3-dimethyl-but-1-en-1-yl, 2,3-dimethyl-but-2-en-1-yl, 2,3-dimethyl-but-3-en-1-yl, 3,3-dimethyl-but-1-en-1-yl, 3,3-dimethyl-but-2-en-1-yl, 1-ethyl-but-1-en-1-yl, 1-ethyl-but-2-en-1-yl, 1-ethyl-but-3-en-1-yl, 2-ethyl-but-1-en-1-yl, 2-ethyl-but-2-en-1-yl, 2-ethyl-but-3-en-1-yl, 1,1,2-trimethylprop-2-en-1-yl, 1-ethyl-1-methyl-prop-2-en-1-yl, 1-ethyl-2-methyl-prop-1-en-1-yl and 1-ethyl-2-methyl-prop-2-en-1-yl, preferably ethenyl and prop-2-en-1-yl;

$C_2$–$C_8$-Alkenyl: ethenyl, $C_3$–$C_6$-alkenyl as mentioned above and, inter alia, n-hept-1-en-1-yl, n-hept-2-en-1- yl, n-hept-3-en-1-yl, n-hept-4-en-1-yl, n-hept-5-en-1-yl, n-hept-6-en-1-yl, n-oct-1-en-1-yl, n-oct-2-en-1-yl, n-oct-3-en-1-yl, n-oct-4-en-1-yl, n-oct-5-en-1-yl, n-oct-6-en-1-yl and n-oct-7-en-1-yl;

$C_2$–$C_6$-Alkynyl: ethynyl and $C_3$–$C_6$-alkynyl such as prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-1-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methyl-pent-1-yn-3-yl, 3-methyl-pent-1-yn-4-yl, 3-methyl-pent-1-yn-5-yl, 4-methyl-pent-1-yn-1-yl, 4-methyl-pent-2-yn-4-yl and 4-methyl-pent-2-yn-5-yl, preferably prop-2-yn-1-yl and 1-methyl-prop-2-yn-1-yl;

$C_2$–$C_8$-Alkynyl: ethynyl, $C_3$–$C_6$-Alkynyl as mentioned above and, inter alia, n-hept-1-yn-1-yl, n-hept-2-yn-1-yl, n-hept-3-yn-1-yl, n-hept-4-yn-1-yl, n-hept-5-yn-1-yl, n-hept-6-yn-1-yl, n-oct-1-yn-1-yl, n-oct-2-yn-1-yl, n-oct-3-yn-1-yl, n-oct-4-yn-1-yl, n-oct-5-yn-1-yl, n-oct-6-yn-1-yl and n-oct-7-yn-1-yl;

$C_3$–$C_6$-Haloalkenyl: $C_3$–$C_6$-alkenyl as mentioned above with in each case one to three hydrogen atoms being replaced by fluorine, chlorine and/or bromine;

$C_2$–$C_8$-Haloalkenyl: $C_2$–$C_8$-alkenyl as mentioned above with in each case one to three hydrogen atoms being replaced by fluorine, chlorine and/or bromine;

$C_2$–$C_8$-Halolkynyl: $C_2$–$C_8$-alkynyl as mentioned above with in each case one to three hydrogen atoms being replaced by fluorine, chlorine and/or bromine;

$C_3$–$C_6$-Cycloalkyl: cyclopropyl, cyclobutyl, cyclopentyl and cyclohexyl, preferably cyclopropyl, cylopentyl and cyclohexyl;

$C_4$–$C_7$-Cycloalkyl: cyclobutyl, cyclopentyl, cyclohexyl and cycloheptyl, preferably cylopentyl and cyclohexyl;

$C_5$–$C_7$-Cycloalkenyl eg.: cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl and cyclohept-4-enyl;

($C_3$–$C_6$-Cycloalkoxy)carbonyl: cyclopropoxycarbonyl, cyclobutoxycarbonyl, cyclopentoxycarbonyl and cyclohexoxycarbonyl, preferably cyclopropoxycarbonyl, cyclopentoxycarbonyl and cyclohexoxycarbonyl;

$C_1$–$C_4$-Haloalkyl: $C_1$–$C_4$-alkyl as mentioned above, which is partially or completely substituted by fluorine, chlorine and/or bromine eg. chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluoromethyl;

$C_1$–$C_6$-Haloalkyl: $C_1C_6$-alkyl as mentioned above, which is partially or completely substituted by fluorine, chlorine and/or bromine;

$C_1$–$C_8$-Haloalkyl: $C_1$–$C_8$-alkyl as mentioned above, which is partially or completely substituted by fluorine, chlorine and/or bromine eg. the abovementioned $C_1$–$C_4$-haloalkyls;

Cyano-$C_1$–$C_8$-alkyl: $C_1$–$C_8$-alkyl as mentioned above, with in each case one hydrogen atom being replaced by the cyano group, eg. cyanomethyl, 1-cyanoeth-1-yl, 2-cyanoeth-1-yl, 1-cyano-prop-1-yl, 2-cyano-prop-1-yl, 3-cyano-prop-1-yl, 1-cyano-prop-2-yl, 2-cyano-prop-2-yl, 1-cyano-but-1-yl, 2-cyano-but-1-yl, 3-cyano-but-1-yl, 4-cyano-but-1-yl, 1-cyano-but-2-yl, 2-cyano-but-2-yl, 1-cyano-but-3-yl, 2-cyano-but-3-yl, 1-cyano-2-methyl-prop-3-yl, 2-cyano-2-methyl-prop-3-yl, 3-cyano-2-methyl-prop-3-yl, and 2-cyanomethyl-prop-2-yl, preferably cyanomethyl and 1-cyano-1-methylethyl;

Phenyl-$C_1$–$C_4$-alkyl: $C_1$–$C_4$-alkyl as mentioned above, with in each case one hydrogen atom being replaced by the phenyl group, eg. benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 3-phenylbut-2-yl, 4-phenylbut-2-yl, 1-(phenylmethyl)-eth-1-yl, 1-(phenylmethyl)-1-(methyl)-eth-1-yl and 1-(phenylmethyl)-prop-1-yl, preferably benzyl;

Phenyl-$C_1$–$C_6$-alkyl: $C_1$–$C_6$-alkyl as mentioned above, with in each case a hydrogen atom being replaced by the phenyl group, eg. the abovementioned phenyl-$C_1$–$C_4$-alkyls;

Phenyl-$C_3$–$C_6$-alkenyl: $C_3$–$C_6$-alkenyl as mentioned above, with one hydrogen atom in each case being replaced by the phenyl group;

Phenyl-$C_3$–$C_6$-alkynyl: $C_3$–$C_6$-alkynyl as mentioned above, with one hydrogen atom in each case being replaced by the phenyl group;

$C_1$–$C_4$-Alkoxy: methoxy, ethoxy, n-propoxy, 1-methylethoxy, n-butoxy, 1-methylpropoxy, 2-methylpropoxy and 1,1-dimethylethoxy, preferably methoxy, ethoxy and 1-methylethoxy;

$C_1$–$C_6$-Alkoxy: $C_1$–$C_4$-alkoxy as mentioned above, and n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_8$-Alkoxy: $C_1$–$C_6$-alkoxy as mentioned above, and, for example, n-heptoxy and n-octoxy;

$C_1$–$C_4$-Haloalkoxy: $C_1$–$C_4$-alkoxy as mentioned above, which is partially or completely substituted by fluorine, chlorine and/or bromine, eg. chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, preferably $C_1$–$C_2$-haloalkoxy such as trifluoromethoxy;

$C_1$–$C_4$-Alkylthio: methylthio, ethylthio, n-propylthio, 1-methylethylthio, n-butylthio, 1-methyl-propylthio, 2-methylpropylthio and 1,1-dimethylethylthio, preferably methylthio, ethylthio and methylethylthio;

$C_1$–$C_4$-Haloalkylthio: chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio, preferably $C_1$–$C_2$-haloalkylthio such as trifluoromethylthio;

$C_3$–$C_6$-Alkenyloxy: prop-1-en-1-yloxy, prop-2-en-1-yloxy, 1-methylethenyloxy, n-buten-1-yloxy, n-buten-2-yloxy, n-buten-3-yloxy, 1-methyl-prop-1-en-1-yloxy, 2-methyl-prop-1-en-1-yloxy, 1-methyl-prop-2-en-1-yloxy, 2-methyl-prop-2-en-1-yloxy, n-penten-1-yloxy, n-penten-2-yloxy, n-penten-3-yloxy, n-penten-4-yloxy, 1-methyl-but-1-en-1-yloxy, 2-methyl-but-1-en-1-yloxy, 3-methyl-but-1-en-1-yloxy, 1-methyl-but-2-en-1-yloxy, 2-methyl-but-2-en-1-yloxy, 3-methyl-but-2-en-1-yloxy, 1-methyl-but-3-en-1-yloxy, 2-methyl-but-3-en-1-yloxy, 3-methyl-but-3-en-1-yloxy, 1,1-dimethyl-prop-2-en-1-yloxy, 1,2-dimethyl-prop-1-en-1-yloxy, 1,2-dimethyl-prop-2-en-1-yloxy, 1-ethyl-prop-1-en-2-yloxy, 1-ethyl-prop-2-en-1-yloxy, n-hex-1-en-1-yloxy, n-hex-2-en-1-yloxy, n-hex-3-en-1-yloxy, n-hex-4-en-1-yloxy, n-hex-5-en-1-yloxy, 1-methyl-pent-1-en-1-yloxy, 2-methyl-pent-1-en-1-yloxy, 3-methyl-pent-1-en-1-yloxy, 4-methyl-pent-1-en-1-yloxy, 1-methyl-pent-2-en-1-yloxy, 2-methyl-pent-2-en-1-yloxy, 3-methyl-pent-2-en-1-yloxy, 4-methyl-pent-2-en-1-yloxy, 1-methyl-pent-3-en-1-yloxy, 2-methyl-pent-3-en-1-yloxy, 3-methyl-pent-3-en-1-yloxy, 4-methyl-pent-3-en-1-yloxy, 1-methyl-pent-4-en-1-yloxy, 2-methyl-pent-4-en-1-yloxy, 3-methyl-pent-4-en-1-yloxy, 4-methyl-pent-4-en-1-yloxy, 1,1-dimethyl-but-2-en-1-yloxy, 1,1-dimethyl-but-3-en-1-yloxy, 1,2-dimethyl-but-1-en-1-yloxy, 1,2-dimethyl-but-2-en-1-yloxy,1,2-dimethyl-but-3-en-1-yloxy, 1,3-dimethyl-but-1-en-1-yloxy, 1,3-dimethyl-but-2-en-1-yloxy, 1,3-dimethyl-but-3-en-1-yloxy, 2,2-dimethyl-but-3-en-1-yloxy, 2,3-dimethyl-but-1-en-1-yloxy, 2,3-dimethyl-but-2-en-1-yloxy, 2,3-dimethyl-but-3-en-1-yloxy, 3,3-dimethyl-but-1-en-1-yloxy, 3,3-dimethyl-but-2-en-1-yloxy, 1-ethyl-but-1-en-1-yloxy, 1-ethyl-but-2-en-1-yloxy, 1-ethyl-but-3-en-1-yloxy, 2-ethyl-but-1-en-1-yloxy, 2-ethyl-but-2-en-1-yloxy, 2-ethyl-but-3-en-1-yloxy, 1,1,2-trimethylprop-2-en-1-yloxy, 1-ethyl-1-methyl-prop-2-en-1-yloxy, 1-ethyl-2-methyl-prop-1-en-1-yloxy and 1-ethyl-2-methyl-prop-2-en-1-yloxy, preferably ethenyloxy and prop-2-en-1-yloxy;

Phenoxy-$C_1$–$C_4$-alkyl: phenoxymethyl, 1-phenoxyethyl, 2-phenoxyethyl, 1-phenoxyprop-1-yl, 2-phenoxyprop-1-yl, 3-phenoxyprop-1-yl, 1-phenoxybut-1-yl, 2-phenoxybut-1-yl, 3-phenoxybut-1-yl, 4-phenoxybut-1-yl, 1-phenoxybut-2-yl, 2-phenoxybut-2-yl, 3-phenoxybut-2-yl, 4-phenoxybut-2-yl, 1-(phenoxymethyl)-eth-1-yl, 1-(phenoxymethyl)-1-(methyl)-eth-1-yl and 1-(phenoxymethyl)-prop-1-yl, preferably phenoxymethyl;

$C_1$–$C_4$-Alkylamino: methylamino, ethylamino, n-propylamino, 1-methylethylamino, n-butylamino, 1-methylpropylamino, 2-methylpropylamino and 1,1-dimethylethylamino, preferably methylamino and ethylamino;

Di-($C_1$–$C_4$-alkyl)amino: N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methyl-propyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino, preferably dimethylamino and diethylamino;

$C_1$–$C_4$-Alkylaminocarbonyl: methylaminocarbonyl, ethylaminocarbonyl, n-propylaminocarbonyl, 1-methylethylaminocarbonyl, n-butylaminocarbonyl, 1-methylpropylaminocarbonyl, 2-methylpropylaminocarbonyl and 1,1-dimethylethylaminocarbonyl, preferably methylaminocarbonyl and ethylaminocarbonyl;

Di-($C_1$–$C_4$-alkyl)aminocarbonyl: N,N-dimethylaminocarbonyl, N,N-diethylaminocarbonyl, N,N-dipropylaminocarbonyl, N,N-di-(1-methylethyl)aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1methylpropyl)aminocarbonyl, N-methyl-N-(2-methyl-prop)aminocarbonly, N-(1,1-dimethylethyl)-N-methylaminocarbonyl, N-ethyl-N-propylaminocarbonyl, N-ethyl-N-(1-methylethyl)aminocarbonly, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methyl-ethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl and N-(1,1-dimethylethyl)-N-(2-methylpropyl) aminocarbonyl, preferably dimethylaminocarbonyl and diethylaminocarbonyl;

$C_1$–$C_4$-Alkylsulfonyl: methylsulfonyl, ethylsulfonyl, n-propylsulfonyl, 1-methylethyl-sulfonyl, n-butylsulfonyl, 1-methylpropylsulfonyl, 2-methylpropylsulfonyl and 1,1-dimethylethylsulfonyl;

$C_1$–$C_4$-Alkylsulfinyl: methylsulfinyl, ethylsulfinyl, n-propylsulfinyl, 1-methylethyl-sulfinyl, n-butylsulfinyl, 1-methylpropylsulfinyl, 2-methylpropylsulfinyl and 1,1-dimethylethylsulfinyl;

$C_1$–$C_4$-Alkylsulfonylamino: methylsulfonylamino, ethylsulfonylamino, n-propylsulfonylamino, 1-methylethyl-sulfonylamino, n-butylsulfonylamino, 1-methylpropylsulfonylamino, 2-methylpropylsulfonylamino and 1,1-dimethylethylsulfonylamino;

$C_1$–$C_4$-Haloalkylsulfonyl: $C_1$–$C_4$-alkylsulfonyl as mentioned above, which is partially or completely substituted by fluorine, chlorine and/or bromine, eg. chloromethylsulfonyl, dichloromethylsulfonyl, trichloromethylsulfonyl, fluoromethylsulfonyl, difluoromethylsulfonyl, trifluoromethylsulfonyl, chlorofluoromethylsulfonyl, dichlorofluoromethylsulfonyl, chlorodifluoromethylsulfonyl, 1-fluoroethylsulfonyl, 2-fluoroethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2 2,2-trichloroethylsulfonyl and pentafluoroethylsulfonyl, preferably trichloromethylsulfonyl and trifluoromethylsulfonyl;

$C_1$–$C_4$-Haloalkylsulfinyl: $C_1$–$C_4$-alkylsulfinyl as mentioned above, which is partially or completely substituted by fluorine, chlorine and/or bromine, eg. chloromethylsulfinyl, dichloromethylsulfinyl, trichloromethylsulfinyl, fluoromethylsulfinyl, difluoromethylsulfinyl, trifluoromethylsulfinyl, chlorofluoromethylsulfinyl, dichlorofluoromethylsulfinyl, chlorodifluoromethylsulfinyl, 1-fluoroethylsulfinyl, 2-fluoroethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl and pentafluoroethylsulfinyl, preferably trichloromethylsulfinyl and trifluoromethylsulfinyl;

$C_3$–$C_9$-($\alpha$-Alkylalkylidene) iminooxy eg.:
$\alpha$-methylethylideneiminooxy and $\alpha$-methylpropylideneiminooxy;

Suitable meanings for 5- or 6-membered heteroaryl and heteroaryl-$C_1$–$C_4$-alkyl are the following heteroaromatics: 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Particularly suitable agriculturally utilizable cations are those which do not adversely affect the herbicidal action of the compounds I, in particular the ions of the alkali metals, preferably sodium and potassium, of the alkaline earth metals, preferably calcium, magnesium and barium, and of the transition metals, preferably zinc and iron, and the ammonium ion which can, if desired, carry one to three $C_1$–$C_4$-alkyl, hydroxy-$C_1$–$C_4$-alkyl substituents and/or one phenyl or benzyl substituent, preferably diisopropylammonium, tetramethylammonium, tetrabutylammonium, trimethylbenzylammonium and trimethyl-(2-hydroxyethyl) -ammonium, tri-($C_1$–$C_4$-alkyl) sulfonium, and sulfoxonium ions, preferably tri-($C_1$–$C_4$-alkyl)sulfoxonium.

The ammonium ion and the abovementioned substituted ammonium ions are very particularly preferred cations.

With a view to the use of the substituted 2-phenylpyridines I and I' as herbicides or desiccant/defoliant compounds, the preferred substituted 2-phenylpyridines I and I' are those in which the substituents have the following meanings, in each case alone or in combination:

$R^1$ hydrogen, methyl, methoxy, methylthio or halogen, very particularly preferably hydrogen;

$R^2$ halogen, $C_1$–$C_4$-haloalkyl with one to five halogen atoms or $C_1$–$C_4$-haloalkoxy with one to five halogen atoms, very particularly preferably trifluoromethyl;

$R^3$ hydrogen, methyl, methoxy, methylthio or halogen;

$R^4$ methyl, methoxy, methylthio or halogen, very particularly preferably halogen;

$R^5$ hydrogen, fluorine or chlorine;

$R^6$ chlorine and $R^7$ —O—$R^8$, —S—$R^8$, —SO$_2$—N($R^9$,$R^{10}$), —NR$^{11}$(SO$_2$—$R^{13}$), —CO—O—$R^8$, —CR$^{15}$=C($R^{16}$)—CO—O—$R^8$, —CH=N—O—$R^8$, —CH($XR^{18}$, $YR^{19}$), —CH$_2$—CH(Cl)—CO—O—$R^8$,

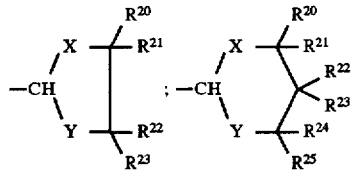

The substituted 2-phenylpyridines of the formula I can be obtained in a variety of ways, preferably by one of the following processes:

Reaction of a substituted 2-halopyridine II with an organometallic compound III in the presence of a transition metal catalyst in an inert solvent:

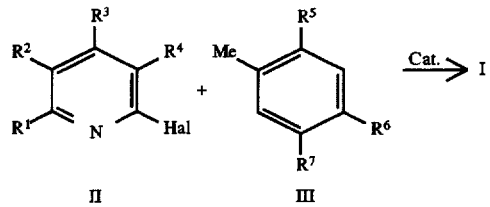

In this case, Hal is chlorine or bromine, Me is Mg—Hal, Zn—Hal, tri-($C_1$–$C_4$-alkyl)tin, lithium, copper or B(OR$^{32}$)(OR$^{33}$), where $R^{32}$ and $R^{33}$ are, independently of one another, hydrogen or $C_1$–$C_4$-alkyl, and Cat. is a transition metal catalyst, in particular a palladium catalyst such as tetrakis(triphenylphosphine)- palladium(O), bis(1,4-diphenylphosphino)butanepalladium(II) chloride and bis (triphenylphosphine)palladium(II) chloride, or a nickel catalyst such as nickel(II) acetylacetonate, bis (triphenylphosphine)nickel(II) chloride and bis(1,3-diphenylphosphino)propanenickel(II) chloride.

Me is preferably B(OR$^{32}$)(OR$^{33}$). Reactions of this type are generally known, for example from the following literature:

Reactions with boronic acids (Me=B(OR$^{32}$)(OR$^3$)):

(1) W. J. Thompson and J. Gaudino, J. Org. Chem. 49 (1984) 5237;

(2) S. Gronowitz and K. Lawitz, Chem. Scr. 24 (1984) 5;
(3) S. Gronowitz et al., Chem. Scr. 26 (1986) 305;
(4) J. Stavenuiter et al., Heterocycles 26 (1987) 2711;
(5) V. Snieckus et al., Tetrahedron Letters 28 (1987) 5093;
(6) V. Snieckus et al., Tetrahedron Letters 29 (1988) 2135;
(7) M. B. Mitchell et al., Tetrahedron Letters 32 (1991) 2273; Tetrahedron 48 (1992) 8117;
(8) JP-A 93/301 870;

Reactions with Grignard compounds (Me=Mg-Hal):
(9) L. N. Pridgen, J. Heterocyclic Chem., 12 (1975) 443;
(10) M. Kumada et al., Tetrahedron Letters, 21 (1980) 845, ibid 22 (1981) 5319;
(11) A. Minato et al., J. Chem. Soc., Chem. Commun., (1984) 511;

Reactions with organozinc compounds (Me=Zn-Hal):
(12) A. S. Bell et al., Synthesis, (1987) 843;
(13) A. S. Bell et al., Tetrahedron Letters, 29 (1988) 5013;
(14) J. W. Tilley and S. Zawoiski, J. Org. Chem. 53 (1988) 386, see also Lit. (9);

Reactions with organotin compounds {Me=Sn(C$_1$-C$_8$-alkyl)$_3$}:
(15) T. R. Bailey et al., Tetrahedron Letters, 27 (1986) 4407;
(16) Y. Yamamoto et al., Synthesis, 1986, 564; see also Lit. (6).

With a view to the preferred active substances I, the 2-halopyridines II are preferably reacted with an aromatic boronic acid of the formula IIIa

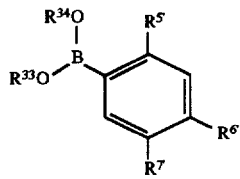

where
R$^{5'}$ is hydrogen, fluorine or chlorine;
R$^{6'}$ is hydroxyl, halogen or C$_1$-C$_4$-alkoxy;
R$^{7'}$ is hydrogen, C$_1$-C$_4$-alkyl or C$_1$-C$_4$-alkoxy and
R$^{33}$ and R$^{34}$ are, independently of one another, hydrogen or C$_1$-C$_4$-alkyl or together are ethylene or propylene.

Among the boronic acids and esters thereof of the formula IIIa, those of the formula IIIa'

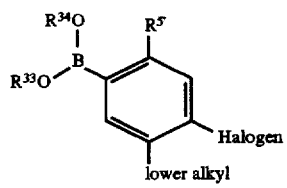

where
R$^{5'}$ is hydrogen, fluorine or chlorine;
halogen is a halogen atom;
lower alkyl is C$_1$-C$_4$-alkyl and
R$^{33}$ and R$^{34}$ are, independently of one another, hydrogen or
C$_1$-C$_4$-alkyl or together are ethylene or propylene, are novel.

The coupling of II+III may, where appropriate, be followed by reactions on the phenyl ring to obtain further derivatives of the compounds I.

The compounds I can be converted by conventional methods, eg. by reaction with an organic peracid such as metachloroperbenzoic acid, into the N-oxides.

Substituted 2-phenylpyridines I where R$^1$, R$^3$ and/or R$^4$ are an alkali metal carboxylate radical can be obtained by treating compounds I with R$^1$, R$^3$ and/or R$^4$=hydroxycarbonyl for example
with sodium or potassium hydroxide in aqueous solution or an organic solvent such as methanol, ethanol, acetone or toluene or
with sodium hydride in an organic solvent such as dimethylformamide.

The salt formation normally takes place at a sufficient rate at about 20° C.

The salt can be isolated, for example, by a precipitation with a suitable inert solvent or by evaporating off the solvent.

Substituted 2-phenylpyridines I where R$^1$, R$^3$ and/or R$^4$ is a carboxylate radical whose counterion is an agriculturally utilizable cation not belonging to the group of alkali metals can normally be prepared by metathesis of the corresponding alkali metal carboxylates.

Compounds I where R$^1$, R$^3$ and/or R$^4$ is a carboxylate radical whose counterion is, for example, a zinc, iron, calcium, magnesium or barium ion can be prepared from the corresponding sodium carboxylates in a conventional way, as can compounds I where R$^1$, R$^3$ and/or R$^4$ is a carboxylate radical whose counterion is an ammonium or phosphonium ion, using ammonia, phosphonium, sulfonium or sulfoxonium hydroxides.

Unless otherwise indicated, all the reactions described above are expediently carried out under atmospheric pressure or the autogenous pressure of the particular reaction mixture.

The substituted 2-phenylpyridines I may result from the prepararation as mixtures of isomers which, however, can if desired be separated by the methods conventional for this purpose, such as crystallization or chromatography, also on an optically active adsorbate, into the pure isomers. Pure optically active isomers can advantageously be prepared from corresponding optically active starting materials.

The substituted 2-phenylpyridines I and I', their agriculturally utilizable salts and N-oxides are suitable, both as mixtures of isomers and in the form of the pure isomers, as herbicides. They are able to control weeds and obnoxious grasses very efficiently in crops such as wheat, rice, corn, soybean and cotton with negligible damage to the crop plants. This effect occurs, in particular, with low application rates.

Depending on the particular application method, the compounds I and I' or the herbicidal compositions containing them can also be employed in a further number of crop plants to eliminate unwanted plants. Examples of suitable crops are the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum (N.*

*rustica), Olea europaea, oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* und *Zea mays*.

In addition, the compounds I and I', their N-oxides and/or salts can be employed in crops which have been made substantially resistant, by breeding and/or genetic engineering methods, to the effect of I.

Furthermore, the substituted 2-phenylpyridines I and I' are also suitable for the desiccation and/or defoliation of plants. As desiccants they are particularly suitable for drying out the above-ground parts of crop plants such as potato, rape, sunflower and soybean. This allows completely mechanized harvesting of these important crop plants.

Also of economic interest is the facilitation of harvesting made possible by the concentration in time of the abscission or reduction in the strength of attachment to the tree in the case of citrus fruits, olives or other species and varieties of pomes, drupes and shell fruit. The same mechanism, i.e. promotion of the formation of separation tissue between fruit or leaf and stem part of the plant, is also essential for easily controlled defoliation of crop plants, especially cotton.

In addition, the shortening of the time interval in which the individual cotton plants become mature results in an improved quality of the fibers after harvest.

The active substances can be applied as such or in the form of their formulations or the use forms prepared therefrom, eg. in the form of directly sprayable solutions, powders, suspensions or dispersions, emulsions, oily dispersions, pastes, dusting agents, broadcasting agents, or granules, by spraying, atomizing, dusting, scattering or watering. The application forms depend entirely on the purposes for which they are used; they should ensure in every case that distribution of the active substances according to the invention is as fine as possible.

The formulations are produced in a conventional manner, eg. by extending the active substance with solvents and/or carriers, if desired using emulsifiers and dispersants, it also being possible in the case of water as diluent to use other organic solvents as auxiliary solvents.

Inert auxiliaries essentially suitable for this purpose are: mineral oil fractions of moderate to high boiling points such as kerosene and diesel oil, also coal tar oils and minerals of vegetable or animal origin, solvents such as aromatic compounds (eg. toluene, xylene), chlorinated aromatic compounds (eg. chlorobenzenes), paraffins (eg. petroleum fractions), alcohols (eg. methanol, ethanol, butanol, cyclohexanol), ketones (eg. cyclohexanone, isophorone), amines (eg. ethanolamine), N,N-dimethylformamide, N-methylpyrrolidone and water; carriers such as natural rock powders (eg. kaolins, aluminas, talc, chalk) and synthetic rock powders (eg. highly disperse silica, silicates); emulsifiers such as nonionic and anionic emulsifiers (eg. polyoxyethylene fatty alcohol ethers, alkylsulfonates and arylsulfonates) and dispersants such as lignin sulfite waste liquors and methylcellulose.

Aqueous application forms can be prepared from emulsion concentrates, dispersions, pastes, wettable powders or water-dispersable granules by adding water. To prepare emulsions, pastes or oil dispersions, the substances can be homogenized, as such or dissolved in an oil or solvent, using wetting agents, adhesion promoters, dispersants or emulsifiers, in water. However, it is also possible to prepare concentrates which are composed of active substances, wetting agent, adhesion promoter, dispersant or emulsifier and, where appropriate, solvent or oil and which are suitable for dilution with water.

Suitable surfactants are the alkali metal, alkaline earth metal and ammonium salts of aromatic sulfonic acids, eg. lignin-, phenol- of naphthalene- and dibutylnaphthalene-sulfonic acid, and of fatty acids, alkyl- and alkylarylsulfonates, alkyl sulfates, lauryl ether sulfates and fatty alcohol sulfates, as well as salts of sulfated hexa-, hepta- and octadecanols, and of fatty alcohol glycol ether, products of the condensation of sulfonated naphthalene and naphthalene derivatives with formaldehyde, products of the condensation of the naphthalene or naphthalenesulfonic acids with phenol and formaldehyde, polyoxyethylene octylphenol ether, ethoxylated isooctyl-, octyl- or nonylphenol, alkylphenol and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders and dusting agents and broadcasting agents can be prepared by mixing or grinding the active substances together with a solid carrier. Granules, eg. coated, impregnated or homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium and magnesium sulfates, magnesium oxide, ground plastics, fertilizers such as ammonium sulfate, ammonium phosphate, ammonium nitrate, ureas and vegetable products such as cereals flour, bark meal, wood meal and nutshell meal, cellulose powders or other solid carriers.

The concentration of the active substances I and I' in the formulations ready for use can vary within wide limits, for example from 0.01 to 95% by weight. The active substances are normally employed in a purity of from 90% to 100%, preferably 95% to 100% (according to the NMR spectrum). Examples of such formulations are:

I. 20 parts by weight of compound No. I.068 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Fine dispersion of the solution in 100,000 parts by weight of water results in an aqueous dispersion which contains 0.02% by weight of the active ingredient.

II. 20 parts by weight of compound No. I.106 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Fine dispersion of the solution in 100,000 parts by weight of water results in an aqueous dispersion which contains 0.02% by weight of the active ingredient.

III. 20 parts by weight of active ingredient No. I.163 are disolved in a mixture composed of 25 parts by weight of cyclohexanone, 65 parts by weight of a mineral oil fraction of boiling point 210° to 280° C. and 10 parts by weight of the adduct of 40 mol of ethylene oxide and 1 mol of castor oil. Fine dispersion of the solution in 100,000 parts by weight of water results in an aqueous dispersion which contains 0.02% by weight of the active ingredient.

IV. 20 parts by weight of active ingredient No. I.188 are thoroughly mixed with 3 parts by weight of sodium diisobutylnaphthalene-α-sulfonate, 17 parts by weight of the sodium salt of a lignosulfonic acid from a sulfite waste liquor and 60 parts by weight of powdered silica gel and ground in a hammer mill. Fine dispersion of the mixture in 20,000 parts by weight of water results in a spray liquor which contains 0.1% by weight of the active ingredient.

V. 3 parts by weight of active ingredient No. I.512 are mixed with 97 parts by weight of finely divided kaolin to result in a dusting agent which contains 3% by weight of the active ingredient.

VI. 20 parts by weight of active ingredient No. I.901 are intimately mixed with 2 parts by weight of calcium dodecylbenzenesulfonate, 8 parts by weight of fatty alcohol polyglycol ether, 2 parts by weight of sodium salt of a phenol/urea/formaldehyde condensate and 68 parts by weight of a paraffinic mineral oil to result in a stable oily dispersion.

The active ingredients or the herbicidal and growth-regulating agents can be applied by a pre-emergence or post-emergence method. Normally, the plants are sprayed or dusted with the active ingredients, or the seeds of the test plants are treated with the active ingredients. If the active ingredients are less well tolerated by certain crops, the application techniques can be such that the herbicidal agents are sprayed with the aid of spraying equipment so as to avoid as far as possible the leaves of the sensitive crops, while the active ingredients reach the leaves of unwanted plants growing underneath them or the uncovered surface of the soil (post-directed, lay-by).

The application rates of the active ingredient may vary depending on the aim of the control, the season and the stage of growth. When used as herbicides or defoliants, the application rate is preferably from 0.001 to 3.0, in particular 0.01 to 1.0, kg/ha active substance.

To widen the spectrum of action and to achieve synergistic effects, the substituted 2-phenylpyridines I and I' can be mixed and applied together with numerous representatives of other groups of herbicidal or growth-regulating active ingredients. Examples of suitable components of the mixture are diazines, 4H-3,1-benzoxazine derivatives, benzothiadiazinones, 2,6-dinitroanilines, N-phenylcarbamates, thiolcarbamates, halo carboxylic acids, triazines, amides, ureas, diphenyl ethers, triazinones, uracils, benzofuran derivatives, 1,3-cyclohexanedione derivatives which have, for example, a carboxyl or carbimino group in position 2, quinolinecarboxylic acid derivatives, imidazolinones, sulfonamides, sulfonylureas, aryloxy- and heteroaryloxyphenoxypropionic acids and their salts, esters and amides, and others.

It may additionally be beneficial to apply the compounds I or I', alone or in combination with other herbicides, also mixed with other crop protection agents, together with, for example, agents for controlling pests or phytopathogenic fungi or bacteria. Also of interest is the miscibility with mineral salt solutions which are used to eliminate deficiencies of nutrients and trace elements. It is also possible to use non-phytotoxic oils and oil concentrates.

PREPARATION EXAMPLES

Example 1

3-Chloro-2-(4-chloro-3-methoxyphenyl)-5-trifluoromethylpyridine (Table 1, Example I.001)

The preparation took place as shown in the following scheme:

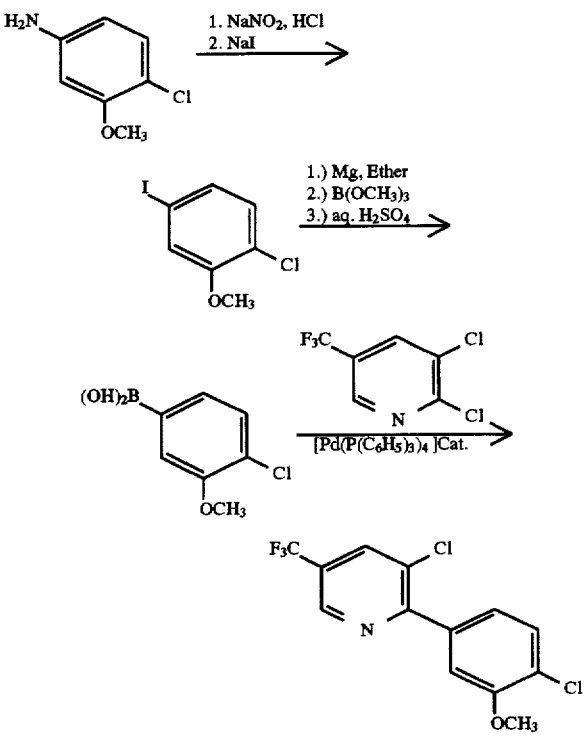

1st reaction step: 2-Chloro-5-iodoanisole 123.4 g (0.7835 mol) of 4-chloro-3-methoxyaniline were added to 190 ml concentrated hydrochloric acid in 760 ml of water. This suspension was vigorously stirred at 60° C. for one hour and then cooled to 0° C., and a solution of 59.5 g (0.862 mol) of sodium nitrite in 170 ml of water was added dropwise at below 5° C. The resulting mixture was then stirred at this temperature for 20 minutes and subsequently a solution of 129.2 g (0.862 mol) of sodium iodide in 220 ml of water was added dropwise. After the reaction mixture had warmed to about 20° C. it was stirred at 40°–50° C. for one hour and subsequently decolorized with a little dilute sodium bisulfite solution. The solution obtained after removal of the solids was extracted three times with 200 ml of ether each time. The combined ether phases were dried over sodium sulfate and concentrated. Yield: 190.6 g (96%) of a dark oily residue which, according to the $^1$H-NMR spectrum, had a purity of about 95%. The crude product can be purified by distillation at 100°–120° C. under 0.1 mbar to afford colorless crystals of melting point 38° C. However, this purification is unnecessary for further reactions.

$^1$H-NMR (270 MHz, in CDCl$_3$): δ [ppm]=3.87(s,3H), 7.06(d,1H), 7.20(d,1H), 7.22(dd,1H).

2nd reaction step: 4-Chloro-3-methoxybenzeneboronic acid

In a flame-dried flask, 1.93 g (79.2 mmol) of magnesium turnings were etched with a small crystal of iodine, and 50 ml of anhydrous ether were added. Then, under a nitrogen atmosphere, a solution of 20.0 g (79.2 mmol) 2-chloro-5-iodoanisole in 50 ml of anhydrous ether were added dropwise in such a way that the ether was kept boiling by the heat of reaction. After the addition was complete, the mixture was refluxed for 1½ hours and then filtered through glass wool, with exclusion of moisture, into a dropping funnel.

This Grignard solution and, synchronously but separately, 8.24 g (79.2 mmol) of trimethyl borate were added dropwise to 50 ml of anhydrous ether in a flame-dried flask under a nitrogen atmosphere at −60° to −70° C. The resulting suspension was then stirred at the stated temperature for one hour and, after it had warmed to about 20° C., acidified to pH 3 with 5% strength sulfuric acid. After separation of the phases, the aqueous phase was extracted three times with ether. The combined organic phases were dried over sodium sulfate and then concentrated. The residue was extracted by boiling three times with 100 ml of water each time. The aqueous phases were combined and cooled, when 4.6 g (32%) of colorless crystals separated out and were removed and dried under reduced pressure at 20°–25° C.

$^1$H-NMR (270 MHz, in $d^6$-DMSO): δ [ppm]=3.90(s,3H), 7.39(s,2H), 7.56(s,1H), 8.2(s,br.,2H).

3rd reaction step: 3-Chloro-2-(4-chloro-3-methoxyphenyl)-5-trifluoromethylpyridine 38.8 g (0.180 mol) of 2,3-dichloro-5-trifluoromethylpyridine, 33.5 g (0.180 mol) of 4-chloro-3-methoxybenzeneboronic acid, 0.7 g (0.61 mmol) of tetrakis(triphenylphosphine)palladium(O) and 45.3 g (0.539 mol) of sodium bicarbonate in a mixture of 550 ml of dimethoxyethane and 550 ml of water were refluxed for four hours. The mixture was then acidified to pH 4–5 with dilute hydrochloric acid, the dimethoxyethane was removed by distillation, and the remaining aqueous phase was extracted with methylene chloride. The combined methylene chloride phases were washed with water, dried over sodium sulfate and evaporated. The residue was stirred with a little cold n-hexane, filtered off with suction and dried. Yield: 44.2 g (76%) of colorless crystals of melting point 72° C.

$^1$H-NMR (270 MHz, in $CDCl_3$): δ [ppm]=3.96(s,3H), 7.30–7.38(m,2H), 7.48(d,1H), 8.05(s,1H), 8.84(s,1H).

Example 2

3-Chloro-2-(4-chloro-2-fluoro-5-methoxyphenyl)-5-trifluoromethylpyridine (Table 4, Example I.501)

In a preparation similar to that described above for 3-chloro-2-(4-chloro-3-methoxyphenyl)-5-trifluoromethylpyridine, reaction of 8.9 g (41 mmol) of 2,3-dichloro-5-trifluoromethylpyridine and 7.9 g (41 mmol) of 4-chloro-2-fluoro-5-methoxybenzeneboronic acid and subsequent purification of the crude product by chromatography on silica gel (methylene chloride as eluent) resulted in 2.6 g of colorless crystals.

Yield: 19%; melting point: 105°–106° C.

Example 3

3-Chloro-2-(4-chloro-3-hydroxyphenyl)-5-trifluoromethylpyridine (Table 1, Example I.021)

20.0 g (62.1 mmol) of 3-chloro-2-(4-chloro-3-methoxyphenyl)-5-trifluoromethylpyridine in 110 ml of 47% strength aqueous hydrobromic acid were refluxed for five hours. The reaction mixture was then diluted, while cooling in ice, with about 400 ml of water and extracted three times with 150 ml of methylene chloride each time. The combined organic phases were dried over sodium sulfate and evaporated to give a residue of 17.9 g (94%) of colorless crystals of melting point 105°–107° C.

$^1$H-NMR (270 MHz, in $CDCl_3$): δ [ppm]=6.0(s,br.,1H), 7.28(dd,1H), 7.40(d,1H), 7.43(d,1H), 8.05(s,1H), 8.83(s,1H).

Example 4

3-Chloro-2-(4-chloro-2-fluoro-5-hydroxyphenyl)-5-trifluoromethylpyridine (Table 4, Example I.521)

A preparation similar to that described above for 3-chloro-2-(4-chloro-3-hydroxyphenyl)-5-trifluoromethylpyridine resulted in 1.4 g of colorless crystals from 1.6 g (4.7 mmol) of 3-chloro-2-(4-chloro-2-fluoro-5-methoxyphenyl)-5-trifluoromethyl-pyridine.

Yield: 91%; melting point: 111°–112° C.

Example 5

3-Chloro-2-(4-chloro-3-propargyloxyphenyl)-5-trifluoromethylpyridine (Table 1, Example I.012)

1.73 g (14.6 mmol) of propargyl bromide were added dropwise to a mixture of 3.00 g (9.74 mmol) of 3-chloro-2-(4-chloro-3-hydroxyphenyl)-5-trifluoromethylpyridine, 4.0 g (29 mmol) of potassium carbonate and 100 ml of anhydrous dimethylformamide. The mixture was stirred at 20°–25° C. for about 15 hours and then poured into 400 ml of water. The solution was kept cold for a few hours, and the resulting crystals were then separated off, washed with water and dried under reduced pressure. Yield: 3.1 g (92%) of colorless crystals of melting point 102°–103° C.

$^1$H-NMR (250 MHz, in $CDCl_3$): δ [ppm]=2.57(t,1H), 4.86(d,2H), 7.38(dd,1H), 7.48–7.54(m,2H), 8.05(s,1H), 8.85(s,1H).

Example 6

3-Chloro-2-(4-chloro-2-fluoro-5-propargyloxyphenyl)-5-trifluoromethylpyridine (Table 4, Example 512)

In a preparation similar to that described above for 3-chloro-2-(4-chloro-3-propargyloxyphenyl)-5-trifluoromethylpyridine, reaction of 1.4 g (4.5 mmol) of 3-chloro-2-(4-chloro-2-fluoro-5-hydroxyphenyl)-5-trifluoromethylpyridine and 0.6 g (5 mmol) of propargyl bromide resulted in 1.1 g of colorless crystals. Yield: 67%; melting point: 97°–98° C.

Example 7

3-Chloro-2-(4-chloro-3-isopropoxyphenyl)-5-trifluoromethylpyridine (Table 1, Example I.004)

0.23 g (7.8 mmol) of an 80% suspension of sodium hydride in mineral oil was washed with anhydrous pentane to remove the mineral oil and then suspended in 50 ml of anhydrous dimethylformamide. A solution of 2.0 g (6.5 mmol) of 3-chloro-2-(4-chloro-3-hydroxyphenyl)5-trifluoromethylpyridine in 50 ml of anhydrous dimethylformamide was added dropwise to this suspension at 0° C. After the addition is complete, the mixture was stirred for 15 minutes and then 1.3 g (7.8 mmol) of isopropyl iodide were slowly added dropwise. The mixture was then stirred at 20°–25° C. for about 15 h and subsequently poured into 400 ml of water and extracted three times with methyl tert-butyl ether. The combined organic phases were washed with water, dried over sodium sulfate and evaporated under reduced pressure. Yield: 1.9 g (83%) of a colorless oil.

$^1$H-NMR (250 MHz, in $CDCl_3$): δ [ppm]=1.41(d,6H), 4.63(h,1H), 7.30(dd,1H), 7.35(d,1H), 7.49(d,1H), 8.08(s, 1H), 8.85(d,1H).

Example 8

3-Chloro-2-[4-chloro-3-(methoxycarbonylmethoxy)phenyl]-5-trifluoromethylpyridine (Table 1, Example I.014)

A preparation similar to that described above for 3-chloro-2-(4-chloro-3-propargyloxyphenyl)-5- trifluoromethylpyridine resulted in 2.2 g (89%) of colorless crystals of melting point 109°–110° C. from 2.0 g (6.5 mmol) of 3-chloro-2-(4-chloro-3-hydroxyphenyl)-5-trifluoromethylpyridine, 1.5 g (9.7 mmol) of methyl 2-bromoacetate, 1.8 g (13 mmol) of potassium carbonate and a total of 100 ml of dimethylformamide.

¹H-NMR (250 MHz, in CDCl₃): δ [ppm]=3.82(s,3H), 4.80(s,2H), 7.29(d,1H), 7.40(dd,1H), 7.52(d,1H), 8.05 (s,1H), 8.84(s,1H).

Example 9

3-Chloro-2-[4-chloro-3-(1-ethoxycarbonylethoxy) phenyl]-5-trifluoromethylpyridine (Table 1, Example I.017)

A preparation similar to that described above for 3-chloro-2-(4-chloro-3-propargyloxyphenyl)-5-trifluoromethylpyridine resulted in 2.4 g (90%) of a colorless oil from 2.0 g (6.5 mmol) of 3-chloro-2-(4-chloro-3-hydroxyphenyl)-5-trifluoromethylpyridine, 1.8 g (9.7 mmol) of ethyl 2-bromopropionate, 1.8 g (13 mmol) of potassium carbonate and a total of 100 ml of dimethylformamide.

¹H-NMR (270 MHz, in CDCl₃): δ [ppm]=1.28(t,3H), 1.73(d,3H), 4.21(q,2H), 4.80(q,1H), 7.31(d,1H), 7.39 (dd, 1H), 7.50(d,1H), 8.10(s,1H), 8.84(s,1H).

Example 10

3-Chloro-2-[4-chloro-3-(cyanomethoxy)phenyl]-5-trifluoromethylpyridine (Table 1, Example I.019)

A preparation similar to that described above for 3-chloro-2-(4-chloro-4-3-propargyloxyphenyl)-5-trifluoromethylpyridine resulted in 2.0 g (89%) of colorless crystals of melting point 85°–86° C. from 2.0 g (6.5 mmol) of 3-chloro-2-(4-chloro-3-hydroxyphenyl)-5-trifluoromethylpyridine, 1.2 g (9.7 mmol) of bromoacetonitrile, 1.8 g (13 mmol) of potassium carbonate and a total of 100 ml of dimethylformamide.

¹H-NMR (250 MHz, in CDCl₃): δ [ppm]=4.93(s,2H), 7.50–7.55(m,3H), 8.08(s,1H), 8.87(s,1H).

Example 11

3-Chloro-2-[4-chloro-3-(1-cyanoethoxy)phenyl]-5-trifluoromethylpyridine (Table 1, Example I.020)

A preparation similar to that described above for 3-chloro-2-(4-chloro-3-propargyloxyphenyl)-5-trifluoromethylpyridine resulted in 2.1 g (90%) of colorless crystals of melting point 75°–76° C. from 2.0 g (6.5 mmol) of 3-chloro-2-(4-chloro-3-hydroxyphenyl)-5-trifluoromethylpyridine, 1.3 g (9.7 mmol) of (+)-2-bromopropionitrile, 1.8 g (13 mmol) of potassium carbonate and a total of 100 ml of dimethylformamide.

1H-NMR (270 MHz, in CDCl₃): δ [ppm]=1.88(d,3H), 4.98(q,1H), 7.55(s,2H), 7.61(s,1H), 8.07(s,1H), 8.85(s,1H).

Example 12

3-Chloro-2-(4-chloro-3-nitrophenyl)-5-trifluoromethylpyridine (Table 1, Example I.064)

The preparation took place as shown in the following scheme:

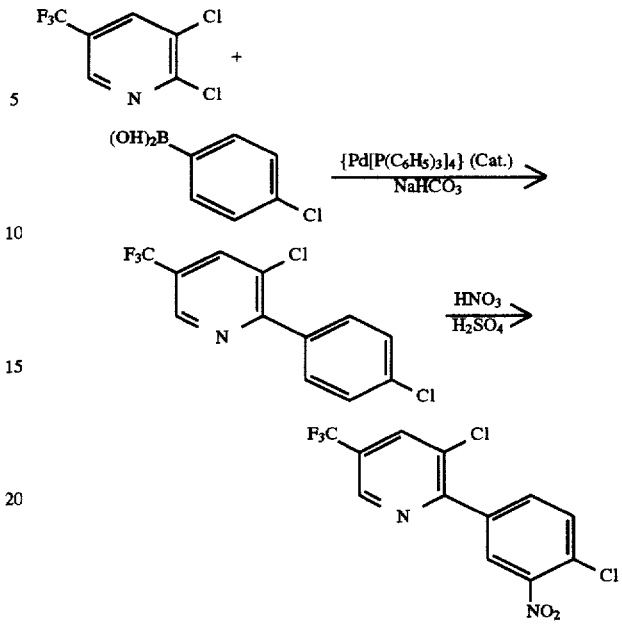

1st reaction step: 3-Chloro-2-(4-chlorophenyl)-5-trifluoromethylpyridine

A preparation similar to that described above for 3-chloro-2-(4-chloro-3-methoxyphenyl)-5-trifluoromethylpyridine resulted in 11.1 g (72%) of colorless crystals of melting point 78°–79° C. from 11.5 g (53.1 mmol) of 2,3-dichloro-5-trifluoromethylpyridine, 8.3 g (53.1 mmol) of 2,3-dichloro-5-trifluoromethylpyridine, 8.3 g (53.1 mmol) of 4-chlorobenzeneboronic acid, 120 mg (0.10 mmol) of tetrakis(triphenylphosphine)palladium(0) and 13.4 g (159 mmol) of sodium bicarbonate.

¹H-NMR (250 MHz, in CDCl₃): δ [ppm]=7.49(d,2H), 7.75(d,2H), 8.05(s,1H), 8.84(s,1H).

2nd reaction step: 3-Chloro-2-(4-chloro-3-nitrophenyl)-5-trifluoromethylpyridine 3.6 g (57 mmol) of concentrated nitric acid were added dropwise to a mixture of 11.1 g (38.0 mmol) of 3-chloro-2-(4-chloro-phenyl)-5-trifluoromethylpyridine in 50 ml of concentrated sulfuric acid while stirring and cooling in ice at 0°–5° C. The mixture was stirred at this temperature for two hours and then poured into 500 ml of ice-water. The product was extracted three times with 150 ml of ethyl acetate each time. The combined organic phases were washed twice with a little water, dried over sodium sulfate and finally concentrated under reduced pressure. The residue was purified by chromatography on silica gel (mobile phase: cyclohexane/ ethyl acetate 95:5). Yield: 11.8 g (90%) of colorless crystals of melting point 68°–69° C.

¹H-NMR (250 MHz, in CDCl₃): δ [ppm]=7.70(d,1H), 8.02(dd,1H), 8.12(d,1H), 8.40(s,1H), 8.88(s,1H).

Example 13

2-(3-Amino-4-chlorophenyl)-3-chloro-5-trifluoromethylpyridine (Table 1, Example I.065)

A preparation similar to that described above for 3-chloro-2-(3-amino-4-hydroxyphenyl)-5-trifluoromethylpyridine resulted in 12.8 g (91%) of colorless crystals of melting point 88°–90° C. from 15.4 g (45.7 mmol) of 3-chloro-2-(4-chloro-3-nitrophenyl)-5-trifluoromethylpyridine (prepared as in Example 12), 7.7 g (137 mmol) of iron powder, 80 ml of methanol and 40 ml of glacial acetic acid.

¹H-NMR (250 MHz, in CDCl₃): δ [ppm]=4.18(s,br.,2H), 7.00–7.13(m,2H), 7.35(d,1H), 8.03(s,1H), 8.80(s,1H).

Example 14

3-Chloro-2-[4-chloro-3-bis(methylsulfonyl) aminophenyl]-5-trifluoromethylpyridine (Table 1, Example I.067)

2.4 g (21.0 mmol) of methanesulfonyl chloride were slowly added dropwise to a mixture of 3.0 g (9.77 mmol) of 2-(3-amino-4-chlorophenyl)-3-chloro-5-trifluoromethylpyridine, 2.2 g (22.4 mmol) of triethylamine and 50 ml of anhydrous methylene chloride at 0°–5° C. The mixture was stirred at 20°–25° C. for about 15 hours and then washed twice with water, dried over sodium sulfate and finally concentrated. The residue was stirred with ether, filtered off with suction and dried under reduced pressure. Yield: 3.6 g (87%) of colorless crystals of melting point 230°–231° C.

¹H-NMR (270 MHz, in d⁶-DMSO): δ [ppm]=3.62(s,6H), 7.84(d,1H), 7.92(dd,1H), 8.09(d,1H), 8.68(s,1H), 9.12(s, 1H).

Example 15

3-Chloro-2-(4-chloro-3-methylsulfonylaminophenyl) -5-trifluoromethylpyridine (Table 1, Example I.066)

A solution of 3.6 g (7.78 mmol) of 3-chloro-2-[4-chloro-3-bis-(methylsulfonyl)aminophenyl]-5-trifluoromethylpyridine (prepared as in Example 13) and 100 mg of sodium methoxide in 100 ml of methanol were stirred at 20°–25° C. for three hours. Then most of the methanol was distilled off under reduced pressure. The residue was taken up in dilute hydrochloric acid, after which the product was extracted three times with ethyl acetate. The combined organic phases were dried over sodium sulfate and concentrated. The oily residue was treated with ether/ petroleum ether to afford 1.6 g (53%) of colorless crystals of melting point 133°–134° C.

1H-NMR (250 MHz, in d⁶-DMSO): δ [ppm]=3.06(s,3H), 7.55(dd,1H), 7.68(d,1H), 7.84(d,1H), 8.62(s,1H), 9.08(s, 1H), 9.7(s,br.,1H).

Example 16

3-Chloro-2-[4-chloro-3-(2-chloro-2-methoxycarbonylethyl)phenyl]-5-trifluoromethylpyridine (Table 1, Example I.163)

11.2 g (130 mmol) of methyl acrylate and 2.2 g (16.3 mmol) of copper(II) chloride were added to a solution of 2.0 g (19.5 mmol) of tert-butyl nitrite in 100 ml of anhydrous acetonitrile at 0° C. Subsequently, while stirring at 0° C., a solution of 4.0 g (13.0 mmol) of 2-(3-amino-4-chlorophenyl)-3-chloro-5-trifluoromethylpyridine in 100 ml of anhydrous acetonitrile was slowly added dropwise. After the addition was complete, the mixture was stirred at 20°–25° C. for 5 h, then filtered, concentrated and chromatographed on silica gel with cyclohexane/ethyl acetate (98:2) as mobile phase. Yield: 3.2 g (59%) of a colorless oil.

¹H-NMR (270 MHz, in CDCl₃): δ [ppm]=3.35(dd,1H), 3.58(dd,1H), 3.78(s,3H), 4.66(t,1H), 7.50(d,1H), 7.65(dd, 1H), 7.72(d,1H), 8.05(s,1H), 8.84(s,1H).

Example 17

3-Chloro-2-(4-chloro-3-methylphenyl)-5-trifluoromethylpyridine (Table 1, Example I.76)

The preparation took place as shown in the following scheme:

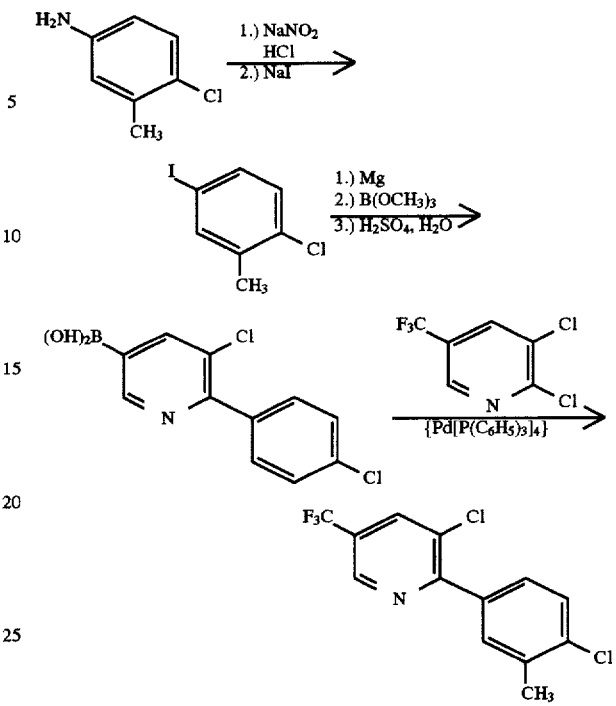

1st reaction step: 4-Chloro-3-methyliodobenzene

A preparation similar to that described above for 2-chloro-5-iodoanisole resulted in 206.0 g (93%) of a colorless liquid of boiling point 57°–58° C. mbar from 125.0 g (0.883 mol) of 4-chloro-3-methylaniline, 62.0 g (0.899 mol) of NaNO₂ and 135.0 g (0.900 mol) of NaI.

¹H-NMR (200 MHz, in CDCl₃): δ [ppm]=2.32(s,3H), 7.15(d,1H), 7.44(dd,1H), 7.59(d,1H).

2nd reaction step: 4-Chloro-3-methylbenzeneboronic acid

A preparation similar to that described above for 4-chloro-3-methoxybenzeneboronic acid resulted in 35.2 g (58%) of colorless crystals of melting point 255°–258 C., which can be reacted without further purification, from 90.0 g (0.356 mol) of 4-chloro-3-methyliodobenzene, 8.7 g (0.358 mol) of magnesium turnings and 37.0 g (0.356 mol) of trimethyl borate.

¹H-NMR (400 MHz, in d⁶-DMSO): δ [ppm]=2.38(s,3H), 7.37(d,1H), 7.70(dd,1H), 7.82(d,1H).

3rd reaction step: 3-Chloro-2-(4-chloro-3-methylphenyl)-5trifluoromethylpyridine.

A preparation similar to that described above for 3-chloro2-(4-chloro-3-methoxyphenyl)-5-trifluoromethylpyridine resulted in 120.0 g (99%) of colorless crystals of melting point 40°–42° C. from 93.4 g (0.432 mol) of 2,3-dichloro-5-trifluoromethylpyridine, 67.0 g (0.393 mol) of 4-chloro-3-methylbenzeneboronic acid and 0.4 g (0.35 mmol) of tetrakis(triphenylphosphine)palladium (0).

¹H-NMR (200 MHz, in CDCl₃): δ [ppm]=2.45(s,3H), 7.45(d,1H), 7.55(dd,1H), 7.64(d,1H), 8.04(d,1H), 8.84(d, 1H).

Example 18

2-(3-Bromomethyl-4-chlorophenyl)-3-chloro-5-trifluoromethylpyridine (Table 1, Example I.080)

A solution of 9.6 g (31.4 mmol) of 3-chloro-2-(4-chloro-3-methylphenyl)5-trifluoromethylpyridine (prepared as in Example 16) and 5.6 g (31.5 mmol) of N-bromosuccinimide in 150 ml of tetrachloromethane was irradiated with a 150 W high-pressure Hg lamp for one hour. For the workup, the precipitated succinimide was removed, and the filtrate was concentrated under reduced pressure. The residue was taken up in cyclohexane. The solids were removed and discarded, and the cyclohexane solution was concentrated again. The crude product was purified by chromatography on silica gel (mobile phase: n-pentane/methyl tert-butyl ether 20:1). Yield: 6.2 g (51%) of colorless crystals of melting point 71°–72° C.

$^1$H-NMR (250 MHz, in CDCl$_3$): δ [ppm]=4.66(s,2H), 7.50(d,1H), 7.71(dd,1H), 7.91(d,1H), 8.08(s,1H), 8.85(s, 1H).

Example 19

3-Chloro-2-(4-chloro-3-methoxymethylphenyl)-5-trifluoromethylpyridine (Table 1, Example I.081)

A solution of 1.05 g (19.4 mmol) of sodium methoxide in 5 ml of methanol was added to a solution of 5.0 g (12.9 mmol) of 2-(3-bromomethyl-4-chlorophenyl)-3-chloro-5-trifluoromethylpyridine prepared as in Example 17) in 100 ml of methanol. After stirring at room temperature for 96 hours, most of the methanol was removed by distillation under reduced pressure. The residue was taken up in water. Esterification with dilute hydrochloric acid was followed by extraction three times with 50 ml of n-hexane each time. The combined hexane phases were dried over sodium sulfate and then concentrated. The oily residue was induced to crystallize by trituration with cyclohexane. Yield: 3.5 g (81%) of colorless crystals of melting point 52°–54 ° C.

Example 20

3-Chloro-2-(4-chloro-3-chlorosulfonylphenyl)-5-trifluoromethylpyridine (Table 1, Example I.050)

40.0 g (0.137 mol) of 3-chloro-2-(4-chlorophenyl)-5-trifluoromethylpyridine (see above for preparation) were added in portions to 75 ml of chlorosulfonic acid while stirring and cooling in ice. After the addition was complete, the mixture was stirred at 130° C. for four hours. The cooled mixture was cautiously poured into ice-water which was then extracted three times with methylene chloride. The combined organic phases were dried over sodium sulfate and concentrated. Yield: 45.0 g (84%) of a dark oil.

Example 21

2-(3-Aminosulfonyl-4-chlorophenyl)-3-chloro-5-trifluoromethylpyridine (Table 1, Example I.051)

4 ml of concentrated aqueous ammonia solution were added all at once to a solution of 4.0 g (10.2 mmol) of 3-chloro-2-(4-chloro-3-chlorosulfonylphenyl)-5-trifluoromethylpyrine (prepared as in Example 19) in 50 ml of tetrahydrofuran. After stirring at 20°–25° C. for one hour, most of the tetrahydrofuran was removed by distillation under reduced pressure. The residue was kept in the cold for a few hours, after which the crystals which had separated out were removed and stirred in diisopropyl ether. Yield:

3.2 g (84%) of colorless crystals of melting point 176° C.

Example 22

3-Chloro-2-(4-chloro-3-methylaminosulfonylphenyl)-5-trifluoromethylpyridine (Table 1, Example I.052)

A preparation similar to that described above for 2-(3-aminosulfonyl-4-chlorophenyl)-3-chloro-5-trifluoromethylpyridine resulted in 3.6 g (91%) of a colorless oil from 4.0 g (10.2 mmol) of 3-chloro-2-(4-chloro-3-chlorosulfonylphenyl)-5-trifluoromethylpyridine and 4 ml of 40% strength aqueous methylamine solution.

Example 23

3-Chloro-2-(4-chloro-3-dimethylaminosulfonylphenyl)-5-trifluoromethylpyridine (Table 1, Example I.053)

A preparation similar to that described above for 2-(3-aminosulfonyl-4-chlorophenyl)-3-chloro-5-trifluoromethylpyridine resulted in 3.6 g (88%) of a colorless oil from 4.0 g (10.2 mmol) of 3-chloro-2-(4-chloro-3-chlorosulfonylphenyl)-5-trifluoromethylpyridine and 4 ml of 40% strength aqueous dimethylamine solution.

Example 24

2-(4-Chloro-3-methoxyphenyl)-5-trifluoromethylpyridine (Table 6, Example I.902)

A preparation similar to that described above for 3-chloro-2-(4-chloro-3-methoxyphenyl)-5-trifluoromethylpyridine resulted in 3.5 g (76%) of colorless crystals of melting point 74° C. from 2.7 g (16.1 mmol) of 2-chloro-5-trifluoromethylpyridine and 3.0 g (16.1 mmol) of 4-chloro-3-methoxybenzeneboronic acid.

Example 25

3-Chloro-2-(4-chloro-3-methoxyphenyl)pyridine 35 (Table 6, Example I.903)

A preparation similar to that described above for 3-chloro-2-(4-chloro-3-methoxyphenyl)-5-trifluoromethylpyridine resulted in 2.6 g (63%) of colorless crystals of melting point 116° C. from 2.4 g (16.2 mmol) of 2,3-dichloropyridine and 3.0 g (16.1 mmol) of 4-chloro-3-methoxybenzeneboronic acid.

Example 26

2-(4-Chloro-3-methoxyphenyl)-3,6-dichloro-5-trifluoromethylpyridine (Table 6, Example I.905)

A preparation similar to that described above for 3-chloro-2-(4-chloro-3-methoxyphenyl)-5-trifluoromethylpyridine resulted in 2.24 g (39%) of colorless crystals of melting point 88°–90° C. from 4.03 g (16.1 mmol) of 2,3,6-trichloro-5-trifluoromethylpyridine and 3.0 g (16.1 mmol) of 4-chloro-3-methoxybenzeneboronic acid.

$^1$H-NMR (250 MHz, in CDCl$_3$: δ [ppm]=3.97(s, 3H), 7.35–7.40(m,2H), 7.48(d, 1H), 8.10(s,1H)

Example 27

3-Chloro-2-(4-chloro-3-dibromomethylphenyl)-5-trifluoromethylpyridine (Table 1, Example I.079)

A solution of 75.0 g (0.245 mol) of 3-chloro-2-(4-chloro-3-methylphenyl)5-trifluoromethylpyridine (prepared as in Example 16) and 109.0 g (0.613 mol) of N-bromosuccinimide in 2 l of tetrachloromethane was irradiated under reflux with a 150 watt Hg immersion lamp for three hours. The mixture was cooled and then the succinimide which was formed and unreacted N-bromosuccinimide were removed. The solvent was removed by distillation under reduced pressure, after which

Example 28

3-Chloro-2-(4-chloro-3-formylphenyl)-5-trifluoromethylpyridine (Table 1, Example I.113)

6.99 g (15.1 mmol) of 3-chloro-2-(4-chloro-3-dibromomethylphenyl)-5-trifluoromethylpyridine in 100 ml of 96% strength sulfuric acid were stirred at 100° C. for one hour during which a vigorous stream of nitrogen was passed through the reaction mixture. The mixture was cooled and then poured into ice-water. The solid product was separated off, washed with water and dried under reduced pressure. Yield: 4.2 g (87%) of colorless crystals of melting point 94° C.

Example 29

2-(4-Chloro-3-methoxyphenyl)-5-trifluoromethyl-3-methylthiopyridine (Table 6, Example I.901)

3.0 g (9.3 mmol) of 3-chloro-2-(4-chloro-3-methoxyphenyl)-5-trifluoromethylpyridine and 0.7 g (10 mmol) of sodium thiomethoxide in a mixture of 50 ml of methanol and 20 ml of dimethylformamide were stirred at 80° C. for 7 h and then at 23° C. for 72 h. The mixture was then poured into 500 ml of ice-water, which was then extracted three times with 150 ml of tert-butyl methyl ether each time. The combined organic phases were washed twice with 100 ml of water each time, dried over sodium sulfate and concentrated.

Yield: 2.9 g (94%) of colorless crystals; melting point: 100°–103° C.

Example 30

2-(4-Chloro-3-methoxyphenyl)-5-trifluoromethyl-3-methoxypyridine (Table 6, Example I.904)

33.5 g of a 30% strength methanolic solution of sodium methoxide were added to a solution of 3.0 g (9.3 mmol) of 3-chloro-2-(4-chloro-3-methoxyphenyl)-5-trifluoromethylpyridine in 100 ml of methanol. The mixture was refluxed for 20 h and then poured into about 500 ml of ice-water. The product was extracted from the aqueous phase with 3×100 ml of methylene chloride. The combined organic phases were dried over sodium sulfate and concentrated. The oily residue was induced to crystallize by trituration with n-hexane. Yield: 1.3 g of colorless crystals; melting point: 62°–63° C. (purity about 85%).

Example 31

3-Chloro-2-(4-chloro-3-methoxyphenyl)-6-ethoxy-5-trifluoromethylpyridine (Table 6, Example I.925)

6.5 g (18 mmol) of 3,6-dichloro-2-(4-chloro-3-methoxyphenyl)-5-trifluoromethylpyridine and 6.1 g (109 mmol) of potassium hydroxide in 100 ml of ethanol were stirred at 23° C. for 41 h. The solvent was then removed by distillation and the residue was taken up in 100 ml of dilute hydrochloric acid. Extraction was carried out three times with 100 ml of methylene chloride each time. The combined extracts were dried over sodium sulfate and then concentrated. Yield: 6.3 g (85%) of a colorless oil (purity about 90%).

$^1$H-NMR (270 MHz, in $CDCl_3$): δ [ppm]=1.44 (t, 3H), 3.97 (s,3H), 4.52 (q,2H), 7.38 (dd,1H), 7.40 (d, 1H), 7.47 (d, 1H), 7.94 (s, 1H).

Example 32

3-Chloro-2-(4-chloro-3-methoxyphenyl)-5-trifluoromethylpyridine N-oxide (Table 5, Example I.802)

A solution of 4.5 g (14 mmol) of 3-chloro-2-(4-chloro-3-methoxyphenyl)-5-trifluoromethylpyridine and 9.7 g (31 mmol) of 3-chloroperbenzoic acid in 80 ml of methylene chloride was stirred at 23° C. for 4 days and then at 40° C. for 16 h. The mixture was then extracted with 100 ml of 10% strength aqueous sodium bisulfate solution, with 100 ml of a 10% strength aqueous sodium bicarbonate solution and three times with 80 ml of water each time. The organic phase was concentrated, and the residue was chromatographed on silica gel with cyclohexane/ethyl acetate (5:1). Yield: 3.6 g (76%) of colorless crystals; melting point: 156°–157° C.

Example 33

3-Chloro-2-(4-chloro-3-mercaptophenyl)-5-trifluoromethylpyridine

The preparation took place as shown in the following scheme:

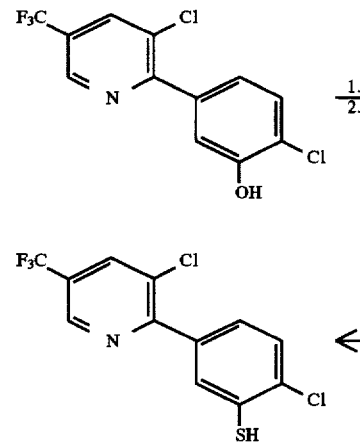
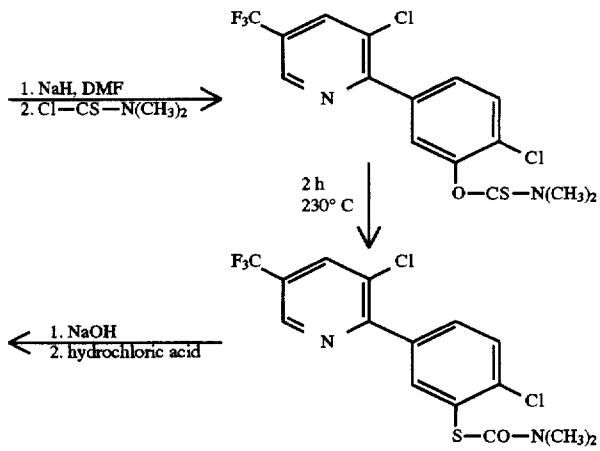

1st reaction step:

3-Chloro-2-(4-chloro-3-dimethylaminothiocarbonyloxyphenyl)-5-trifluoromethylpyridine A solution of 65.0 g of 3-chloro-2-(4-chloro-3-hydroxyphenyl)-5-trifluoromethylpyridine in 200 ml of dimethylformamide, and then 31.3 g of dimethylthiocarbamoyl chloride, were added dropwise to a suspension of 6.7 g of 80% sodium hydride in 300 ml of anhydrous dimethylformamide. The solution was stirred at 80° C. for one hour and then poured into 2.5 l of 1% by weight sodium hydroxide solution. After extraction three times with 250 ml of tert-butyl methyl ether each time the combined organic phases were washed twice with 150 ml of water each time and then dried over sodium sulfate and concentrated until crystallization started. After removal of the crystals, the mother liquor was concentrated further until more of the product started to crystallized out.

Total yield: 61.3 g (74%) of colorless crystals; melting point: 101°–103° C.

2nd reaction step:

3-Chloro-2-(4-chloro-3-dimethylaminocarbonylthiophenyl)-5-trifluoromethylpyridine 61.3 g of 3-chloro-2-(4-chloro-3-dimethylaminothiocarbonyloxyphenyl)5-trifluoromethylpyridine in 100 ml of sulfolane were heated at 230° C. for 2 h. The mixture was cooled and then poured into 400 ml of water, which was then extracted three times with 100 ml of ethyl acetate each time. The combined organic phases were washed twice with 100 ml of water each time and then dried over sodium sulfate and concentrated. The residue was purified by chromatography on silica gel (mobile phase: cyclohexane/ethyl acetate=6:1). Yield: 41.2 g (67%) of colorless crystals; melting point: 85°–86° C.

3rd reaction step:

3-Chloro-2-(4-chloro-3-mercaptophenyl)-5-trifluoromethylpyridine

A solution of 41.2 g of 3-chloro-2-(4-chloro-3-dimethylaminocarbonylphenyl)-5-trifluoromethylpyridine and 20.9 g of sodium hydroxide in 300 ml of methanol was stirred at 23° C. for 16 h. The methanol was removed by distillation and then the residue was taken up in 400 ml of water. The solution was extracted with ether and, after solidification with dilute hydrochloric acid, three times more with 100 ml of ether each time. The three last ether phases were combined, dried over sodium sulfate and concentrated. Chromatography on silica gel with cyclohexane/ethyl acetate as mobile phase afforded 28.7 g (85%) of a colorless oil.

$^1$H-NMR (270 MHz, in $CDCl_3$): δ [ppm]=4.00 (s,1H), 7.43–7.54 (m, 2H), 7.77 (s,1H), 8.04 (s,1H), 8.83 (s,1H).

Example 34

3-Chloro-2-[4-chloro-3-(2-propynylthio)phenyl]-5-trifluoromethylpyridine (Table 1, Example I.036)

2.0 g of 3-chloro-2-(4-chloro-3-mercaptophenyl)-5-trifluoromethylpyridine (prepared as in Example 33) and 2.1 g of potassium carbonate were introduced into 50 ml of anhydrous dimethylformamide amide at 23° C. After a dropwise addition of 0.73 g of propargyl bromide, the mixture was stirred for 16 h and then poured into 300 ml of water. After 30 minutes, the crystals which had formed were removed, washed with water and dried.

Yield: 1.8 g (81%) of colorless crystals; melting point: 91°–92° C.

Example 35

3-Chloro-2-(4-chloro-3-methylthiophenyl)-5-trifluoromethylpyridine (Table 1, Example I.025)

A preparation similar to that described above for 3-chloro-2-[4-chloro-3-(2-propynylthio)phenyl]-5-trifluoromethylpyridine resulted in 1.2 g (50%) of colorless crystals of melting point 96°–97° C. from 2.0 g of 3-chloro-2-(4-chloro-3-mercaptophenyl)-5-trifluoromethylpyridine and 0.9 g of methyl iodide.

Example 36

3-Chloro-2-[4-chloro-3-(1-ethoxycarbonylethylthio)phenyl]-5-trifluoromethylpyridine (Table 1, Example I.042)

In a preparation similar to that described above for 3-chloro-2-[4-chloro-3-(2-propynylthio)phenyl]-5-trifluoromethylpyridine, reaction of 2.0 g of 3-chloro-2-(4-chloro-3-mercaptophenyl)-5-trifluoromethylpyridine with 1.11 g of ethyl 2-bromopropionate and extraction of the product with tert-butyl methyl ether afforded 2.4 g (92%) of a colorless oil.

$^1$H-NMR (270 MHz, in $CDCl_3$) δ [ppm]=1.14 (t,3H), 1.58 (d,3H), 4.00 (q,1H), 4.12 (q,2H), 7.54 (d,1H), 7.66 (dd,1H), 7.97 (d,1H), 8.07 (s,1H), 8.85 (s,1H).

Example 37

4-[2-Chloro-5-(3-chloro-5-trifluoromethyl-2-pyridinyl)phenylaminosulfonyl]-3,5-dimethylisoxazole (Table 1, Example I.176)

A solution of 2.5 g of 2-(3-amino-4-chlorophenyl)-3-chloro-5-trifluoromethylpyridine and 2.3 g of 3,5-dimethylisoxazole-4-sulfonyl chloride in a mixture of 100 ml of toluene and 100 ml of pyridine was refluxed for 16 hours. The mixture was concentrated and the residue was taken up in 50 ml of ethyl acetate. The solution was washed with 50 ml each of 10% strength hydrochloric acid and 10% strength aqueous sodium bicarbonate solution and was dried over sodium sulfate and concentrated. Chromatography on silica gel with cyclohexane/ethyl acetate (6:1) resulted in 1.9 g of colorless crystals; melting point: 161°–162° C.

Example 38

3-Chloro-2-[4-chloro-3-(4-chlorophenylsulfonylamino)phenyl]-5-trifluoromethylpyridine (Table 1, Example I.167)

In a similar way to Example 37, reaction of 2.5 g of 2-(3-amino-4-chlorophenyl)-3-chloro-5-trifluoromethylpyridine and 1.9 g of 4-chlorobenzenesulfonyl chloride, and purification of the crude product by recrystallization from ether, resulted in 1.2 g of colorless crystals. Yield: 31%; melting point: 156°–157° C.

Example 39

Ethyl (±)-2-[2-Chloro-5-(3-chloro-5-trifluoromethyl-2-pyridinyl)phenylsulfonylamino]propionate (Table 1, Example I.179)

4.0 g of 3-chloro-2-(4-chloro-3-chlorosulfonylphenyl)-5-trifluoromethylpyridine, 2.4 g of D,L-alanine ethyl ester hydrochloride and 5.2 g of triethylamine in 50 ml of anhydrous tetrahydrofuran were stirred at 23° C. for 18 hours, after which the mixture was concentrated. The residue was taken up in 100 ml of methylene chloride. The solution was extracted twice with 30 ml of water each time, dried over sodium sulfate and concentrated. Chromatography of the residue on silica gel with cyclohexane/ethyl acetate (4:1) resulted in 2.8 g of a colorless oil. Yield: 58%;

$^1$H-NMR (270 MHz, in CDCl$_3$): δ [ppm]=1.15 (t,3H), 1.45 (d,3H), 3.98–4.14 (m,3H), 5.84 (d,1H), 7.68 (d,1H), 7.95 (dd,1H), 8.10 (s,1H), 8.53 (d,1H), 8.88 (s,1H).

Example 40

(S)-3-Chloro-2-[4-chloro-3-(2-methoxycarbonyl-1-pyrrolidinyl)phenyl]-5-trifluoromethylpyridine
(Table 1, Example I.181) 3.0 g of 3-chloro-2-(4-chloro-3-chlorosulfonylphenyl)-5-trifluoromethylpyridine, 1.9 g of L-proline methyl ester hydrochloride and 3.9 g of triethylamine in 100 ml of anhydrous tetrahydrofuran were stirred at 23° C. for 18 hours, after which the mixture was concentrated. The residue was taken up in 100 ml of methylene chloride. The solution was extracted twice with 30 ml of water each time, dried over sodium sulfate and concentrated. Chromatography of the residue on silica gel with cyclohexane/ethyl acetate (4:1) resulted in 2.9 g of a colorless oil. Yield: 78%;

$^1$H-NMR (270 MHz, in CDCl$_3$): δ [ppm]=1.86–2.37 (m,4H), 3.48–3.79 (m,2H), 3.63 (s,3H), 4.65 (dd,1H), 7.66 (d,1H), 7.93 (dd,1H), 8.10 (s,1H), 8.57 (d,1H), 8.87 (s,1H).

Example 41

3-Chloro-2-[4-chloro-3-(2,5-dichloro-3-thienylaminosulfonyl)phenyl]-5-trifluoromethylpyridine (Table 1, Example I.182)

3.0 g of 3-chloro-2-(4-chloro-3-chlorosulfonylphenyl)-5-trifluoromethylpyridine and 1.7 g of 3-amino-2,5-dichlorothiophene hydrochloride in a mixture of 100 ml of toluene and 100 ml of pyridine were refluxed for 6 hours. The residue after concentration was dissolved in 100 ml of ethyl acetate. The solution was extracted with 50 ml of dilute hydrochloric acid and 50 ml of water, dried over sodium sulfate and concentrated. Chromatography on silica gel with methylene chloride resulted in 0.6 g of colorless crystals. Yield: 15%, melting point: 106°–108° C.

Example 42

3-Chloro-2-(4-chloro-3-methoxymethylphenyl)-5-trifluoromethylpyridine (Table 1, Example I.081)

7.0 g of a 30% by weight solution of sodium methoxide in methanol were added to a solution of 5.0 g of 2-(3-bromomethyl-4-chlorophenyl)-3-chloro-5-trifluoromethylpyridine in 100 ml of anhydrous methanol. The mixture was refluxed for 8 hours and then concentrated. The residue was taken up in 100 ml of 10% strength hydrochloric acid, after which three extractions with 50 ml of ether each time were carried out. The ether phases were dried over sodium sulfate and concentrated. The oily residue was induced to crystallize with a little cold cyclohexane. Yield: 2.9 g (67%) of colorless crystals; melting point: 52°–54° C.

Example 43

3-Chloro-2-(4-chloro-3-ethylthiomethylphenyl)-5-trifluoromethylpyridine and 2-(4-chloro-3-ethylthiomethylphenyl)-3-ethylthio-5-trifluoromethylpyridine (Table 1, Example I.097 and Table 2, Example I.304)

A solution of 4.0 g of 2-(3-bromomethyl-4-chlorophenyl)-3-chloro-5-trifluoromethylpyridine and 1.3 g of sodium thioethoxide in 80 ml of anhydrous dimethylformamide was stirred at 23° C. for 18 hours and then refluxed for 4 hours. The cooled reaction mixture was then poured into 400 ml of ice-water, which was then extracted three times with 100 ml of tert-butyl methyl ether each time. The combined organic phases were extracted with 100 ml of water, dried over sodium sulfate and concentrated. The residue was chromatographed on silica gel with n-heptane/tert-butyl methyl ether (20:1).

Yield fraction 1: 1.0 g (26%) of a colorless oil (first compound mentioned);

$^1$H-NMR (200 MHz, in CDCl$_3$): δ [ppm]=1.28 (t,3H), 2.55 (q,2H), 3.92 (s,2H), 7.50 (d,1H), 7.64 (dd,1H), 7.83 (d,1H), 8.06 (s,1H), 8.85 (s,1H).

Fraction 2: 1.5 g (37%) of colorless crystals; melting point: 62°–63° C. (second compound mentioned).

Example 44

3-Chloro-2-(4-chloro-3-hydroximinomethylphenyl)-5-trifluoromethylpyridine (Table 1, Example I.129)

22.6 g of 3-chloro-2-(4-chloro-3-formylphenyl)-5-trifluoromethylpyridine, 6.5 g of sodium bicarbonate and 5.4 g of hydroxylamine hydrochloride in 100 ml of tetrahydrofuran were stirred at 23° C. for 24 hours. The tetrahydrofuran was then removed, after which the residue was taken up in 100 ml of methylene chloride. The solution was washed twice with 100 ml of water. The solid formed during this was removed, washed with water and dried. Concentration of the organic phase resulted in a residue which was purified by chromatography on silica gel with cyclohexane/ethyl acetate (7:3). Yield: 26.1 g (82%) of colorless crystals; melting point: 173°–174° C.

Example 45

3-Chloro-2-(4-chloro-3-ethoximinomethylphenyl)-5-trifluoromethylpyridine pyridine (Table 1, Example I.131)

4.0 g of 3-chloro-2-(4-chloro-3-formylphenyl)-5-trifluoromethylpyridine and 4.4 g of a 45% strength aqueous ethylhydroxylamine solution in 100 ml of tetrahydrofuran were refluxed for 3 hours and then stirred at 23° C. for 16 hours. The residue obtained after evaporation was purified by chromatography on silica gel (mobile phase: n-heptane/tert-butyl methyl ether=10:1). Yield: 4.1 g (91%) of an oil which slowly crystallized; melting point: 58°–59° C.

Example 46

3-Chloro-2-(4-chloro-3-methoxycarbonylmethoximinomethylphenyl)-5-trifluoromethylpyridine (Table 1, Example I.136)

4.0 g of 3-chloro-2-(4-chloro-3-hydroximinomethylphenyl)-5-trifluoromethylpyridine, 1.8 g of potassium carbonate and 2.0 g of methyl bromoacetate in 90 ml of dimethylformamide were stirred at 80° C. for 8 hours and then at 23° C. for 55 hours. The mixture was then poured into 800 ml of ice-water, followed by extraction four times with 150 ml of tert-butyl methyl ether each time. The combined organic phases were washed with 150 ml of water, dried over sodium sulfate and concentrated. The residue was purified by chromatography on silica gel with cyclohexane/ethyl acetate (10:1). Yield: 3.9 g (81%) of colorless crystals; melting point: 49° C.

Example 47

3-Chloro-2-[4-chloro-3-(1-ethoxycarbonylethoximinomethyl)phenyl]-5-trifluoromethylpyridine (Table 1, Example I.140)

4.0 g of 3-chloro-2-(4-chloro-3-hydroximinomethylphenyl)-5-trifluromethylpyridine, 5.1 g of potassium carbonate and 6.7 g of ethyl 2-bromopropionate in 80 ml of dimethylformamide were stirred at 100° C. for 12 hours. The mixture was cooled and then poured into 800 ml of water. The mixture was then extracted four times with 150 ml of tert-butyl methyl ether each time. The combined organic phases were washed with 150 ml of water, dried over sodium sulfate and concentrated. The residue was purified by chromatography on silica gel with cyclohexane/ethyl acetate (10:1). Yield: 4.0 g (77%) of a colorless oil.

$^1$H-NMR (270 MHz, in CDCl$_3$): δ [ppm]=1.29 (t,3H), 1.56 (d,3H), 4.23 (q,2H), 4.85 (q,1H), 7.50 (d,1H), 7.72 (dd,1H), 8.05 (s,1H), 8.27 (d,1H), 8.65 (s,1H), 8.84 (s,1H).

Example 48

3-Chloro-2-(4-chloro-3-dimethoxymethylphenyl)-5-trifluoromethylpyridine (Table 1, Example I.114)

50 ml of trimethyl orthoformate were added to 40.0 g of montmorillonite K-10 in 250 ml of anhydrous dichloromethane, after which a solution of 20.0 g of 3-chloro-2-(4-chloro-3-formylphenyl)-5-trifluoromethylpyridine in 50 ml of dichloromethane was added dropwise while stirring and cooling in ice. After stirring at 23° C. for 20 hours, the clay was removed and thoroughly washed with dichloromethane. The dichloromethane phase was concentrated. The residue was purified by chromatography on silica gel with cyclohexane/ethyl acetate (10:1). Yield: 22.1 g (96%) of a colorless oil.

$^1$H-NMR (270 MHz, in CDCl$_3$): δ [ppm]=3.42 (s,3H), 5.70 (s,1H), 7.52 (d,1H), 7.72 (dd,1H), 8.06 (s,1H), 8.10 (d,1H), 8.87 (s,1H).

Example 49

3-Chloro-2-[4-chloro-3-(4-methyl-1,3-dioxolan-2-yl)phenyl]-5-trifluoromethylpyridine (Table 1, Example I.118)

2.0 g of 1,2-propanediol and 100 mg of p-toluenesulfonic acid were added to 3.2 g of 3-chloro-2-(4-chloro-3-dimethoxymethylphenyl)-5-trifluoromethylpyridine in 100 ml of anhydrous toluene. The mixture was then refluxed for two hours and stirred at 23° C. for 16 hours. Extraction was carried out first with 50 ml of a 10% by weight sodium bicarbonate solution and then three times with 80 ml of water each time, after which the organic solution was dried over sodium sulfate and concentrated. The residue was purified by chromatography on silica gel with cyclohexane/ethyl acetate (10:1). Yield: 3.1 g (94%) of a colorless oil (1:1 mixture of diastereomers);

$^1$H-NMR (270 MHz, in CDCl$_3$): δ [ppm]=1.39(d,3H), 1.41(d,3H), 3.58–3.68(m,2H), 4.12–4.49(m,4H), 6.23(s, 1H), 6.37(s,1H), 7.50(d,2H), 7.74(dd,2H), 8.06(s,2H), 8.14 (d,2H), 8.86(s,2H).

Example 50

3-Chloro-2-[4-chloro-3-(4-vinyl-1,3-dioxolan-2-yl)phenyl]-5-trifluoromethylpyridine (Table 1, Example I.119)

3.2 g of 3-chloro-2-(4-chloro-3-dimethoxymethylphenyl)-5-trifluoromethylpyridine, 2.3 g of 1-butene-3,4-diol and 100 mg of p-toluenesulfonic acid in 100 ml of anhydrous toluene were refluxed for 12 hours. The solution was cooled and then washed with 50 ml of 10% by weight aqueous sodium bicarbonate solution and three times with 50 ml of water each time, dried over sodium sulfate and concentrated. The crude product was purified by chromatography on silica gel (mobile phase: cyclohexane/ethyl acetate=10:1). Yield: 3.2 g (95%) of a colorless oil (1:1 mixture of diastereomers);

IR (KBr): ν [cm$^{-1}$]=1602, 1324, 1217, 1194, 1162, 1137, 1100, 1083, 1047, 988.

Example 51

3-Chloro-2-[4-chloro-3-(4,5-bis(methoxycarbonyl)-1,3-dioxolan-2-yl)phenyl]-5-trifluoromethylpyridine (Table 1, Example I.123)

3.0 g of 3-chloro-2-(4-chloro-3-dimethoxymethylphenyl)-5-trifluoromethyl-pyridine, 5.4 g of dimethyl L(+)-tartrate and 100 mg of p-toluenesulfonic acid in 180 ml of anhydrous toluene were refluxed for 10 hours. The solution was cooled and then washed with 50 ml of 10% by weight sodium bicarbonate solution and three times with 50 ml of water each time, dried over sodium sulfate and concentrated. Chromatography on silica gel resulted in 3.0 g (77%) of colorless crystals; melting point: 48°–53° C.

Example 52

3-Chloro-2-[4-chloro-3-(2-chloro-2-methoxycarbonylvinyl)phenyl]-5-trifuloromethylpyridine (Table 1, Example I.142)

13.7 g of methyl propiolate and 2.7 g of copper(II) chloride were added to a solution of 2.5 g of tert-butyl nitrite in 100 ml of anhydrous acetonitrile at 0° C. Subsequently, while stirring at 0° C., a solution of 5.0 g of 2-(3-amino-4-chlorophenyl)-3-chloro-5-trifluoromethylpyridine in 100 ml of anhydrous acetonitrile was added dropwise. After the addition was complete, the mixture was stirred at 20°–25° C. for 5 hours and then filtered. The crude product obtained after concentration of the filtrate was chromatographed on silica gel with cyclohexane/ethyl acetate (100:1). Yield: 1.3 g (19%) of colorless crystals (1:1 mixture of E and Z isomers); melting point: 71°–73° C.

Example 53

(E)-3-Chloro-2-[4-chloro-3-(2-ethoxycarbonylvinyl)phenyl]-5-trifluoromethylpyridine (Table 1, Example I.146)

A solution of 1.35 g of sodium ethoxide in 20 ml of anhydrous ethanol was added dropwise to 4.0 g of 3-chloro-2-(4-chloro-3-formylphenyl)-5-trifluoromethylpyridine and 2.9 g of triethyl phosphonatoacetate in 70 ml of anhydrous toluene. After stirring at about 20° C. for 44 hours, the solvent was removed. The residue was taken up in 100 ml of 10% strength hydrochloric acid and extracted three times with 100 ml of ethyl acetate each time. The combined organic phases were washed with 100 concentrated. Chromatography on silica gel with cyclohexane/ethyl acetate (10:1) resulted in 3.4 g (71%) of colorless crystals; melting point: 118°–120° C.

Example 54

3-Chloro-2-[4-chloro-3-(2-ethoxycarbonyl-2-methylvinyl)phenyl]-5-trifluoromethylpyridine (Table 1, Example I.149)

A solution of 1.75 g of sodium ethoxide in 30 ml of anhydrous ethanol was added dropwise to 8.0 g of 3-chloro-2-(4-chloro-3-formylphenyl)-5-trifluoromethylpyridine and 6.0 g of triethyl 2-phosphonatopropionate in 80 ml of anhydrous toluene. The mixture was stirred at about 20° C. for 2 hours and then concentrated. The residue was taken up in 150 ml of ethyl acetate. The solution was washed with 100 ml of 5% strength hydrochloric acid and then three times with 100 ml of water each time, dried over sodium sulfate and concentrated. The crude product was chromatographed with cyclohexane/ethyl acetate (10:1) on silica gel to afford 9.2 g (91%) of colorless crystals (85:15 mixture of E and Z isomers); melting point: 88°–91° C.

Example 55

3-Chloro-2-(4-chloro-3-hydroxycarbonylphenyl)-5-trifluoromethylpyridine (Table 1, Example I.102)

38.5 g of sodium perborate tetrahydrate were added in portions over the course of 30 minutes to a solution of 16.0 g of 3-chloro-2-(4-chloro-3-formylphenyl)-5-trifluoromethylpyridine in 100 ml of glacial acetic acid at 100° C., followed by stirring at 100° C. for 1.5 hours. The mixture was cooled and then poured into 400 ml of water. The product was extracted from the aqueous phase with 3×100 ml of tert-butyl methyl ether. The combined organic phases were dried over sodium sulfate and then concentrated. The residue was triturated with n-hexane. The material insoluble in hexane was removed and extracted by boiling twice with ether, the pyridine N-oxide byproduct remaining undissolved. The combined ether phases were dried over sodium sulfate and concentrated to result in 13.7 g (81%) of colorless crystals; melting point: 149°–151° C.

Example 56

3-Chloro-2-(4-chloro-3-methoxycarbonylphenyl)-5-trifluoromethylpyridine (Table 1, Example I.103)

4.8 g of 3-chloro-2-(4-chloro-3-formylphenyl)-5-trifluoromethylpyridine, 8.4 g of N-iodosuccinimide, 5.2 g of potassium carbonate and 120 ml of methanol were stirred at 23° C. for 20 hours. Most of the methanol was removed by distillation and then a solution of 7 g of $Na_2S_2O_3$ pentahydrate in 200 ml of water was added, after which the mixture was extracted three times with 100 ml of tert-butyl methyl ether each time. The combined organic phases were washed with 50 ml of water, dried over sodium sulfate and concentrated. Yield: 4.9 g (93%) of a colorless oil;

$^1$H-NMR (270 MHz, in $CDCl_3$): δ [ppm]=3.95(s,3H), 7.59(d,1H), 7.88(dd,1H), 8.08(s,1H), 8.32(d,1H), 8.87(s,1H).

Example 57

3-Chloro-2-(4-chloro-3-isopropoxycarbonylphenyl)-5-trifluoromethylpyridine (Table 1, Example I.106)

A small piece of sodium was added to a solution of 4.0 g of 3-chloro-2-(4-chloro-3-methoxycarbonylphenyl)-5-trifluoromethylpyridine in 20 ml of anhydrous isopropanol, followed by stirring at 0° C. for 20 hours. The solvent was then removed. The residue was taken up in 50 ml of water. The aqueous phase was extracted three times with 50 ml of tert-butyl methyl ether each time. The combined organic phases were dried over sodium sulfate and concentrated. Yield: 2.5 g (58%) of a colorless oil;

$^1$H-NMR (270 MHz, in $CDCl_3$): δ [ppm]: 1.41(d,6H), 5.32(h,1H), 7.58(d,1H), 7.86(dd,1H), 8.09(s,1H), 8.24(d,1H), 8.87(d,1H).

Example 58

3-Chloro-2-(4-chloro-3-chloroformylphenyl)-5-trifluoromethylpyridine 23 g of 3-chloro-2-(4-chloro-3-hydroxycarbonylphenyl)-5-trifluoromethylpyridine in 23 ml of thionyl chloride were refluxed for 5 hours. The excess thionyl chloride was then removed by distillation. The remaining dark brown oil was used without further purification for the subsequent reaction.

Example 59

2-(3-Carbamoyl-4-chlorophenyl)-3-chloro-5-trifluoromethylpyridine (Table 1, Example I.185)

A solution of 4.0 g of 3-chloro-2-(4-chloro-3-chloroformylphenyl)-5-trifluoromethylpyridine in 10 ml of methylene chloride was added dropwise to 100 ml of a 25% by weight aqueous ammonia solution cooled to 0° C. After 3 hours, the crystals which had formed were separated off, stirred with n-hexane, again separated off, washed with n-hexane and finally dried. Yield: 2.8 g (75%) of colorless crystals; melting point: 167°–168° C.

Example 60

3-Chloro-2-(4-chloro-3-dimethylaminocarbonylphenyl)-5-trifluoromethylpyridine

A solution of 3.5 g of 3-chloro-2-(4-chloro-3-chloroformylphenyl)-5-trifluoromethylpyridine in 10 ml of methylene chloride was added dropwise to 75 ml of a 40% by weight aqueous dimethylamine solution cooled to 0° C. The mixture was stirred at 0 to 5° C. for 4 hours and then diluted with 225 ml of water, after which it was extracted three times with 100 ml of tert-butyl methyl ether each time. The combined organic phases were washed twice with 100 ml of water each time, dried over sodium sulfate and concentrated. The residue was chromatographed on silica gel with cyclohexane/ethyl acetate (7:3). Yield: 2.2 g (61%) of colorless crystals; melting point: 90°–91° C.

Example 61

3-Chloro-2-(4-chloro-3-ethoxyaminocarbonylphenyl)-5-trifluoromethylpridine (Table 1, Example I.187)

A solution of 4.0 g of 3-chloro-2-(4-chloro-3-chloroformylphenyl)-5-trifluoromethylpyridine in 10 ml of methylene chloride was added dropwise to 80 ml of a 45% by weight aqueous ethylhydroxylamine solution at 0° to 5° C. The mixture was stirred for 2 hours and diluted to 300 ml with water, after which it was extracted three times with 100 ml of tert-butyl methyl ether each time. The combined organic phases were washed twice with 100 ml of water each time, dried over sodium sulfate and concentrated. The residue was chromatographed on silica gel with cyclohexane/ethyl acetate (7:3). Yield: 3.2 g (76%) of colorless crystals; melting point: 162°–163° C.

Example 62

Ethyl (2S)-2-[2-chloro-5-(3-chloro-5-trifluoromethyl-2-pyridinyl)-benzoylamino]-3-methylbutanoate (Table 1, Example I.188)

A solution of 3.55 g of 2-chloro-2-(4-chloro-3-chloroformylphenyl)-5-trifluoromethylpyridine in 10 ml of methylene chloride was added dropwise to a mixture of 3.63 g of L-valine ethyl ester hydrochloride, 7.9 g of pyridine and 30 ml of methylene chloride at 23° C. After stirring for 60 hours, 160 ml of methylene chloride were added. The mixture was washed three times with 150 ml of water each time, dried over sodium sulfate and then concentrated. The crude product was purified by chromatography on silica gel with cyclohexane/ethyl acetate (10:1). Yield: 2.2 g (48%) of colorless crystals; melting point: 90°-92° C.

Example 63

The preparation took place as shown in the following scheme:

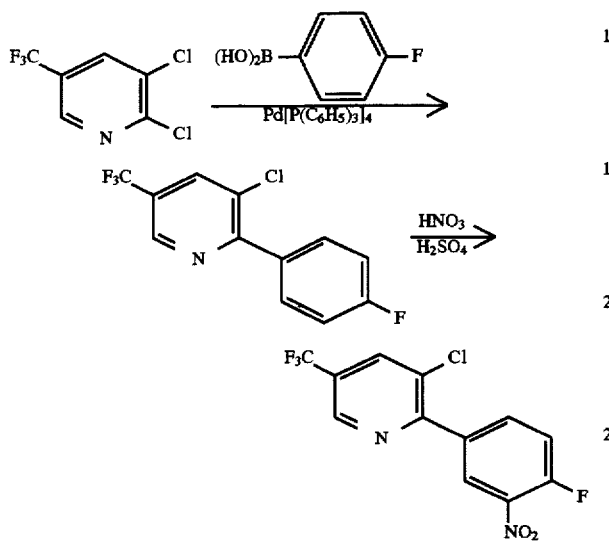

3-Chloro-2-(4-fluoro-3-nitrophenyl)-5-trifluoromethylpyridine (Table 3, Example L409)

In a preparation similar to that described above for 3-chloro-2-(4-chloro-3-nitrophenyl)-5-trifluoromethylpyridine, nitration of 66.6 g of 3-chloro-2-(4-fluorophenyl)-5-trifluoromethylpyridine with 22.8 g of 100% strength nitric acid resulted in 62.6 g (81%) of a colorless oil which slowly crystallized.

$^1$H-NMR (250 MHz, in CDCl$_3$): δ [ppm]=7.47(t,1H), 8.09–8.19(m,2H), 8.60(dd,1H), 8.89(s,1H)

Precursor: 3-chloro-3-(4-fluorophenyl)-5-trifluoromethylpyridine

In a preparation similar to that described above for 3-chloro-2-(4-chlorophenyl)-5-trifluoromethylpyridine, use of 55.0 g of 2,3-dichloro-5-trifluoromethylpyridine, 35.6 g of 4-fluorobenzeneboronic acid, 1.0 g of tetrakis(triphenylphosphine)palladium, 64.2 g of sodium bicarbonate, 300 ml of dimethoxyethane and 500 ml of water resulted in 65.0 g (93%) of colorless crystals; melting point: 41°-42° C.

Example 64

3-Chloro-2-(4-cyano-3-ethylsulfonylaminophenyl)-5-trifluoromethylpyridine (Table 3, Example L404)

The preparation took place as shown in the following scheme:

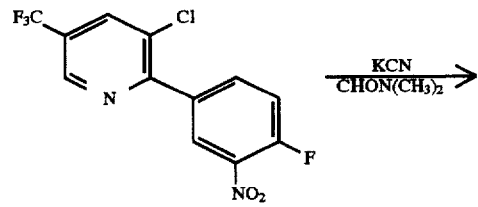

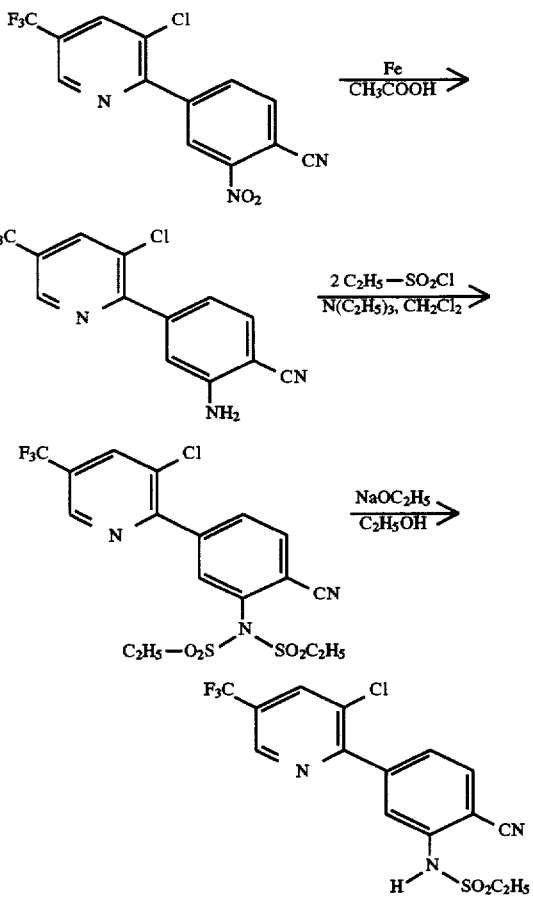

1st reaction step

3-Chloro-2-(4-cyano-3-nitrophenyl)-5-trifluoromethylpyridine (Table 3, Example L401)

5.0 g of 3-chloro-2-(4-fluoro-3-nitrophenyl)-5-trifluoromethylpyridine and 1.5 g of potassium cyanide in 50 ml of dimethylformamide were heated at 50° C. for 4 hours and then stirred at 23° C. for 20 hours. The mixture was then poured into 200 ml of water. The aqueous phase was extracted three times with 100 ml of tertbutyl methyl ether each time. The combined organic phases were washed twice with 50 ml of water each time, dried over sodium sulfate and concentrated. The residue was purified by chromatography on silica gel (mobile phase: cyclohexane/ethyl acetate=9:1). Yield: 2.7 g (53%) of a yellow oil which slowly crystallized.

$^1$H-NMR (400 MHz, in CDCl$_3$): δ [ppm]=8.10(d,1H), (8.20 (s,1H), 8.36(dd,1H), 8.82(d,1H), 8.94(s,1H).

2nd reaction step 2-(3-Amino-4-cyanophenyl)-3-chloro-5-trifluoromethylpyridine (Table 3, Example L402)

In a preparation similar to that described above for 3-chloro-2-(3-amino-4-hydroxyphenyl)-5-trifluoromethylpyridine, use of 21.1 g of 3-chloro-2-(4-cyano-3-nitrophenyl)-5-trifluoromethylpyridine, 10.8 g of iron powder, 116 ml of methanol and 58 ml of glacial acetic acid resulted, after final trituration in a little ether, in 18.7 g (98%) of a dark oil.

$^1$H-NMR (270 MHz, in d$^6$-DMSO): δ [ppm]=6.30(s,br., 2H), 6.85(s,br.,1H), 7.15(s,br.,1H), 7.55(s,br.,1H), 8.60 s,br., 1H), 9.05(s,br.,1H).

3rd reaction step

3-Chloro-2-[4-cyano-3-bis(ethylsulfonyl)aminophenyl]-5-trifluoromethylpyridine, (Table 3, Example I.403)

In a preparation similar to that described above for 3-chloro-2-[4-chloro-3-bis(methylsulfonyl)aminophenyl]-5-trifluoromethylpyridine, use of 4.0 g of 2-(3-amino-4-cyanophenyl)-3-chloro-5-trifluoromethylpyridine, 1.7 g of ethanesulfonyl chloride, 1.5 g of triethylamine and 100 ml of dichloromethane resulted in 4.2 g (65%) of colorless crystals.

$^1$H-NMR (270 MHz, in CDCl$_3$): δ [ppm]=1.53(t,6H), 3.7–3.82(m,4H), 7.91(s,1H), 8.02(d,1H), 8.07(d,1H), 8.12(s,1H), 8.90(s,1H).

4th reaction step

3-Chloro-2-(4-cyano-3-ethylsulfonylaminophenyl)-5-trifluoromethylpyridine (Table 3, Example I.404)

In a preparation similar to that described above for 3-chloro-2-(4-chloro-3-methylsulfonylaminophenyl)-5-trifluoromethylpyridine, use of 4.2 g of 3-chloro-2-[4-cyano-3-bis(ethylsulfonyl)aminophenyl]-5-trifluoromethylpyridine, about 100 mg of sodium ethoxide and 100 ml of ethanol resulted in 2.0 g (59%) of colorless crystals;

$^1$H-NMR (270 MHz, in CDCl$_3$): δ [ppm]=1.44(t,3H), 3.24(9,2H), 7.45(s,1H), 7.63(d,1H), 7.72(d,1H), 8.10 (s,2H), 8.90(s,1H).

Tables 1 to 6 which follow list further compounds I which have been or can be prepared by one of the processes described.

TABLE 1

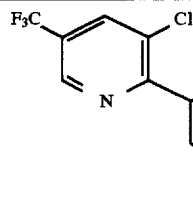

Ia (R$^1$ = R$^3$ = R$^5$ = H;
R$^2$ = CF$_3$; R$^4$, R$^6$ = Cl)

| No. | R$^7$ | M.p./IR [cm$^{-1}$]/$^1$H-NMR [ppm] |
|---|---|---|
| I.001 | —OCH$_3$ | 72° C. |
| I.002 | —O—CH$_2$—CH$_3$ | |
| I.003 | —O—CH$_2$CH$_2$CH$_3$ | |
| I.004 | —O—CH(CH$_3$)$_2$ | 1.41(d, 6H), 4.63(h, 1H), 7.30(dd, 1H), 7.35(d, 1H), 7.49(d, 1H), 8.08(s, 1H), 8.85(d, 1H) |
| I.005 | —O—CH$_2$—CH$_2$—C$_2$H$_5$ | |
| I.006 | —O—CH(CH$_3$)—C$_2$H$_5$ | |
| I.007 | —O—CH$_2$—CH(CH$_3$)$_2$ | |
| I.008 | —O—CH$_2$—CH$_2$—CH$_2$—C$_2$H$_5$ | |
| I.009 | —O—CH$_2$—CH=CH$_2$ | |
| I.010 | H, Cl / C= / —OCH$_2$, H | |
| I.011 | H, H / C= / —OCH$_2$, Cl | |
| I.012 | —O—CH$_2$—C≡C—H | 102–103° C. |
| I.013 | —O—CH(CH$_3$)C≡C—H | 96–98° C. |
| I.014 | —O—CH$_2$—CO—OCH$_3$ | 109–110° C. |
| I.015 | —O—CH$_2$—CO—OC$_2$H$_5$ | 62–63° C. |
| I.016 | —O—CH(CH$_3$)—CO—OCH$_3$ | 102–103° C. |
| I.017 | —O—CH(CH$_3$)—CO—OC$_2$H$_5$ | 1.28(t, 3H), 1.73(d, 3H), 4.21(q, 2H), 4.80(q, 1H), 7.31(d, 1H), 7.39(dd, 1H), 7.50(d, 1H), 8.10(s, 1H), 8.84(s, 1H). |
| I.018 | —O—cyclopentyl | |
| I.019 | —O—CH$_2$—C≡N | 85–86° C. |
| I.020 | —O—CH(CH$_3$)—C≡N | 75–76° C. |
| I.021 | —O—H | 105–107° C. |
| I.022 | —O—CH$_2$—CO—O—(CH$_2$)$_4$—CH$_3$ | |
| I.023 | —O—CH(CH$_3$)—CO—O—(CH$_2$)$_4$—CH$_3$ | |
| I.024 | —O—CH$_2$-phenyl | |
| I.025 | —S—CH$_3$ | 96–97° C. |
| I.026 | —S—C$_2$H$_5$ | |
| I.027 | —S—CH$_2$—C$_2$H$_5$ | |
| I.028 | —S—CH(CH$_3$)$_2$ | 1.39(d, 6H), 3.57(h, 1H), 7.45–7, 58 (m, 2H), 7.78(d, 1H), 8.05(s, 1H9, 8.86 (s, 1H) |
| I.029 | —S—CH$_2$—CH$_2$—C$_2$H$_5$ | |

TABLE 1-continued

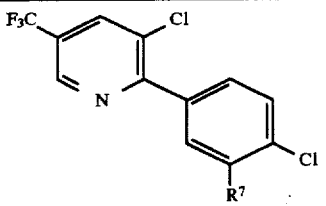

Ia (R$^1$ = R$^3$ = R$^5$ = H;
R$^2$ = CF$_3$; R$^4$, R$^6$ = Cl)

| No. | R$^7$ | M.p./IR [cm$^{-1}$]/$^1$H-NMR [ppm] |
|---|---|---|
| L030 | —S—CH(CH$_3$)—C$_2$H$_5$ | |
| L031 | —S—CH$_2$—CH(CH$_3$)$_2$ | |
| L032 | —S—CH$_2$—CH$_2$—CH$_2$—C$_2$H$_5$ | |
| L033 | —S—CH$_2$—CH=CH$_2$ | 3.65(d, 2H), 5.15(d, 1H), 5.26(d, 1H), 5.84–6.02(m, 1H), 7.44–7.59(m, 2H), 7.72 (s, 1H), 8.06(s, 1H), 8.86(s, 1H) |
| L034 | 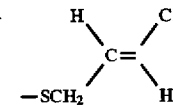 | |
| L035 | 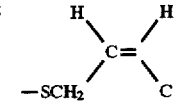 | |
| L036 | —S—CH$_2$—C≡C—H | 91–92° C. |
| L037 | —S—CH(CH$_3$)—C≡C—H | |
| L038 | —S—CH$_2$—CO—OH | 144–145° C. |
| L039 | —S—CH$_2$—CO—OCH$_3$ | 88–89° C. |
| L040 | —S—CH$_2$—CO—OC$_2$H$_5$ | 73° C. |
| L041 | —S—CH(CH$_3$)—CO—OCH$_3$ | 1.59(d, 3H), 3.68(s, 3H), 3.99(q, 1H), 7.55 (d, 1H), 7.67(dd, 1H), 7.97(d, 1H), 8.07 (s, 1H), 8.86(s, 1H) |
| L042 | —S—CH(CH$_3$)—CO—OC$_2$H$_5$ | 1.14(t, 3H), 1.58(d, 3H), 4.00(q, 1H), 4.12 (q, 2H), 7.54(d, 1H), 7.66(dd, 1H), 7.97 (d, 1H), 8.07(s, 1H), 8.85(s, 1H) |
| L043 | —S—cyclopentyl | |
| L044 | —S—CH$_2$—C≡N | 97–98° C. |
| L045 | —S—CH(CH$_3$)—C≡N | 1.72(d, 6H), 4.09(q, 1H), 7.62(d, 1H), 7.78 (dd, 1H), 8.07(d, 1H), 8.13(s, 1H), 8.85 (s, 1H) |
| L046 | —S—CH$_2$—CO—O—(CH$_2$)$_4$—CH$_3$ | 1.86(t, 3H), 1.18–1.42(m, 4H), 1.58 (p, 2H), 3.76(s, 2H), 4.11(t, 2H), 7.51 (d, 1H), 7.60(dd, 1H), 8.83(d, 1H), 8.06 (s,1H), 8.85 (s,1H) |
| L047 | —S—CH(CH$_3$)—CO—O—(CH$_2$)$_4$—CH$_3$ | |
| L048 | —S—CH$_2$-phenyl | |
| L049 | —S—CH$_2$—(4-Cl-phenyl) | |
| L050 | —SO$_2$—Cl | 7.79(d, 1H), 8.10(d, 1H), 8.13(dd, 1H), 8.65 (d, 1H), 8.88(d, 1H). |
| L051 | —SO$_2$—NH$_2$ | 176° C. |
| L052 | —SO$_2$—NH—CH$_3$ | 5.15(q, 1H), 7.68(d, 1H), 7.98(dd, 1H), 8.10(d, 1H), 8.57(s, 1H), 8.89(s, 1H). |
| L053 | —SO$_2$—N(CH$_3$)$_2$ | 2.95(s, 6H), 7.68(d, 1H), 7.94(dd, 1H), 8.10 (d, 1H), 8.53(d, 1H), 8.88(d, 1H). |
| L054 | —SO$_2$—NH—C$_2$H$_5$ | 1.14(t, 3H), 3.04(q, 2H), 0.92(t, 1H), 7.68(d, 1H), 7.95(d, 1H), 8.10(d, 1H), 8.59(d, 1H), 8.89(d, 1H). |
| L055 | —SO$_2$—NH—CH(CH$_3$)$_2$ | 104–108° C. |
| L056 | —SO$_2$—N(CH$_3$)—C$_2$H$_5$ | |
| L057 | —SO$_2$—N(C$_2$H$_5$)$_2$ | 77° C.; 1.18(t, 6H), 3.42(q, 4H), 7.65 (d, 1H), 7.90(dd, 1H), 8.10(d, 1H), 8.57 (d, 1H), 8.87(d, 1H) |
| L058 | —SO$_2$—(pyrrolidin-1-yl) | 104–105° C. |
| L059 | —SO$_2$—(piperidin-1-yl) | 87–88° C. |
| L060 | —SO$_2$—(morpholin-4-yl) | 114–115° C. |
| L061 | —SO$_2$—NH-phenyl | |
| L062 | —SO$_2$—N(CH$_3$)-phenyl | |
| L063 | —SO$_2$—NH—CH$_2$-phenyl | |
| L064 | —NO$_2$ | 68–69° C. |

TABLE 1-continued

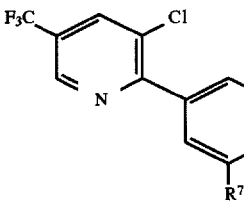

Ia (R¹ = R³ = R⁵ = H;
R² = CF₃; R⁴, R⁶ = Cl)

| No. | R⁷ | M.p./IR [cm⁻¹]/¹H-NMR [ppm] |
|---|---|---|
| I.065 | —NH₂ | 88–90° C. |
| I.066 | —NH—SO₂—CH₃ | 133–134° C. |
| I.067 | —N(SO₂—CH₃)₂ | 230–231° C. |
| I.068 | —NH—SO₂—C₂H₅ | 100–102° C. |
| I.069 | —N(SO₂—C₂H₅)₂ | 204–205° C. |
| I.070 | —NH—SO₂—CH₂—C₂H₅ | |
| I.071 | —NH—CHO | |
| I.072 | —NH—CO—CH₃ | |
| I.073 | —NH—CO—C₂H₅ | |
| I.074 | —N(CO—CH₃)—SO₂—CH₃ | |
| I.075 | —N(CO—CH₃)—SO₂—C₂H₅ | |
| I.076 | —CH₃ | 40–42° C. |
| I.077 | 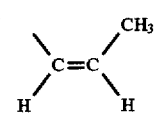 | |
| I.078 | 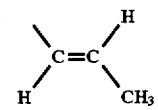 | |
| I.079 | —CHBr₂ | 75–77° C. |
| I.080 | —CH₂—Br | 71–72° C. |
| I.081 | —CH₂—O—CH₃ | 52–54° C. |
| I.082 | —CH₂—O—C₂H₅ | 44° C. |
| I.083 | —CH₂—O—(CH₂)₂—CH₃ | 0.97(t, 3H), 1.68(se, 2H), 3.56(t, 2H), 4.68(s, 2H), 7.46(d, 1H), 7.64(dd, 1H), 7.95(d, 1H), 8.05(d, 1H), 8.85(d, 1H) |
| I.084 | —CH₂—O—CH(CH₃)₂ | 89° C. |
| I.085 | —CH₂—O—(CH₂)₃—CH₃ | |
| I.086 | —CH₂—O—CH(CH₃)—C₂H₅ | |
| I.087 | —CH₂—O—CH₂—CH(CH₃)₂ | |
| I.088 | —CH₂—O—CH₂—CH=CH₂ | 4.15(d, 2H), 4.70(s, 2H), 5.19–5.44(m, 2H), 5.88–6.09(m1, H), 7.50(d, 1H), 7.68(dd, 1H), 7.98(d, 1H), 8.08(d, 1H), 8.86(d, 1H) |
| I.089 | —CH₂—O—CH₂—C≡C—H | 49° C. |
| I.090 | —CH₂—O—CH₂—CO—OCH₃ | |
| I.091 | —CH₂—O—CH₂—CO—OC₂H₅ | |
| I.092 | —CH₂—OCH(CH₃)—C≡C—H | 86–88° C. |
| I.093 | —CH₂—O—CH(CH₃)—CO—OCH₃ | |
| I.094 | —CH₂—O—CH(CH₃)—CO—OC₂H₅ | |
| I.095 | —CH₂—O—cyclopentyl | |
| I.096 | —CH₂—SCH₃ | 62–64° C. |
| I.097 | —CH₂—SC₂H₅ | 1.28(t, 3H), 2.55(q, 2H), 3.92(s, 2H), 7.50 (d, 1H), 7.64(dd, 1H), 7.83(d, 1H), 8.06 (s, 1H), 8.85(s, 1H) |
| I.098 | —CH₂—S—(CH₂)₂—CH₃ | 0.98(t, 3H), 1.62(se, 2H), 2.50(t, 2H), 3.88 (s, 2H), 7.44(d, 1H), 7.63(dd, 1H), 7.82 (d, 1H), 8.04(s, 1H), 8.84(s, 1H) |
| I.099 | —CH₂—S—CH₂—CO—OCH₃ | |
| I.100 | —CH₂—S—CH₂—CO—OC₂H₅ | |
| I.101 | —CH₂—N(CH₃)₂ | |
| I.102 | —CO—OH | 149–151° C. |
| I.103 | —CO—OCH₃ | 3.95(s, 3H), 7.59(d, 1H), 7.88(dd, 1H), 8.08(s, 1H), 8.32(d, 1H), 8.87(s, 1H) |
| I.104 | —CO—OC₂H₅ | 1.42(t, 3H), 4.44(q, 2H), 7.57(d, 1H), 7.88 (dd, 1H), 8.08(s, 1H); 8.30(d, 1H), 8.87 (s, 1H) |
| I.105 | —CO—O—(CH₂)₂—CH₃ | 1.07(t, 3H), 1.83(se, 2H), 4.34(t, 2H), 7.59 (d, 1H), 7.88(dd, 1H), 8.09(s, 1H), 8.32 |

TABLE 1-continued

Ia (R¹ = R³ = R⁵ = H; R² = CF₃; R⁴, R⁶ = Cl)

| No. | R⁷ | M.p./IR [cm⁻¹]/¹H-NMR [ppm] |
|---|---|---|
| I.106 | —CO—OCH(CH₃)₂ | (d, 1H), 8.88(s, 1H)<br>1.41(d, 6H), 5.32(h, 1H), 7.58(d, 1H), 7.86 (dd, 1H), 8.09(s, 1H), 8.24(d, 1H), 8.87 (d, 1H) |
| I.107 | —CO—O—(CH₂)₃—CH₃ | |
| I.108 | —CO—OCH(CH₃)—C₂H₅ | |
| I.109 | —CO—OCH₂—CH(CH₃)₂ | |
| I.110 | —CO—O—(CH₂)₄—CH₃ | |
| I.111 | —CO—OCH₂—CH₂—OCH₃ | |
| I.112 | —CO—OCH₂—CH₂—OC₂H₅ | |
| I.113 | —CHO | 94° C. |
| I.114 | —CH(OCH₃)₂ | 3.42(s, 3H), 5.70(s, 1H), 7.52(d, 1H), 7.72 (dd, 1H), 8.06(s, 1H), 8.10(d, 1H), 8.87 (s, 1H) |
| I.115 | —CH(OC₂H₅)₂ | 1.27(t, 6H), 3.53–3.80(m, 4H), 5.80(s, 1H), 7.49(d, 1H), 7.70(dd, 1H), 8.04(s, 1H), 8.13(d, 1H), 8.86(s, 1H) |
| I.116 | —CH(OCH₂—C₂H₅)₂ | |
| I.117 | 1,3-Dioxolan-2-yl | |
| I.118 | 4-Methyl-1,3-dioxolan-2-yl | 1.39(d, 3H), 1.41(d, 3H), 3.58–3.68 (m, 2H), 4.12–4.49(m, 4H), 6.23(s, 1H), 6.37(s, 1H), 7.50(d, 2H), 7.74(dd, 2H), 8.06(s, 2H), 8.14(d, 2H), 8.86(s, 2H) (ca. 1:1 mixture of diastereomers) |
| I.119 | 4-Vinyl-1,3-dioxolan-2-yl | 1602, 1324, 1217, 1194, 1162, 1137, 1100, 1083, 1047, 988<br>(ca. 1:1 mixture of diastereomers) |
| I.120 | 4,5-Dimethyl-1,3-dioxolan-2-yl | 1602, 1380, 1324, 1194, 1162, 1138, 1101, 1084, 1041, 909<br>(ca. 1.5:1.5:1 mixture of diastereomers). |
| I.121 | 4-Ethyl-1,3-dioxolan-2-yl | 1602, 1382, 1324, 1217, 1194, 1162, 1138, 1100, 1082, 1046<br>(ca. 1.5:1 mixture of diastereomers) |
| I.122 | —CH(O—)(S—) (dioxolane-like, O/S 5-ring) | |
| I.123 | 4,5-Bis(methoxy-carbonyl)-1,3-dioxolan-2-yl | 48–53° C. |
| I.124 | —CH(O—)(S—) (O/S 5-ring) | |
| I.125 | 1,3-Dithiolan-2-yl | 3.3–3.5(m, 4H), 6.12(s, 1H), 7.47(d, 1H), 7.62(dd, 1H), 8.04(s, 1H), 8.29(d, 1H), 8.85(s, 1H) |
| I.126 | 4-Methyl-1,3-dithiolan-2-yl | 1601, 1451, 1377, 1324, 1162, 1137, 1099, 1084, 1045, 766<br>(ca 60:40 mixture of diastereomers) |
| I.127 | —CH(O—)(O—) (1,3-dioxane) | |
| I.128 | —CH(S—)(S—) (1,3-dithiane) | 90–91° C. |

TABLE 1-continued

Ia ($R^1 = R^3 = R^5 = H$; $R^2 = CF_3$; $R^4$, $R^6 = Cl$)

| No. | $R^7$ | M.p./IR [cm$^{-1}$]/$^1$H-NMR [ppm] |
|---|---|---|
| I.129 | —CH=N—OH | 173–174° C. |
| I.130 | —CH=N—OCH$_3$ | 65–67° C. |
| I.131 | —CH=N—OC$_2$H$_5$ | 58–59° C. |
| I.132 | —CH=N—OCH$_2$—C$_2$H$_5$ | |
| I.133 | —CH=N—OCH(CH$_3$)$_2$ | |
| I.134 | —CH=N—OCH$_2$—CH$_2$—C$_2$H$_5$ | |
| I.135 | —CH=N—OCH$_2$—CO—OH | |
| I.136 | —CH=N—OCH$_2$—CO—OCH$_3$ | 49° C. |
| I.137 | —CH=N—OCH$_2$—CO—OC$_2$H$_5$ | 49° C. |
| I.138 | —CH=N—OCH(CH$_3$)—CO—OH | |
| I.139 | —CH=N—OCH(CH$_3$)—CO—OCH$_3$ | 1.56(d, 3H), 3.77(s, 3H), 4.88(q, 1H), 7.50 (d, 1H), 7.72(dd, 1H), 8.06(s, 1H), 8.27 (d, 1H), 8.66(s, 1H), 8.87(s, 1H) |
| I.140 | —CH=N—OCH(CH$_3$)—CO—OC$_2$H$_5$ | 1.29(t, 3H), 1.56(d, 3H), 4.23(q, 2H), 4.85 (q, 1H), 7.50(d, 1H), 7.72(dd, 1H), 8.05 (s, 1H), 8.27(d, 1H), 8.65(s, 1H), 8.84 (s, 1H) |
| I.141 | —CH=C(Cl)—COOH | |
| I.142 | —CH=C(Cl)—CO—OCH$_3$ | 71–73° C. (cis/trans ca. 1:1) |
| I.143 | \C=C/ with H, Cl, CO—OC$_2$H$_5$ | |
| I.144 | \C=C/ with H, H, COOH | |
| I.145 | \C=C/ with H, H, CO—OCH$_3$ | 97–98° C. |
| I.146 | \C=C/ with H, H, CO—OC$_2$H$_5$ | 118–120° C. |
| I.147 | \C=C/ with H, CH$_3$, COOH | |
| I.148 | —CH=C(CH$_3$)—CO—OCH$_3$ | 103° C. (cis/trans ca. 5:95) |
| I.149 | —CH=C(CH$_3$)—CO—OC$_2$H$_5$ | 88–91° C. (cis/trans ca 15:85) |
| I.150 | \C=C/ with H, Cl, CO—NH$_2$ | |
| I.151 | \C=C/ with H, Cl, CO—NHCH$_3$ | |

TABLE 1-continued
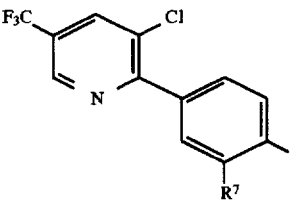
Ia (R$^1$ = R$^3$ = R$^5$ = H; R$^2$ = CF$_3$; R$^4$, R$^6$ = Cl)
| No. | R$^7$ | M.p./IR [cm$^{-1}$]/$^1$H-NMR [ppm] |
|---|---|---|
| I.152 | 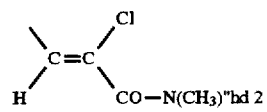 | |
| I.153 | 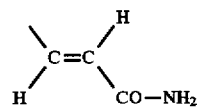 | |
| I.154 | 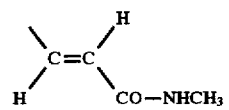 | |
| I.155 | 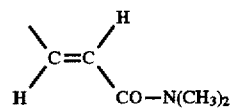 | |
| I.156 | 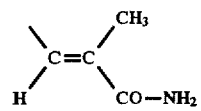 | |
| I.157 | 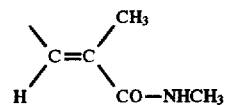 | |
| I.158 | 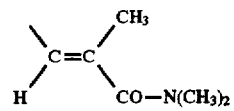 | |
| I.159 | 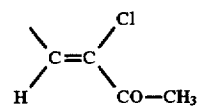 | |
| I.160 | 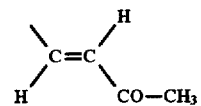 | |
| I.161 | 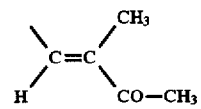 | |
| I.162 | —CH$_2$—CH(Cl)—CO—CH$_3$ | |
| I.163 | —CH$_2$—CH(Cl)—CO—OCH$_3$ | 1749, 1602, 1324, 1217, 1199, 1163, 1138, 1100, 1085, 1049 |
| I.164 | —CH$_2$—CH(Cl)—CO—OC$_2$H$_5$ | |

TABLE 1-continued
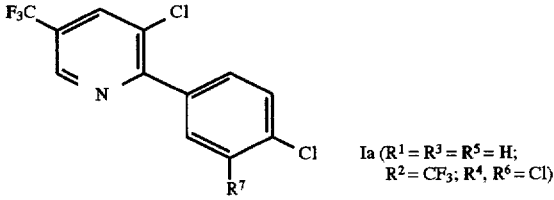
Ia (R¹ = R³ = R⁵ = H;
R² = CF₃; R⁴, R⁶ = Cl)
| No. | R⁷ | M.p./IR [cm⁻¹]/¹H-NMR [ppm] |
|---|---|---|
| I.165 | 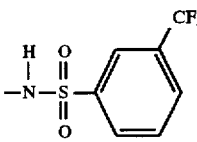 | 133–134° C. |
| I.166 | 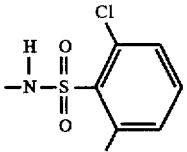 | 158–159° C. |
| I.167 | 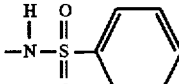 | 156–157° C. |
| I.168 | 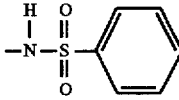 | 191–193° C. |
| I.169 | 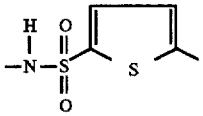 | 114–115° C. |
| I.170 | 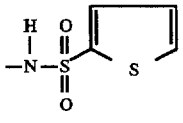 | |
| I.171 | 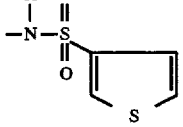 | |
| I.172 | —N[SO₂-(5-chlorthien-2-yl)]₂ | 167–168° C. |
| I.173 | —NH—SO₂-(2,5-dichlorthien-3-yl) | 132–133° C. |
| I.174 | —NH—SO₂-(4,5-dichlorthien-2-yl) | 154–155° C. |
| I.175 | —NH—SO₂-(4,5-dibromthien-2-yl) | 157–158° C. |
| I.176 | —NH—SO₂-(3,5-dimethylisoxazol-4-yl) | 161–162° C. |
| I.177 | —NH—SO₂-thien-2-yl | 144–145° C. |
| I.178 | —NH—SO₂-thien-3-yl | |
| I.179 | —SO₂—NH—CH(CH₃)—CO—OC₂H₅ (aus D,L-Alanin) | 1.15(t, 3H), 1.45(d, 3H), 3.98-4, 14 (m, 3H), 5.84(d, 1H), 7.68(d, 1H), 7.95 (dd, 1H), 8.10(s, 1H), 8.53(d, 1H), 8.88 (s, 1H) |
| I.180 | —SO₂—N(CH₂—C₂H₅)₂ | 0.85(t, 6H), 1.58(se, 4H), 3.32(t, 4H), 7.64 (d, 1H), 7.90(dd, 1H), 8.10(s, 1H), 8.57 (d, 1H), 8.87(s, 1H) |

TABLE 1-continued

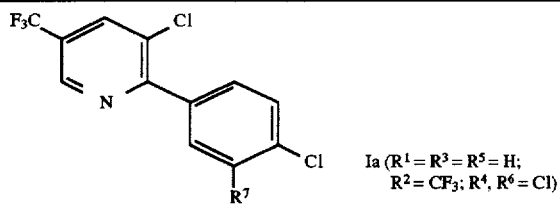

Ia ($R^1 = R^3 = R^5 = H$; $R^2 = CF_3$; $R^4, R^6 = Cl$)

| No. | $R^7$ | M.p./IR [cm$^{-1}$]/$^1$H-NMR [ppm] |
|---|---|---|
| I.181 | -N⟨(pyrrolidine-CO—OCH₃)⟩ | 1.86–2.37(m, 4H), 3.48–3.79(m, 2H), 3.63 (s, 3H), 4.65(dd, 1H), 7.66(d, 1H), 7.93 (dd, 1H), 8.10(s, 1H), 8.57(d, 1H), 8.87 (s, 1H) |
| I.182 | —SO₂—NH-(2,4-dichlorthien-3-yl) | 106–108° C. |
| I.183 | —CH₂—SCH(CH₃)₂ | 1.30(d, 6H), 2.92(h, 1H), 3.94(s, 2H), 7.50 (d, 1H), 7.62(dd, 1H), 7.89(d, 1H), 8.07 (s, 1H), 8.88(s, 1H) |
| I.184 | —SCH₂—CO—O(cyclopentyl) | 71–72° C. |
| I.185 | —CO—NH₂ | 167–168° C. |
| I.186 | —CO—NH—CH₃ | 163–164° C. |
| I.187 | —CO—NH—OC₂H₅ | 162–163° C. |
| I.188 | —CO—NH—CH[CH(CH₃)₂]—COOC₂H₅ | 90–92° C. |
| I.189 | —CO—NH—CH(CH₃)—CO—OCH₃ | 120–124° C. |
| I.190 | —NH—CO—OCH₃ | 120–122° C. |
| I.191 | —NH—CO—CO—OCH₃ | 95–97° C. |
| I.192 | —Cl | 1601, 1449, 1321, 1164, 1137, 1098, 1082, 1034, 766, 723 |
| I.193 | —CH₂—O—N=C(CH₃)₂ | 85–86° C. |
| I.194 | —SO₂—CH₃ | 116–117° C. |

TABLE 2

I ($R^1, R^3, R^5 = H$; $R^6 = Cl$)

| No. | $R^2$ | $R^4$ | $R^7$ | M.p./IR[cm$^{-1}$]/ $^1$H-NMR [ppm] |
|---|---|---|---|---|
| I.301 | CF₃ | —S—CH(CH₃)₂ | CH₂—S—CH—(CH₃)₂ | 1.28(d, 6H), 1.32 (d, 6H), 2.94(h, 1H), 3.35(h, 1H), 3.92 (s, 2H), 7.43–7.50 (m, 2H), 7.75(d, 1H), 7.90(s, 1H), 8.72(s, 1H) |
| I.302 | CF₃ | —S—CH₂—C₂H₅ | CH₂—S—CH₂—C₂H₅ | |
| I.303 | CF₃ | —S—CH₃ | CH₂—S—CH₃ | 106–108° C. |
| I.304 | CF₃ | —S—C₂H₅ | CH₂—S—C₂H₅ | 1.29(t, 3H), 1.32(t, 3H), 2.55(q, 2H), 2.90 (q, 2H), 3.90(s, 2H), 7.45–7.58(m, 2H), 7.73 (s, 1H), 7.81(s, 1H), 8.70(s, 1H); 62–63° C. |
| I.305 | CF₃ | —O—CH₂—CH=CH₂ | CH₂—O—CH₂—CH=CH₂ | 4.10–4.18(m, 2H), 4.62–4.67(m, 4H), 5.18–5.50(m, 4H), 5.88–6.14(m, 2H), 7.40–7.49(m, 2H), 7.88 (dd, 1H), 8.18(s, 1H), 8.57(s, 1H) |
| I.306 | CF₃ | —O—CH(CH₃)—C≡C—H | —CH₂O—CH(CH₃)—C≡CH | 66–67° C. |
| I.307 | CF₃ | —S—CH₃ | —O—CH₂—C≡C—H | 103–104° C. |
| I.308 | Cl | Cl | —O—CH₂—CN | 136–137° C. |

TABLE 2-continued

Structure: pyridine with R² at 5-position, R⁴ at 3-position, connected at 2-position to phenyl bearing Cl (R⁶) and R⁷

I (R¹, R³, R⁵ = H; R⁶ = Cl)

| No. | R² | R⁴ | R⁷ | M.p./IR[cm⁻¹]/ ¹H-NMR [ppm] |
|---|---|---|---|---|
| I.309 | Cl | Cl | —O—CH₂—CH=CH₂ | 64–66° C. |
| I.310 | Cl | Cl | —O—CH₂—C≡C—H | 133–134° C. |
| I.311 | Cl | Cl | —O—CH(CH₃)—C≡C—H | 146–147° C. |
| I.312 | Cl | Cl | —O—CH(CH₃)₂ | 1.41(d, 6H), 4.64 (h, 1H), 7.25(dd, 1H), 7.32(d, 1H), 7.45 (d, 1H), 7.82(d, 1H), 8.53(d, 1H) |
| I.313 | Cl | Cl | —O—CH(CH₃)—CO—OCH₃ | 1.72(d, 3H), 3.77 (s, 3H), 4.87(q, 1H), 7.26(d, 1H), 7.34 (dd, 1H), 7.49(d, 1H), 7.84(d, 1H), 8.54 (d, 1H) |
| I.314 | Cl | Cl | —O—CH(CH₃)—CO—OC₂H₅ | 1.26(t, 3H), 1.72 (d, 3H), 4.22(q, 2H), 4.83(q, 1H), 7.26 (d, 1H), 7.34(d, 1H), 7.48(dd, 1H), 7.82 (d, 1H), 8.54(d, 1H) |
| I.315 | Cl | Cl | —O—CH₂—CO—OCH₃ | 140–141° C. |
| I.316 | Cl | Cl | —O—CH₂—CO—OC₂H₅ | 67–68° C. |
| I.317 | Cl | Cl | —O—CH₃ | 122–123° C. |

TABLE 3

Structure: pyridine with F₃C at 5-position, Cl at 3-position, connected at 2-position to phenyl bearing R⁶ and R⁷

I (R¹, R³, R⁵ = H; R⁶ = CF₃)

| No. | R⁶ | R⁷ | M.p./IR[cm⁻¹] ¹H-NMR [ppm] |
|---|---|---|---|
| I.401 | CN | —NO₂ | 8.10(d, 1H), 8.20(s, 1H), 8.36(dd, 1H), 8.82(d, 1H), 8.94(s, 1H) |
| I.402 | CN | —NH₂ | 6.30(s, br., 2H), 6.85(s, br., 1H), 7.15 (s, br.1H), 7.55(s, br. 1H), 8.60(s, br., 1H), 9.05(s, br., 1H). (Solvent: DMSO-d⁶) |
| I.403 | CN | —N(SO₂—C₂H₅)₂ | 1.53(t, 6H), 3.7–3.82(m, 4H), 7.91(s, 1H), 8.02(d, 1H), 8.07(d, 1H), 8.12(s, 1H), 8.90(s, 1H) |
| I.404 | CN | —NH—SO₂—C₂H₅ | 1.44(t, 3H), 3.24(q, 2H), 7.45(s, 1H), 7.63(d, 1H), 7.72(d, 1H), 8.10(s, 2H), 8.90(s, 1H) |
| I.405 | CN | N(SO₂—CH₃)₂ | 3.58(s, 6H), 7.91(s, 1H), 7.96(d, 1H), 8.09(s, 1H), 8.12(s, 1H), 8.90(s, 1H) |
| I.406 | CN | —NH—SO₂—CH₃ | 3.20(s, 3H), 7.32(s, 1H), 7.68(dd, 1H), 7.78(d, 1H), 8.12(s, 2H), 8.90(s, 1H) |
| I.407 | CN | —CH₂—CH(Cl)—CO—OC₂H₅ | 1.29(t, 3H), 3.49(dd, 1H), 3.72(dd, 1H), 4.27(q, 2H), 4.64(t, 1H), 7.77–7.88 (m, 3H), 8.10(s, 1H), 8.89(s, 1H) |
| I.408 | F | CH₃ | 2.35(s, 3H), 7.10(t, 1H), 7.55–7.63 (m, 2H), 8.02(s, 1H), 8.81(s, 1H) |

TABLE 3-continued

Structure: I (R¹, R³, R⁵ = H; R⁶ = CF₃)
5-CF₃, 3-Cl pyridine at position 2 connected to phenyl with R⁶ and R⁷ substituents.

| No. | R⁶ | R⁷ | M.p./IR[cm⁻¹] ¹H-NMR [ppm] |
|---|---|---|---|
| I.409 | F | NO₂ | 7.47(t, 1H), 8.09–8, 19(m, 2H), 8.60 (dd, 1H), 8.89(s, 1H) |

TABLE 4

Structure: Ia (R¹ = R³ = H; R² = CF₃; R⁴ = R⁶ = Cl)
5-CF₃, 3-Cl pyridine at position 2 connected to 2-F, 4-Cl phenyl with R⁷ substituent.

| No. | R⁷ | M.p./IR [cm⁻¹]/ ¹H-NMR [ppm] |
|---|---|---|
| I.501 | —OCH₃ | 105–106° C. |
| I.502 | —O—CH₂—CH₃ | |
| I.503 | —O—CH₂CH₂CH₃ | |
| I.504 | —O—CH(CH₃)₂ | |
| Ia505 | —O—CH₂—CH₂—C₂H₅ | |
| Ia506 | —O—CH(CH₃)—C₂H₅ | |
| I.507 | —O—CH₂—CH(CH₃)₂ | |
| I.508 | —O—CH₂—CH₂—CH₂—C₂H₅ | |
| I.509 | —O—CH₂—CH=CH₂ | |
| I.510 | —OCH₂—C(H)=C(Cl)(H) | |
| I.511 | —OCH₂—C(H)=C(H)(Cl) | |
| I.512 | —O—CH₂—C≡C—H | 97–98° C. |
| I.513 | —O—CH(CH₃)C≡C—H | |
| I.514 | —O—CH₂—CO—OCH₃ | |
| I.515 | —O—CH₂—CO—OC₂H₅ | |
| I.516 | —O—CH(CH₃)—CO—OCH₃ | |
| I.517 | —O—CH(CH₃)—CO—OC₂H₅ | |
| I.518 | —O-cyclopentyl | |
| I.519 | —O—CH₂—C≡N | |
| I.520 | —O—CH(CH₃)—C≡N | |
| I.521 | —OH | 111–112° C. |
| I.522 | —O—CH₂—CO—O—(CH₂)₄—CH₃ | |
| I.523 | —O—CH(CH₃)—CO—O—(CH₂)₄—CH₃ | |
| I.524 | —O—CH₂-phenyl | |
| I.525 | —S—CH₃ | |
| I.526 | —S—C₂H₅ | |
| I.527 | —S—CH₂—C₂H₅ | |
| I.528 | —S—CH(CH₃)₂ | |
| I.529 | —S—CH₂—CH₂—C₂H₅ | |
| I.530 | —S—CH(CH₃)—C₂H₅ | |
| I.531 | —S—CH₂—CH(CH₃)₂ | |
| I.532 | —S—CH₂—CH₂—CH₂—C₂H₅ | |
| I.533 | —S—CH₂—CH=CH₂ | |
| I.534 | —SCH₂—C(H)=C(Cl)(H) | |
| I.535 | —SCH₂—C(H)=C(H)(Cl) | |
| I.536 | —S—CH₂—C≡C—H | |
| I.537 | —S—CH(CH₃)—C≡C—H | |
| I.538 | —S—CH₂—CO—OCH₃ | |
| I.539 | —S—CH₂—CO—OC₂H₅ | |
| I.540 | —S—CH(CH₃)—CO—OCH₃ | |
| I.541 | —S—CH(CH₃)—CO—OC₂H₅ | |
| I.542 | —S-cyclopentyl | |
| I.543 | —S—CH₂C≡N | |
| I.544 | —S—CH(CH₃)—C≡N | |
| I.545 | —S—CH₂—CO—O—(CH₂)₄—CH₃ | |
| I.546 | —S—CH(CH₃)—CO—O—(CH₂)₄—CH₃ | |
| I.547 | —S—CH₂-phenyl | |
| I.548 | —S—CH₂—((4-Cl-phenyl) | |
| I.549 | —SO₂—Cl | |
| I.550 | —SO₂—NH₂ | |
| I.551 | —SO₂—NH—CH₃ | |
| I.552 | —SO₂—N(CH₃)₂ | |
| I.553 | —SO₂—NH—C₂H₅ | |
| I.554 | —SO₂—N(CH₃)—C₂H₅ | |
| I.555 | —SO₂—N(C₂H₅)₂ | |
| I.556 | —SO₂-(pyrrolidin-1-yl) | |
| I.557 | —SO₂-(morpholin-4-yl) | |
| I.558 | —SO₂—NH-phenyl | |
| I.559 | —SO₂—N(CH₃)-phenyl | |
| I.560 | —SO₂—NH—CH₂-phenyl | |
| I.561 | —NO₂ | |

TABLE 4-continued

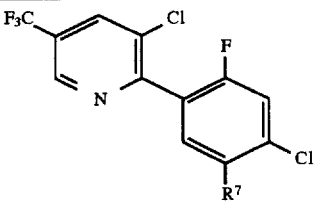

Ia (R¹ = R³ = H; R² = CF₃; R⁴ = R⁶ = Cl)

| No. | R⁷ | M.p./IR [cm⁻¹]/ ¹H-NMR [ppm] |
|---|---|---|
| I.562 | —NH₂ | |
| I.563 | —NH—SO₂—CH₃ | |
| I.564 | —N(SO₂—CH₃)₂ | |
| I.565 | —NH—SO₂—C₂H₅ | |
| I.566 | —N(SO₂—C₂H₅)₂ | |
| I.567 | —NH—SO₂—CH₂—C₂H₅ | |
| I.568 | —NH—CHO | |
| I.569 | —NH—CO—CH₃ | |
| I.570 | —NH—CO—C₂H₅ | |
| I.571 | —N(CO—CH₃)—SO₂—CH₃ | |
| I.572 | —N(CO—CH₃)—SO₂—C₂H₅ | |
| I.573 | —CH₃ | |
| I.574 | 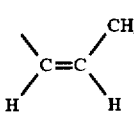 | |
| I.575 | 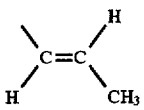 | |
| I.576 | —CH₂—Br | |
| I.577 | —CH₂—O—CH₃ | |
| I.578 | —CH₂—O—C₂H₅ | |
| I.579 | —CH₂—O—(CH₂)₂—CH₃ | |
| I.580 | —CH₂—O—CH(CH₃)₂ | |
| I.581 | —CH₂—O—(CH₂)₃—CH₃ | |
| I.582 | —CH₂—O—CH(CH₃)—C₂H₅ | |
| I.583 | —CH₂—O—CH₂—CH(CH₃)₂ | |
| I.584 | —CH₂—O—CH₂—CH=CH₂ | |
| I.585 | —CH₂—O—CH₂—C≡C—H | |
| I.586 | —CH₂—O—CH₂—CO—OCH₃ | |
| I.587 | —CH₂—O—CH₂—CO—OC₂H₅ | |
| I.588 | —CH₂—O—CH(CH₃)—CO—OCH₃ | |
| I.589 | —CH₂—O—CH(CH₃)—CO—OC₂H₅ | |
| I.590 | —CH₂—O-cyclopentyl | |
| I.591 | —CH₂—S—CH₃ | |
| I.592 | —CH₂—S—C₂H₅ | |
| I.593 | —CH₂—S—(CH₂)₂—CH₃ | |
| I.594 | —CH₂—S—CH₂—CO—OCH₃ | |
| I.595 | —CH₂—S—CH₂—CO—OC₂H₅ | |
| I.596 | —CH₂—N(CH₃)₂ | |
| I.597 | —CO—OH | |
| I.598 | —CO—OCH₃ | |
| I.599 | —CO—OC₂H₅ | |
| I.600 | —CO—O—(CH₂)₂—CH₃ | |
| I.601 | —CO—OCH(CH₃)₂ | |
| I.602 | —CO—O—(CH₂)₃—CH₃ | |
| I.603 | —CO—OCH(CH₃)—C₂H₅ | |
| I.604 | —CO—OCH₂—CH(CH₃)₂ | |
| I.605 | —CO—O—(CH₂)₄—CH₃ | |
| I.606 | —CO—OCH₂—CH₂—OCH₃ | |
| I.607 | —CO—OCH₂—CH₂—OC₂H₅ | |
| I.608 | —CHO | |
| I.609 | —CH(OCH₃)₂ | |
| I.610 | —CH(OC₂H₅)₂ | |
| I.611 | —CH(OCH₂—C₂H₅)₂ | |
| I.612 | 1,3-Dioxolan-2-yl | |
| I.613 | 4-Methyl-1,3-dioxolan-2-yl | |
| I.614 | 4-Vinyl-1,3-dioxolan-2-yl | |
| I.615 | 3,4-Dimethyl-1,3-dioxolan-2-yl | |

TABLE 4-continued

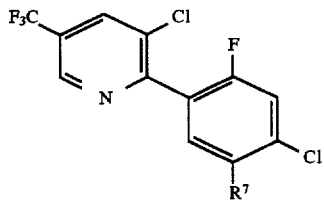

Ia (R¹ = R³ = H; R² = CF₃; R⁴ = R⁶ = Cl)

| No. | R⁷ | M.p./IR [cm⁻¹]/ ¹H-NMR [ppm] |
|---|---|---|
| I.616 | 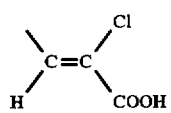 | |
| I.617 | 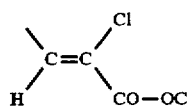 | |
| I.618 | 4-Methyl-1,3-dithiolan-2-yl | |
| I.619 | 1,3-Dioxan-2-yl | |
| I.620 | 1,3-Dithian-2-yl | |
| I.621 | —CH=N—OH | |
| I.622 | —CH=N—OCH₃ | |
| I.623 | —CH=N—OC₂H₅ | |
| I.624 | —CH=N—OCH₂—C₂H₅ | |
| I.625 | —CH=N—OCH(CH₃)₂ | |
| I.626 | —CH=N—OCH₂—CH₂—C₂H₅ | |
| I.627 | —CH=N—OCH₂—CO—OH | |
| I.628 | —CH=N—OCH₂—CO—OCH₃ | |
| I.629 | —CH=N—OCH₂—CO—OC₂H₅ | |
| I.630 | —CH=N—OCH(CH₃)—CO—OH | |
| I.631 | —CH=N—OCH(CH₃)—CO—OCH₃ | |
| I.632 | —CH=N—OCH(CH₃)—CO—OC₂H₅ | |
| I.633 | 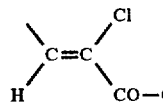 | |
| I.634 | 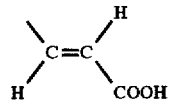 | |
| I.635 | 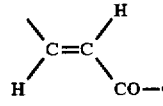 | |
| I.636 | | |
| I.637 | | |
| I.638 | 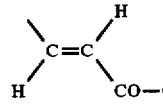 | |

TABLE 4-continued

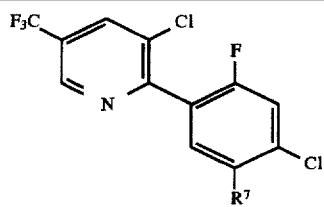

Ia (R¹ = R³ = H; R² = CF₃; R⁴ = R⁶ = Cl)

| No. | R⁷ | M.p./IR [cm⁻¹]/ ¹H-NMR [ppm] |
|---|---|---|
| I.639 | \C=C/ with CH₃ and COOH (H on other side) | |
| I.640 | \C=C/ with CH₃ and CO—OCH₃ (H) | |
| I.641 | \C=C/ with CH₃ and CO—OC₂H₅ (H) | |
| I.642 | \C=C/ with Cl and CO—NH₂ (H) | |
| I.643 | \C=C/ with Cl and CO—NHCH₃ (H) | |
| I.644 | \C=C/ with Cl and CO—N(CH₃)₂ (H) | |
| I.645 | \C=C/ with H and CO—NH₂ (H) | |
| I.646 | \C=C/ with H and CO—NHCH₃ (H) | |
| I.647 | \C=C/ with H and CO—N(CH₃)₂ (H) | |
| I.648 | \C=C/ with CH₃ and CO—NH₂ (H) | |
| I.649 | \C=C/ with CH₃ and CO—NHCH₃ (H) | |
| I.650 | \C=C/ with CH₃ and CO—N(CH₃)₂ (H) | |
| I.651 | \C=C/ with Cl and CO—CH₃ (H) | |
| I.652 | \C=C/ with H and CO—CH₃ (H) | |
| I.653 | \C=C/ with CH₃ and CO—CH₃ (H) | |
| I.654 | —CH₂—CH(Cl)—CO—CH₃ | |
| I.655 | —CH₂—CH(Cl)—CO—OCH₃ | |
| I.656 | —CH₂—CH(Cl)—CO—OC₂H₅ | |

TABLE 5

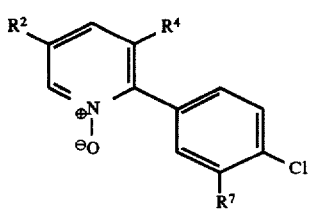

I (R¹, R³, R⁵ = H; R⁶ = Cl)

| No. | R⁴ | R⁷ | R² | M.p.\IR [cm⁻¹]\ ¹H-NMR [ppm] |
|---|---|---|---|---|
| I.801 | H | —OCH₃ | CF₃ | 133–134° C. |
| I.802 | Cl | —OCH₃ | CF₃ | 156–157° C. |
| I.803 | Cl | —O—CH₂—CN | Cl | 167–168° C. |
| I.804 | Cl | —O—CH(CH₃)—CO—OC₂H₅ | Cl | 85–87° C. |
| I.805 | Cl | —O—CH₂—CO—OC₂H₅ | Cl | 128–129° C. |

TABLE 6

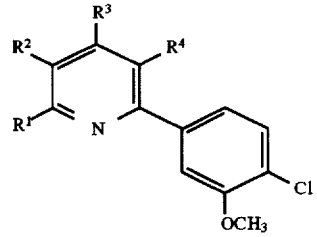

I ($R^5$ = H; $R^6$ = Cl; $R^7$ = OCH$_3$)

| No. | $R^1$ | $R^2$ | $R^3$ | $R^4$ | M.p./IR [cm$^{-1}$]/ $^1$H-NMR [ppm] |
|---|---|---|---|---|---|
| I.901 | H | CF$_3$ | H | SCH$_3$ | 100–103° C. |
| I.902 | H | CF$_3$ | H | H | 74° C.; 4.02(s, 3H), 7.49(s, 2H), 7.75(s, 1H), 7.83(d, 1H), 7.99(d, 1H), 8.94(s, 1H) |
| I.903 | H | H | H | Cl | 120–121° C.; 3.97(s, 3H), 7.20–7.35(m, 3H), 7.45(d, 1H), 7.82(dd, 1H), 8.59(d, 1H) |
| I.904 | H | CF$_3$ | H | OCH$_3$ | 62–63° C. |
| I.905 | Cl | CF$_3$ | H | Cl | 88–90° C.; 3.97(s, 3H), 7.35–7.40(m, 2H), 7.48(d, 1H), 8.10(s, 1H) |
| I.906 | H | H | H | H | |
| I.907 | H | Cl | H | H | |
| I.908 | H | H | H | CF$_3$ | |
| I.909 | Cl | CN | H | H | |
| I.910 | Cl | Cl | Cl | Cl | |
| I.911 | Cl | NO$_2$ | H | H | |
| I.912 | H | H | CF$_3$ | H | 83–84° C. |
| I.913 | Cl | H | CF$_3$ | H | |
| I.914 | CF$_3$ | H | H | H | 80–81° C. |
| I.915 | H | Cl | H | CF$_3$ | |
| I.916 | Cl | CF$_3$ | H | H | |
| I.917 | H | NO$_2$ | H | Cl | |
| I.918 | OCH$_3$ | H | H | H | |
| I.919 | Cl | Cl | SCH$_3$ | Cl | |
| I.920 | H | H | Cl | NO$_2$ | |
| I.921 | H | H | OC$_2$H$_5$ | NO$_2$ | |
| I.922 | H | NO$_2$ | H | H | |
| I.923 | H | H | H | NO$_2$ | |
| I.924 | Cl | Cl | CF$_3$ | Cl | |
| I.925 | OC$_2$H$_5$ | CF$_3$ | H | Cl | 1.44(t, 3H), 3.97(s, 3H), 4.52 (q, 2H), 7.38(dd, 1H), 7.40 (d, 1H), 7.47(d, 1H), 7.94(s, 1H) |

Examples of the herbicidal activity

The herbicidal action of the substituted 2-phenylpyridines I and I' was shown in glasshouse tests:

Plants were grown in plastic flowerpots containing loamy sand with about 3.0% humus as substrate. The seeds of the test plants were sown separately according to species.

For pre-emergence treatment, the active ingredients suspended or emulsified in water were applied immediately after sowing using finely distributing nozzles. The pots were watered lightly in order to promote germination and growth and subsequently covered with transparent plastic domes until the plants had started to grow. This covering results in uniform germination of the test plants unless this has been impaired by the active ingredients. The application rate for pre-emergence treatment was 0.0313 kg/ha active substance.

For post-emergence treatment, the test plants were grown to a height of 3 to 15 cm, depending on the species, and only then treated with the active ingredients suspended or emulsified in water. For this purpose, the test plants were either sown directly and grown in the same vessels or they were germinated separately and transplanted into the test vessels a few days before the treatment. The application rate for post-emergence treatment was 0.25, 0.125, 0.0625, 0.0313 or 0.0156 kg/ha active substance.

The plants were kept at 10°–25° C. or 20°–35° C. depending on the species. The tests lasted 2 to 4 weeks during which the plants are tended and their reaction to the individual treatments was evaluated.

Evaluation was on a scale from 0 to 100, where 100 means no emergence of the plants or complete destruction of at least the above-ground parts and 0 means no damage or normal growth.

The plants used in the glasshouse tests comprised the following species:

| Botanical name | Common name |
|---|---|
| Abutilon theophrasti | velvet leaf |
| Amaranthus retroflexus | redroot pigweed |
| Chenopodium album | lambsquarters (goose foot) |
| Ipomoea subspecies | morningglory |
| Setaria faberii | faber's foxtail; giant foxtail |
| Solanum nigrum | black nightshade |
| Stellaria media | common chickweed |
| Zea mays | corn (maize) |

At an application rate of 0.25 and 0.125 kg/ha, unwanted plants can be controlled very efficiently by the post-emergence method with compounds Nos. I.163, I.068, I.106, I.188 and I.512.

Setaria faberii in corn is controlled very efficiently by the pre-emergence method with compounds Nos. I.106 and I.512.

Examples of the growth-regulating activity

The test plants were young, 4-leaved (without seed leaves) cotton plants of the variety Stoneville 825 which had been grown under glasshouse conditions (rel. humidity 50–70%; day/night temperature 27°/20° C.).

The young cotton plants underwent foliage application until dripping wet with aqueous formulations of the stated active ingredients (with the addition of 0.15% by weight of the fatty alcohol alkoxylate Plurafac LF 700, based on the spray liquor). The amount of water applied was equivalent to 1000 l/ha. After 13 days, the number of leaves lost and the degree of defoliation in % were determined. No leaf loss occurred in the untreated control plants.

We claim:

1. A substituted 2-phenylpridine of the formula I

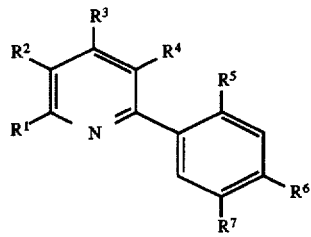

(I)

in which the variables have the following meanings:

R$^1$hydrogen, halogen, C$_1$–C$_4$-alkyl, C$_1$–C$_4$-haloalkyl, C$_1$–C$_4$-alkoxy-C$_1$–C$_4$-alkyl, C$_1$–C$_4$-alkoxy-C$_1$–C$_4$-alkoxy, C$_1$–C$_4$-haloalkoxy, (C$_1$–C$_5$-alkyl)carbonyloxy, (C$_1$–C$_5$-haloalkyl)carbonyloxy, SH, C$_1$–C$_4$-alkylthio, C$_1$–C$_4$-alkylsulfinyl, C$_1$–C$_4$-alkylsulfonyl, C$_1$–C$_4$-haloalkylthio, C$_1$–C$_4$-haloalkylsulfinyl, C$_1$–C$_4$- haloalkylsulfonyl, formyl, cyano, hydroxycarbonyl, (C$_1$-C$_4$-alkoxy) carbonyl, C$_1$-C$_4$-alkoxy(C$_1$-C$_4$-alkoxy)carbonyl, (C$_1$-C$_4$-haloalkoxy)carbonyl, (C$_1$-C$_4$-alkyl(carbonyl, (C$_1$-C$_4$-haloalkyl) carbonyl, C$_1$-C$_4$-alkoxy(C$_1$-C$_4$-alkyl)carbonyl, CONH$_2$, (C$_1$-C$_4$-alkyl)aminocarbonyl, di-(C$_1$-C$_4$-alkyl) aminocarbonyl, pyrrolidinylcarbonyl, piperidinylcarbonyl morpholinylcarbonyl, nitro, amino, C$_1$-C$_4$-alkylamino, di-(C$_1$-C$_4$-alkyl)amino, pyrrolidinyl, piperidinyl, morpholinyl, (C$_1$-C$_4$-alkyl) carbonylamino, (C$_1$-C$_4$-haloalkyl)carbonylamino or C$_1$-C$_4$-alkylsulfonylamino;

R$^2$ halogen, cyano, nitro, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, or C$_1$-C$_4$-haloalkylthio, or together with R$^1$ or with R$^3$ a trimethylene or tetramethylene chain;

R$^3$ hydrogen, halogen, C$_1$-C$_4$-alkyl, C$_1$-C$_4$-haloalkyl, C$_1$-C$_4$-alkoxy-C$_1$-C$_4$-alkyl, C$_1$-C$_4$-alkoxy, C$_1$-C$_4$-alkoxy-C$_1$-C$_4$-alkoxy, hydroxyl, C$_1$-C$_4$-haloalkoxy, (C$_1$-C$_5$-alkyl)carbonyloxy, (C$_1$-C$_5$-haloalkyl) carbonyloxy, SH, C$_1$-C$_4$-alkylthio, C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl, formyl, cyano, hydroxycarbonyl, (C$_1$-C$_4$-alkoxy)carbonyl, C$_1$-C$_4$-alkoxy(C$_1$-C$_4$-alkoxy)carbonyl, (C$_1$-C$_4$-haloalkoxy)carbonyl, (C$_1$-C$_4$-alkyl)carbonyl, (C$_1$-C$_4$-haloalkyl)carbonyl, C$_1$-C$_4$-alkoxy-(C$_1$-C$_4$C-alkyl)carbonyl, CONH$_2$, (C$_1$-C$_4$-alkyl)aminocarbonyl, di-(C$_1$-C$_4$-alkyl) aminocarbonyl, pyrrolidinylcarbonyl, piperidinylcarbonyl, morpholinylcarbonyl, nitro, amino, C$_1$-C$_4$-alkylamino, di-(C$_1$-C$_4$-alkyl)amino, pyrrolidinyl, piperidinyl, morpholinyl, (C$_1$-C$_4$-alkyl) carbonylamino, (C$_1$-C$_4$-haloalkyl)carbonylamino or C$_1$-C$_4$-alkylsulfonylamino;

R$^4$ halogen, C$_1$-C$_4$-alkyl, C$_1$-C$_4$-haloalkyl, C$_1$-C$_4$-alkoxy-C$_1$-C$_4$-alkyl, C$_1$-C$_4$-alkoxy, C$_1$-C$_4$-alkoxy, hydroxyl, C$_1$-C$_4$-haloalkoxy, (C$_1$-C$_5$-alkyl) carbonyloxy, (C$_1$-C$_5$-haloalkyl)carbonyloxy, SH, C$_1$-C$_4$-alkylthio, C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl, formyl, cyano, hydroxycarbonyl, (C$_1$-C$_4$-alkoxy)carbonyl, C$_1$-C$_4$-alkoxy-(C$_1$-C$_4$-alkoxy)carbonyl, (C$_1$-C$_4$-haloalkoxy)carbonyl, (C$_1$-C$_4$-alkyl)carbonyl, (C$_1$-C$_4$-haloalkyl)carbonyl, C$_1$-C$_4$-alkoxy-(C$_1$-C$_4$-alkyl) carbonyl, nitro, amino, C$_1$-C$_4$-alkylamino, di-(C$_1$-C$_4$-alkyl)amino, pyrrolidinyl, piperidinyl, morpholinyl, (C$_1$-C$_4$-alkyl)carbonylamino, (C$_1$-C$_4$-haloalkyl) carbonylamino or C$_1$-C$_4$-alkylsulfonylamino;

R$^5$ is hydrogen or halogen;

R$^6$ is halogen, cyano, nitro, hydroxyl, trifluoromethyl, C$_1$-C$_6$-alkyl or C$_1$-C$_4$-alkoxy;

R$^7$ chlorine, bromine, iodine, cyano, nitro, C$_1$-C$_8$-alkyl, C$_2$-C$_8$-alkenyl, C$_2$-C$_8$-alkynyl, C$_1$-C$_8$-haloalkyl, C$_2$-C$_8$-haloalkenyl, C$_2$-C$_8$-haloalkynyl, —(C$_1$-C$_8$-alkylene)-O—R$^8$, —(C$_2$-C$_8$-alkenylene)-O—R$^8$-alkenylene-S—R$^8$, —C$_2$-C$_8$-alkenylene)-S—R$^8$, —(C$_2$-C$_8$-alkylene)-S—R$^8$, —C$_1$-C$_8$-alkylene)-SO—R$^8$, —(C$_2$-C$_8$-alkenylene)-SO—R$^8$, —(C$_2$-C$_8$-alkynylene)-SO—R$^8$, —(C$_1$-C$_8$-alkylene)-SO$_2$—R$^8$, —(C$_2$-C$_8$-alkenylene)-SO$_2$—R$^8$, —(C$_2$-C$_8$-alkynylene)-SO$_2$—R$^8$, —O—R$_8$, —S—R$^8$, —SO—R$^8$, —SO$_2$—R$^8$, chlorosulfonyl, —SO$_2$—O—R$^8$, —SO$_2$—N(R$^9$,R$^{10}$), —SO$_2$—NR$^9$(CO—R$^{12}$), —N(R$^9$,R$^{10}$), —NR$^{11}$(CO—R$^{12}$), —NR$^{11}$(SO$_2$—R$^{13}$), —N(SO$_2$—R$^{13}$)(SO$_2$—R$^{14}$), —N(SO$_2$—R$^{13}$)(CO—R$^{12}$), —NH—CO—O—R$^8$, —O—CO—NHR$^9$, —O—CO—R$^{12}$, —NH—CO—NHR$^9$, —O—CS—N(C$_1$-C$_4$-alkyl)$_2$, —O—CS—NH$_2$, cyano-C$_1$14 C$_4$-alkyl, —CO—R$^8$, —CO—O—N=C(R$^{26}$,R$^{27}$), —CO—O—CH$_2$—O—N=C(R$^{30}$,R$^{31}$), —CO—O—C(R$^{28}$,R$^{29}$)—CH$_2$—ON=C(R$^{30}$,R$^{31}$), —CO—N(R$^9$, R$^{10}$), —CS—N(R$^9$,R$^{10}$), —CO—NH—SO$_2$—(C$_1$-C$_4$-alkyl), isoxazolinylcarbonyl, formyl, —CO—R$^{15}$, hydroxycarbonyl-C$_1$-C$_6$-alkyl, (C$_1$14 C$_6$-alkoxy) carbonyl-C$_1$-C$_6$-alkyl, —CR$^{15}$=C(R$^{16}$)—CHO, —C(R$^{15}$)=C(R$^{16}$)—CO—O—R$^8$, —C(R$^{15}$)=C(R$^{16}$)—CO—N(R$^9$,R$^{10}$), —C(R$^{15}$)=C(R$^{16}$)—CO—R$^{17}$, —CH=N—O—R$^8$, —CH(XR$^{18}$,YR$^{19}$), —CH$_2$—CH (halogen)-CO—O—R$^8$, —CH$_2$—CH(halogen)-CO—N(R$^9$,R$^{10}$), —CH$_2$—CH(halogen)-CO—(C$_1$-C$_4$-alkyl), —CH$_2$—CH(halogen)-CN, —C(C$_1$-C$_4$-alkoxy)=N—O—R$^8$, —C(R$^{15}$)=C(R$^{16}$)—C(C$_1$-C$_4$-alkoxy)=N—O—R$^8$, —CH=CH—CH=CH—CO—O—R$^8$,

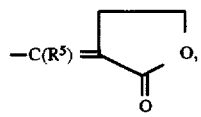

—C(R$^{15}$)=N—O—R$^8$, —CO—OCH=N—OH, —CO—OCH=N—O—(C$_1$-C$_4$alkyl), —CO—OC (C$_1$-C$_4$-alkyl)=N—OH, —CO—OC(C$_1$-C$_4$-alkyl)=N—O—(C$_1$-C$_4$-alkyl), —CO—O—(CO$_1$-C$_4$-alkylene)—CH=N—OH, —CO—O—(C$_1$-C$_4$-alkylene)-CH=N—O—(C$_1$-C$_4$-alkyl), —CO—O—(C$_1$-C$_4$-alkylene)-C(C$_1$-C$_4$-alkylene)-C(C$_{11}$-C$_4$-alkyl) =N—OH, —CO—O—(C$_1$-C$_4$-alkyl)=N—O—(C$_1$-C$_4$-alkyl), —(C$_1$-C$_8$-alkylene)-O—CO—(C$_1$-C$_4$-alkyl), —CH=C=CH$_2$, —CH=C=CH—(C$_1$-C$_4$-alkyl),

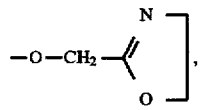

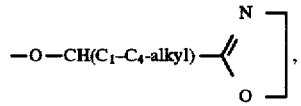

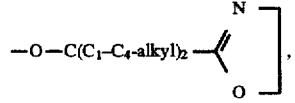

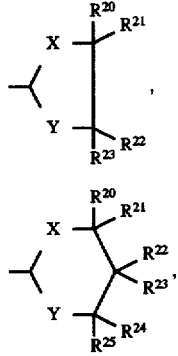

5- or 6-membered heteroaryl with one to three hetero atoms selected from a group comprising one or two nitrogen atoms and one oxygen or sulfur atom, it being possible for each heteroaromatic ring atom which can be substituted to carry a radical selected from the group comprising nitro, halogen, $C_1$–$C_4$-alkyl, $C_1$–$C_4$-alkoxy, $C_1$–$C_4$-alkylthio and ($C_1$–$C_4$-alkoxy)carbonyl;

$R^8$ hydrogen, $C_1$–$C_8$-alkyl, $C_1$–$C_8$-haloalkyl, $C_4$–$C_7$-cycloalkyl, which in turn can carry one to three $C_1$–$C_3$-alkyl radicals, $C_3$–$C_6$-alkenyl, $C_5$–$C_7$-cycloalkenyl, which in turn can carry one to three $C_1$–$C_3$-alkyl radicals, $C_3$–$C_6$-haloalkenyl, cyano-$C_1$–$C_8$-alkyl, $C_3$–$C_6$-alkynyl, $C_2$–$C_8$-alkoxyalkyl, 2-tetrahydrofuranyl-$C_1$–$C_8$-alkyl, 3-oxetanyl, 3-thietanyl, carboxyl-$C_1$–$C_6$-alkyl, ($C_1$–$C_8$-alkoxy) carbonyl-$C_1$–$C_6$-alkyl, ($C_1$–$C_6$-alkoxy)carbonyl-($C_3$–$C_7$-cycloalkyl), $C_1$–$C_4$-alkoxy-($C_1$–$C_4$-alkoxy) carbonyl-$C_1$–$C_6$-alkyl, cyclopropylmethyl, (1-methylthiocyclopropyl)methyl, —CH(SH)—CO—OH, —CH(SH)—CO—($C_1$–$C_8$-alkoxy), —CH($C_1$–$C_8$alkylthio)-COOH, —CH($C_1$–$C_4$-alkylthio)-CO—($C_1$–$C_8$-alkoxy), —CH$_2$—CO—N($R^9$)—$R^{10}$, —CH($C_1$–$C_4$-alkyl)-CO—N($R^9$)—$R^{10}$, —($C^1$–$C_4$-alkyl)$_2$—CO—N($R^9$)—$R^{10}$, —$CH_2$—CO—N($^9$)—$SO_2$—($C_1$–$C_4$-alkyl), —CH($C_1$–$C_4$-alkyl)-CO—N($R^9$) —$SO_2$—C($C_1$–$C_4$-alkyl)$_2$-CO—N($R^9$)—$SO_2$—($C_1$–$C_4$-alkyl), —S—CO—$NH_2$, —S—CO—N($C_1$-alkyl)-($C_1$–$C_4$-alkyl), $CH_2$—CO—O—($C_1$–$C_6$-alkylene)-COOH, —$CH_2$—CO—O—($C_1$–$C_6$-alkylene)-CO—($C_1$–$C_6$-alkoxy), —C($C_1$–$C_4$-alkyl)$_2$—CO—O—($C_1$–$C_6$-alkylene)-COOH, —($C_1$–$C_4$-alkyl)$_2$—CO—O—($C_1$–$C_4$-alkylene)—CO—($C_1$–$C_6$-alkoxy), —CH($C_1$–$C_4$-alkyl)-CO—O—($C_1$–$C_6$-alkylene)-COOH, —CH($C_1$–$C_4$-alkyl)-CO—O—($C_1$–$C_6$-alkylene)-CO—($C_1$–$C_6$-alkoxy), $C_3$–$C_9$-(α-alkylalkylidene)iminooxy-$C_1$–$C_6$-alkyl, phenyl, phenyl-$C_1$–$C_6$-alkyl, phenyl-$C_3$–$C_6$-alkenyl, phenyl-$C_3$–$C_6$-alkynyl or phenoxy-$C_1$–$C_6$-alkyl, where the phenyl ring can in each case be unsubstituted or carry one to three radicals selected from the group comprising halogen, nitro, cyano, $C_1$–$C_4$-alkyl, $C_1$–$C_4$-alkoxy, $C_1$–$C_4$-alkylthio, $C_1$–$C_4$-haloalkyl and $C_2$–$C_6$-alkenyl;

5- or 6-membered heteroaryl, heteroaryl-$C_1$–$C_6$-alkyl, heteroaryl-$C_3$–$C_6$-alkenyl, heteroaryl-$C_3$–$C_6$-alkynyl or heteroaryloxy-$C_1$–$C_6$-alkyl, where the heteroaryl radical in each case contains one to three hetero atoms selected from a group comprising one or two nitrogen atoms and one oxygen or sulfur atom, and it being possible for each heteroaromatic ring atom which can be substituted also to carry a radical selected from the group comprising hydroxyl, halogen, $C_1$–$C_4$-alkyl, $C_1$–$C_4$-alkoxy, $C_1$–$C_4$-alkylthio and $C_1$–$C_4$-haloalkyl;

$R^9$ and $R^{10}$ hydrogen, $C_1$–$C_8$-alkyl, $C_2$–$C_8$-alkenyl, $C_3$–$C_8$-alkynyl, $C_1$–$C_8$-haloalkyl, $C_1$–$C_4$-alkoxy-$C_1$–$C_4$-alkyl, $C_1$–$C_4$-alkylthio-$C_1$–$C_4$-alkyl, cyano-$C_1$–$C_8$-alkyl, carboxyl-$C_1$–$C_4$-alkyl, ($C_1$–$C_4$-alkoxy) carbonyl-$C_1$–$C_4$-alkyl, ($C_1$–$C_6$-alkoxy)carbonyl-($C_3$–$C_7$-cycloalkyl), $C_1$–$C_4$-alkylsulfonyl-$C_1$–$C_4$-alkyl, $C_3$–$C_8$-cycloalkyl, $C_1$–$C_6$-alkoxy, ($C_3$–$C_6$-cycloalkoxy)carbonyl-$C_1$–$C_4$-alkyl, $C_1$–$C_4$-alkoxy-($C_1$–$C_4$-alkoxy)carbonyl-$C_1$–$C_4$-alkyl, phenyl, phenyl-$C_1$–$C_4$-alkyl, where the phenyl ring can in each case be unsubstituted or carry one to three radicals selected from the group comprising halogen, nitro, cyano, $C_1$–$C_4$-alkyl, $C_1$–$C_4$-alkoxy, $C_1$–$C_4$-alkylthio, $C_1$–$C_4$-haloalkyl and $C_2$–$C_6$-alkenyl, 5- or 6-membered heteroaryl or heteroaryl-$C_1$–$C_4$-alkyl, where the heteroaryl radical contains one to three hetero atoms selected from a group comprising one or two nitrogen atoms and one oxygen or sulfur atom, and it being possible for each heteroaromatic ring atom which can be substituted also to carry a radical selected from the group comprising hydroxyl, halogen, $C_1$–$C_4$-alkyl, $C_1$–$C_4$-alkoxy, $C_1$–$C_4$-alkylthio and $C_1$–$C_4$-haloalkyl; or $R^9$ and $R^{10}$ together a tetramethylene, pentamethylene or ethyleneoxyethylene chain, it being possible for each chain to carry a ($C_1$–$C_6$-alkoxy)carbonyl radical;

$R^{11}$ hydrogen, $C^1$–$C_4$-alkyl, $C_3$–$C_6$-alkenyl, $C_3$–$C_6$-alkynyl, $C_1$–$C_4$-alkoxy-$C_1$–$C_4$-alkyl, sodium, potassium, calcium, magnesium, ammonium or ammonium which is substituted by one to four $C_1$–$C_4$-alkyl- or benzyl radicals and can carry one to three further $C_1$–$C_4$-alkyl radicals;

$R^{12}$ hydrogen, $C_1$–$C_6$-alkyl, $C_1$–$C_6$-haloalkyl, $C_1$–$C_4$-alkoxy-$C_1C_4$-alkyl, $C_3$–$C_7$-cacloalkyl, which can in turn carry one to three radicals selected from the group comprising halogen, $C_1$–$C_4$-alkyl, $C_1$–$C_4$-alkoxy and $C_1$–$C_4$-alkylthio, phenyl or phenyl-$C_1$–$C_6$-alkyl, where the phenyl ring can in each case be unsubstituted or carry one to three radicals selected from the group comprising halogen, nitro, $C_1$–$C_4$-alkyl, $C_1$–$C_4$-alkoxy, $C_1$–$C_4$-alkylthio and $C_1$–$C_4$-haloalkyl;

$R^{13}$ and $R^{14}$, independently of one another, $C_1$–$C_4$-alkyl, phenyl or thienyl, where the phenyl or thienyl radical can be unsubstituted or carry one to three radicals selected from the group comprising halogen, nitro, $C_1$–$C_4$-alkyl, $C_1$–$C_4$-alkoxy, $C_1$–$C_4$-alkylthio and $C_1$–$C_4$-haloalkyl;

$R^{15}$, $R^{16}$ and $R^{17}$, independently of one another, hydrogen, halogen, $C_1$–$C_4$-alkyl, $C_2$–$C_4$-alkenyl, $C_1$–$C_4$-haloalkyl, $C_1$–$C_4$-alkoxy-$C_1$–$C_4$-alkyl or $C_1$–$C_4$-alkylthio-$C_1$–$C_4$-alkyl;

$R^{18}$ and $R^{19}$, independently of one another, $C_1$–$C_8$-alkyl, $C_1$–$C_4$-alkoxy-$C_1$–$C_4$-alkyl or $C_1$–$C_8$-haloalkyl;

$R^{20}$, $R^{21}$, $R^{22}$, $R^{23}$, $R^{24}$ and $R^{25}$, independently of one another, hydrogen, cyano, $C_1$–$C_8$-alkyl, $C_1$–$C_4$-alkoxy-$C_1$–$C_4$-alkyl, halo -$C_1$–$C_8$-alkyl, $C_1$–$C_8$-alkoxy, $C_1$–$C_4$-alkoxy-$C_1$–$C_4$-alkoxy, —CO—O—$R^8$, —CO—N ($R^9$,$R^{10}$), —CO—$R^{15}$, —S—$R^8$, —$SO_2$—$R^8$, —O—CO—$R^{12}$ or $C_3$–$C_7$-cycloalkyl, which can in turn carry from one to three radicals selected from the group comprising halogen, $C_1$–$C_4$-alkyl, $C_1$–$C_4$-alkoxy and $C_1$–$C_4$-alkylthio;

$R^{26}$ $C_1$–$C_6$-alkyl, $C_1$–$C_6$-alkylthio, $C_1$–$C_6$-alkoxycarbonyl or $C_1$–$C_6$-alkoxycarbonyl-$C_1$–$C_4$-alkyl;

$R^{27}$ $C_1$–$C_6$-alkyl, trifluoromethyl, $C_1$–$C_6$-alkoxy-$C_1$–$C_4$-alkyl, $C_2$–$C_7$-alkoxycarbonyl-$C_1$–$C_4$-alkyl, di-($C_1$–$C_6$-alkoxycarbonyl)-$C_1$–$C_4$-alkyl, $C_3$–$C_6$-cycloalkyl, $C_1$–$C_6$-alkoxy, $C_1$–$C_6$-alkylthio, $C_1$–$C_6$-alkanoyl, $C_1$–$C_6$-alkoxycarbonyl, 2-furyl or phenyl which can be unsubstituted or in turn carry one to three radicals selected from the group comprising halogen, $C_1$–$C_4$-alkyl and $C_1$–$C_4$-alkoxy; or $R^{26}$ and $R^{27}$ together with the carbon to which they are bonded a cyclopentane or cyclohexane ring which can in turn carry one to three $C_1$–$C_4$-alkyl radicals;

$R^{28}$ hydrogen or $C_1$–$C_4$-alkyl;

$R^{29}$ hydrogen, $C_1$–$C_4$-alkyl, phenyl or benzyl;

$R^{30}$ hydrogen or $C_1$–$C_6$-alkyl;

$R^{31}$ $C_1$–$C_6$-alkyl, $C_3$–$C_6$-cycloalkyl or phenyl;

X and Y, independently of one another, oxygen or sulfur; and the N-oxides of I and the agriculturally utilizable salts of I where these exist, excepting those compounds I where $R^2$ is $C_1$–$C_4$-alkoxy and $R^1$ and/or $R^3$ is carboxyl, its salt, ester or amide.

2. A substituted 2-phenylpyridine of the formula 1 as defined in claim 1, where $R^1$ and $R^3$ are hydrogen or halogen, $R^2$ is halogen, $C_1$–$C_4$-haloalkyl with one to five halogen atoms or $C_1$–$C_4$-haloalkoxy with one to five halogen atoms, $R^4$ is halogen, $R^5$ is hydrogen, fluorine or chlorine, $R^6$ is chlorine and $R^7$ is —O—$R^8$, —S—$R^8$, —$NR^{11}$—$SO_2R^{13}$, —$COOR^8$, —$CR^{15}$=$CR^{16}$—$COOR^8$, —CH=N—O—$R^8$, —CH(X—$R^{18}$)(X—$R^{19}$), —$CH_2$—

$CH(Cl)$—$COOR^8$, —$SO_2NR^9R^{10}$,

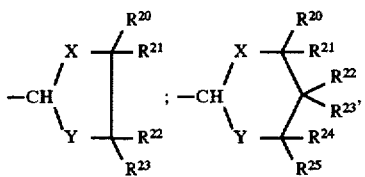

3. A substituted 2-phenylpyridine of the formula I as defined in claim 1, where $R^1$ and $R^3$ are hydrogen or halogen;

$R^2$ is halogen or $C_1$-$C_4$-haloalkyl with one to five halogen atoms, $R^4$ is halogen, $R^5$ is hydrogen, fluorine or chlorine, $R^6$ is halogen or cyano, and $R^7$ is —O—$R^8$, —S—$R^8$, —$NR^{11}$—$SO_2R^{13}$, —$COOR^8$, —$CR^{15}$=$CR^{16}$—$COOR^8$, —CH=N—O—$R^8$, —$CH(X-R^{18})(X-R^{19})$, —$CH_2$—CH(Cl)—$COOR^8$, —$SO_2NR^9R^{10}$,

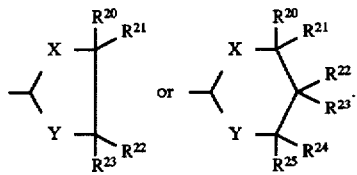

4. A substituted 2-phenylpyridine of the formula I as defined in claim 3, where $R^6$ is chlorine or cyano.

5. A substituted 2-phenylpyridine of the formula I as defined in claim 4, where $R^8$ is hydrogen, $C_1$-$C_8$-alkyl, $C_3$-$C_6$-alkenyl, cyano-$C_1$-$C_8$-alkyl, $C_3$-$C_6$-alkynyl, $C_2$-$C_8$-alkoxyalkyl, carboxyl-$C_1$-$C_6$-alkyl, ($C_1$-$C_8$-alkoxy)carbonyl-$C_1$-$C_6$-alkyl, $C_1$-$C_4$-alkoxy-($C_1$-$C_4$-alkoxy)carbonyl-$C_1$-$C_6$-alkyl, —$CH_2$—CO—N($R^9$)—$R^{10}$, —CH($C_1$-$C_4$-alkyl)-CO—N($R^9$)—$R^{10}$, $CH_2$—CO—O—($C_1$-$C_6$-alkylene)-COOH, —$CH_2$—CO—O—($C_1$-$C_6$-alkylene)-CO—($C_1$-$C_6$-alkoxy), —CH($C_1$-$C_4$-alkyl)-CO—O—($C_1$-$C_6$-alkylene)-COOH or —CH($C_1$-$C_4$-alkyl)-CO—O—($C_1$-$C_6$-alkylene)-CO—($C_1$-$C_6$-alkoxy);

$R^9$ and $R^{10}$ hydrogen or $C_1$-$C_8$-alkyl;

$R^{11}$ hydrogen or $C_1$-$C_4$-alkyl;

$R^{13}$ $C_1$-$C_4$-alkyl;

$R^{15}$ and $R^{16}$, independently of one another, hydrogen, halogen or $C_1$-$C_4$-alkyl;

$R^{18}$ and $R^{19}$, independently of one another, $C_1$-$C_8$-alkyl;

$R^{20}$, $R^{21}$, $R^{22}$, $R^{23}$, $R^{24}$ and $R^{25}$, independently of one another, hydrogen or $C_1$-$C_8$-alkyl.

6. A herbicidal composition containing a herbicidally effective amount of at least one substituted 2-phenylpyridine of the formula I or its N-oxide or agriculturally utilizable salt, as defined in claim 1, and at least one inert liquid and/or solid carrier and, if desired, at least one adjuvant.

7. A composition for the desiccation and/or defoliation of plants, containing an amount, which has desiccant and/or defoliant activity, of at least one substituted 2-phenylpyridine of the formula I or its N-oxide or its agriculturally utilizable salt, as defined in claim 1, and at least one inert liquid and/or solid carrier and, if desired, at least one adjuvant.

8. A process for the production of herbicidal compositions, which comprises mixing a herbicidally effective amount of at least one substituted 2-phenylpyridine of the formula I or its N-oxide or its agriculturally utilizable salt, as defined in claim 1, and at least one inert liquid and/or solid carrier and, if desired, at least one adjuvant.

9. The process for the production of desiccant and/or defoliant compositions, which comprises mixing an amount, which has defoliant and/or desiccant activity, of at least one substituted 2-phenylpyridine of the formula I or its N-oxide or its agriculturally utilizable salt, as defined in claim 1, and at least one inert liquid and/or solid carrier and, if desired, at least one adjuvant.

10. A method for controlling unwanted plant growth, which comprises allowing a herbicidally effective amount of at least one substituted 2-phenylpyridine of the formula I as defined in claim 1, or its N-oxide or agriculturally utilizable salt, to act on plants, their habitat or on seeds.

11. A method for the desiccation and defoliation of plants, which comprises allowing an amount, which has defoliant and/or desiccant activity, of at least one substituted 2-phenylpyridine of the formula I as defined in claim 1, or its N-oxide or agriculturally utilizable salt, to act on plants.

12. The method of claim 11, wherein cotton is defoliated.

13. A process for the preparation of substituted 2-phenylpyridines of the formula I as defined in claim 1, which comprises reacting a 2-halopyridine of the formula II

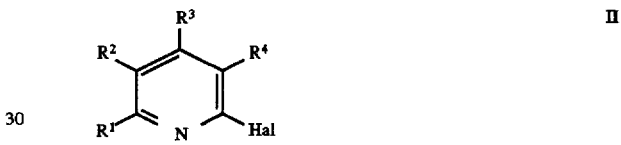

where Hal is chlorine or bromine, in the presence of a transition metal catalyst with an organometallic compound of the formula III

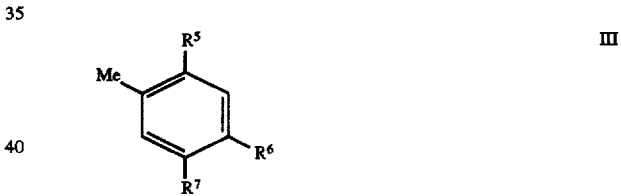

where Me is magnesium bromide, zinc bromide, zinc chloride, tin tri($C_1$-$C_8$-alkyl), lithium, copper or B($OR^{33}$)($OR^{34}$) where $R^{33}$ and $R^{34}$ are, independently of one another, hydrogen or $C_1$-$C_4$-alkyl or together are ethylene or propylene.

14. The process of claim 13, wherein Me in the compound III is B(OH)$_2$.

15. A process for the preparation of substituted 2-phenylpyridines of the formula I as in claim 1 comprising the step of reacting phenylpyridines of the formula IV

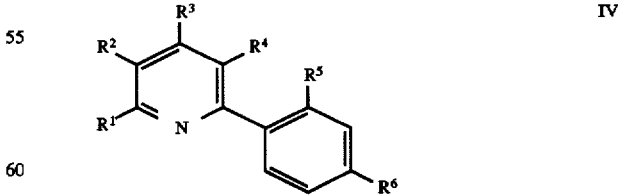

in which the substituents $R^1$ to $R^6$ have the appropriate meanings for the substituted 2-phenylpyridines of the formula I as defined in claim 1.

* * * * *

UNITED STATES PATENT AND TRADEMARK OFFICE
CERTIFICATE OF CORRECTION

Page 1 of 2

PATENT NO. : 5,783,522
DATED : July 21, 1998
INVENTOR(S) : Schaefer, et. al.

It is certified that error appears in the above-identified patent and that said Letters Patent is hereby corrected as shown below:

Col. 66, claim 1, line 50, "2-phenylpridine" should be --2-phenylpyridine--.
Col. 67, claim 1, line 2, "$C_1$-$C_4$-alkoxy($C_1$-$C_4$-" should be --$C_1$-$C_4$-alkoxy-($C_1$-$C_4$- --.
Col. 67, claim 1, line 4, "($C_1$-$C_4$-alkyl(carbonyl," should be --($C_1$-$C_4$-alkyl)carbonyl,--.
Col. 67, claim 1, line 5, "$C_1$-$C_4$-alkoxy($C_1$-$C_4$-alkyl)carbonyl" should be --$C_1$-$C_4$-alkoxy-($C_1$-$C_4$-alkyl)carbonyl,--.
Col. 67, claim 1, line 8, after "bonyl" insert a comma --,--.
Col. 67, claim 1, line 37, the second occurrence of "$C_1$-$C_4$-alkoxy," should be --$C_1$-$C_4$-alkoxy-$C_1$-$C_4$-alkoxy,--.
Col. 67, claim 1, at the end of line 56, delete the "-" (hyphen), and insert therefore -- , -($C_2$-$C_8$ - alkynylene) -O-$R^8$,--
Col. 67, claim 1, line 57, "-alkenylene" should be -- -($C_1$-$C_8$-alkylene)--.
Col. 67, claim 1, line 57, "-$C_2$-$C_8$-alkylene)-SO-" should be -- -($C_2$-$C_8$-alkylene)-SO- --.
Col. 67, claim 1, line 58, "-($C_2$-$C_8$-alkylene)-S-$R^8$" should be -- -($C_2$-$C_8$-alkynylene)-S-$R^8$--.
Col. 67, claim 1, line 58, "-$C_2$-$C_8$-alkylene)-SO-" should be -- -($C_2$-$C_8$-alkylene)-SO- --.
Col. 68, claim 1, lines 2 and 3, "cyano-$C_1$14$C_4$-alkyl," should be --cyano-$C_1$-$C_4$-alkyl,--.
Col. 68, claim 1, line 3, "-CO-$R^8$" should be ---CO-O-$R^8$--.
Col. 68, claim 1, line 8, "($C_1$14 $C_6$-alkoxy)" should be --($C_1$-$C_6$-alkoxy)--.

UNITED STATES PATENT AND TRADEMARK OFFICE
CERTIFICATE OF CORRECTION

PATENT NO. : 5,783,522
DATED : July 21, 1998
INVENTOR(S) : Schaefer, et. al.

It is certified that error appears in the above-identified patent and that said Letters Patent is hereby corrected as shown below:

Col. 68, claim 1, line 29, delete "-C($C_1$-$C_4$-alkylene)".
Col. 68, claim 1, line 29, "$C_{11}$-$C_4$-alkyl" should be --$C_1$-$C_4$-alkyl--.
Col. 68, claim 1, line 30, "-CO-O-($C_1$-$C_4$-alkyl)=N-O-" should be
  -- -CO-O-($C_1$-$C_4$-alkylene)-($C_1$-$C_4$-alkyl)=N-O- --.
Col. 69, claim 1, line 16, "-($C^1$-$C_4$-" should be -- -C($C_1$-$C_4$- --.
Col. 69, claim 1, line 17, "-$CH_2$-CO-N($^9$)" should be -- -$CH_2$-CO-N($R^9$)--.
Col. 69, claim 1, line 19, "-$SO_2$-(" should be -- -$SO_2$-($C_1$-$C_4$-alkyl)-( --.
Col. 69, claim 1, line 20 bridging line 21, "N($C_1$--alkyl)" should be --N($C_1$-$C_4$-alkyl)--.
Col. 69, claim 1, line 24 bridging line 25,
  "-($C_1$-$C_4$-alkyl)
  $_2$"
  should be -- -C($C_1$-$C_4$-alkyl)$_2$--.
Col. 70, claim 1, line 8, "$C_3$-$C_7$-cacloalkyl" should be --$C_3$-$C_7$-cycloalkyl--.
Col. 70, claim 2, line 1, "formula 1" should be --formula I--.
Col. 71, in the right-hand formula on line 5, "$R^{23"}$" should be --$R^{23}$--.
Col. 71, claim 3, line 20 bridging line 21, "-$CH$(X-$R^{18}$)" should be -- -CH(X-$R^{18}$)--.

Signed and Sealed this

Ninth Day of February, 1999

Attest:

Attesting Officer

*Acting Commissioner of Patents and Trademarks*

UNITED STATES PATENT AND TRADEMARK OFFICE
CERTIFICATE OF CORRECTION

PATENT NO.: 5,783,522

DATED: July 21, 1998

INVENTOR(S): SCHAEFER et al.

It is certified that error appears in the above-identified patent and that said Letters Patent is hereby corrected as shown below:

Column 67, claim 1, line 29 "-($C_1$-$C_4$C-alkyl)carbonyl"
should be -- -$C_1$-$C_4$-alkyl)carbonyl --.

Column 68, claim 1, line 7, "isoxazolinylcarbonyl" should be --isoxazolidinylcarbonyl--.

Column 68, claim 1, line 26, "-CO-O-($CO_1$-$C_4$-" should be -- -CO-O-($C_1$-$C_4$- --.

Column 69, claim 1, line 15, "($C_1$-$C_8$alkylthio)-COOH" should be
--($C_1$-$C_8$-alkylthio)-COOH --.

Column 70, claim 1, line 1, "$C^1$-$C_4$-alkyl" should be --$C_1$-$C_4$-alkyl--.

Column 70, claim 1, line 8, "alkoxy-$C_1C_4$-alkyl" should be --alkoxy-$C_1$-$C_4$-alkyl--.

Signed and Sealed this

First Day of June, 1999

*Attest:*

Q. TODD DICKINSON

*Attesting Officer*     *Acting Commissioner of Patents and Trademarks*